(12) United States Patent
Yamaguchi et al.

(10) Patent No.: US 12,102,000 B2
(45) Date of Patent: Sep. 24, 2024

(54) LIGHT-EMITTING ELEMENT, ORGANIC COMPOUND, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomoya Yamaguchi, Kanagawa (JP); Hideko Yoshizumi, Kanagawa (JP); Hiromitsu Kido, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 792 days.

(21) Appl. No.: 16/473,372

(22) PCT Filed: Dec. 15, 2017

(86) PCT No.: PCT/IB2017/057977
§ 371 (c)(1),
(2) Date: Jun. 25, 2019

(87) PCT Pub. No.: WO2018/122664
PCT Pub. Date: Jul. 5, 2018

(65) Prior Publication Data
US 2020/0152887 A1    May 14, 2020

(30) Foreign Application Priority Data
Dec. 28, 2016    (JP) .................... 2016-254916

(51) Int. Cl.
*H10K 85/60* (2023.01)
*C07D 491/048* (2006.01)
*H10K 50/11* (2023.01)
*H10K 101/00* (2023.01)
*H10K 101/10* (2023.01)
*H10K 101/30* (2023.01)

(52) U.S. Cl.
CPC ....... *H10K 85/657* (2023.02); *C07D 491/048* (2013.01); *H10K 85/6576* (2023.02); *H10K 50/11* (2023.02); *H10K 2101/10* (2023.02); *H10K 2101/30* (2023.02); *H10K 2101/90* (2023.02)

(58) Field of Classification Search
CPC ............ H01L 51/0071; H01L 51/0072; H01L 51/0073; H01L 51/0074; H01L 51/5016; H01L 51/5012; H10K 85/657; H10K 2101/90; H10K 2101/10
See application file for complete search history.

(56) References Cited

U.S. PATENT DOCUMENTS

| | | |
|---|---|---|
| 5,182,279 A | 1/1993 | Jorgensen et al. |
| 7,312,226 B2 | 12/2007 | Hurley et al. |
| 7,326,712 B2 | 2/2008 | Hurley et al. |
| 7,326,713 B2 | 2/2008 | Hurley et al. |
| 7,335,662 B2 | 2/2008 | Hurley et al. |
| 8,007,927 B2 | 8/2011 | Lin et al. |
| 8,221,905 B2 | 7/2012 | Lin et al. |
| 8,367,850 B2 | 2/2013 | Ma et al. |
| 8,415,031 B2 | 4/2013 | Xia et al. |
| 8,552,018 B2 | 10/2013 | Hurley et al. |
| 8,580,402 B2 | 11/2013 | Lin et al. |
| 8,586,204 B2 | 11/2013 | Xia et al. |
| 8,652,652 B2 | 2/2014 | Brooks et al. |
| 8,822,708 B2 | 9/2014 | Ma et al. |
| 8,866,377 B2 | 10/2014 | Adamovich et al. |
| 8,921,549 B2 | 12/2014 | Inoue et al. |
| 8,999,988 B2 | 4/2015 | Hurley et al. |
| 9,123,903 B2 | 9/2015 | Lin et al. |
| 9,153,786 B2 | 10/2015 | Ma et al. |
| 9,771,373 B2 | 9/2017 | Lee et al. |
| 9,853,218 B2 | 12/2017 | Asada et al. |
| 9,865,665 B2 | 1/2018 | Eguchi et al. |
| 9,917,257 B2 | 3/2018 | Lee et al. |
| 10,141,525 B2 | 11/2018 | Ito et al. |
| 10,586,931 B2 | 3/2020 | Kanamoto et al. |
| 10,622,426 B2 | 4/2020 | Eguchi et al. |
| 10,797,247 B2 | 10/2020 | Lee et al. |
| 11,008,280 B2 | 5/2021 | Mun et al. |
| 11,088,332 B2 | 8/2021 | Kanamoto et al. |

(Continued)

FOREIGN PATENT DOCUMENTS

| | | |
|---|---|---|
| CN | 104292241 A | 1/2015 |
| CN | 105884786 A | 8/2016 |

(Continued)

OTHER PUBLICATIONS

Katakura et al., Machine translation of JP 2011-084531 A (2011) pp. 1-80. (Year: 2011).*
Yoshida et al., Machine translation of JP 2015-078169 A (2015) pp. 1-19. (Year: 2015).*
International Search Report re Application No. PCT/IB2017/057977, dated Apr. 3, 2018.
Written Opinion re Application No. PCT/IB2017/057977, dated Apr. 3, 2018.
Chinese Office Action (Application No. 201780077212.1) Dated Jul. 5, 2021.
Taiwanese Office Action (Application No. 106144538) Dated Apr. 28, 2022.

*Primary Examiner* — Dylan C Kershner
(74) *Attorney, Agent, or Firm* — Husch Blackwell LLP

(57) ABSTRACT

A novel compound and a light-emitting element with high emission efficiency and a long lifetime are provided. The novel compound includes a benzofuropyrazine skeleton or a benzothienopyrazine skeleton, and each of a benzene ring and a pyrazine ring in the benzofuropyrazine skeleton or the benzothienopyrazine skeleton independently includes a substituent with a total number of carbon atoms of 6 to 100 inclusive. The light-emitting element includes the compound.

7 Claims, 20 Drawing Sheets

(56) References Cited

U.S. PATENT DOCUMENTS

| | | |
|---|---|---|
| 2006/0187381 A1 | 8/2006 | Yokozawa |
| 2008/0051414 A1 | 2/2008 | Hurley et al. |
| 2008/0269239 A1 | 10/2008 | Harris et al. |
| 2008/0314965 A1 | 12/2008 | Roberts et al. |
| 2009/0099165 A1 | 4/2009 | Hurley et al. |
| 2009/0143399 A1 | 6/2009 | Hurley et al. |
| 2009/0153034 A1 | 6/2009 | Lin et al. |
| 2009/0163545 A1 | 6/2009 | Goldfarb |
| 2010/0187984 A1 | 7/2010 | Lin et al. |
| 2011/0178107 A1 | 7/2011 | Wang et al. |
| 2012/0061654 A1 | 3/2012 | Rayabarapu et al. |
| 2013/0060037 A1 | 3/2013 | Lin et al. |
| 2013/0140549 A1 | 6/2013 | Xia et al. |
| 2014/0042413 A1 | 2/2014 | Xia et al. |
| 2014/0103327 A1 | 4/2014 | Brooks et al. |
| 2014/0254111 A1* | 9/2014 | Yamazaki ........... H01L 51/0097 361/749 |
| 2014/0284642 A1* | 9/2014 | Yamazaki ........... H01L 51/5275 257/98 |
| 2014/0291645 A1 | 10/2014 | Inoue et al. |
| 2015/0001524 A1 | 1/2015 | Brooks et al. |
| 2015/0021555 A1 | 1/2015 | Kwong et al. |
| 2015/0021556 A1 | 1/2015 | Xia et al. |
| 2015/0207082 A1 | 7/2015 | Dyatkin et al. |
| 2015/0317015 A1 | 11/2015 | Eguchi et al. |
| 2015/0333273 A1 | 11/2015 | Lee et al. |
| 2015/0351168 A1 | 12/2015 | Yasumoto et al. |
| 2015/0372243 A1 | 12/2015 | Ma et al. |
| 2015/0380673 A1 | 12/2015 | Ito et al. |
| 2017/0186971 A1 | 6/2017 | Kanamoto et al. |
| 2020/0024282 A1 | 1/2020 | Parham et al. |
| 2020/0028091 A1 | 1/2020 | Parham et al. |
| 2020/0243626 A1 | 7/2020 | Eguchi et al. |
| 2020/0295267 A1 | 9/2020 | Kanamoto et al. |

FOREIGN PATENT DOCUMENTS

| | | |
|---|---|---|
| CN | 107922311 A | 4/2018 |
| CN | 109689658 A | 4/2019 |
| CN | 109790173 A | 5/2019 |
| EP | 2 826 781 A1 | 1/2015 |
| EP | 3 326 998 A1 | 5/2018 |
| JP | 05-507468 | 10/1993 |
| JP | 2011-084531 A | 4/2011 |
| JP | 2013-536196 | 9/2013 |
| JP | 2014-131079 A | 7/2014 |
| JP | 2014-209611 A | 11/2014 |
| JP | 2015-021007 A | 2/2015 |
| JP | 2015-078169 A | 4/2015 |
| JP | 2015-151352 A | 8/2015 |
| JP | 2015-228367 A | 12/2015 |
| JP | 2016-027553 A | 2/2016 |
| JP | 2016-027559 A | 2/2016 |
| JP | 2018-531885 | 11/2018 |
| JP | 2019-532951 | 11/2019 |
| JP | 2019-532952 | 11/2019 |
| KR | 2015-0009462 A | 1/2015 |
| KR | 2015-0131564 A | 11/2015 |
| KR | 2015-0138072 A | 12/2015 |
| KR | 2016-0002384 A | 1/2016 |
| KR | 2017-0122121 A | 11/2017 |
| KR | 2019-0053948 A | 5/2019 |
| KR | 2019-0059949 A | 5/2019 |
| TW | 201406807 | 2/2014 |
| TW | 201613156 | 4/2016 |
| TW | 201827438 | 8/2018 |
| TW | 201829414 | 8/2018 |
| WO | WO 1991/016325 A1 | 10/1991 |
| WO | WO 2013/168927 A2 | 11/2013 |
| WO | WO 2017/188676 A1 | 11/2017 |
| WO | WO 2018/060218 A1 | 4/2018 |
| WO | WO 2018/060307 A1 | 4/2018 |
| WO | WO-2018/234917 | 12/2018 |

\* cited by examiner

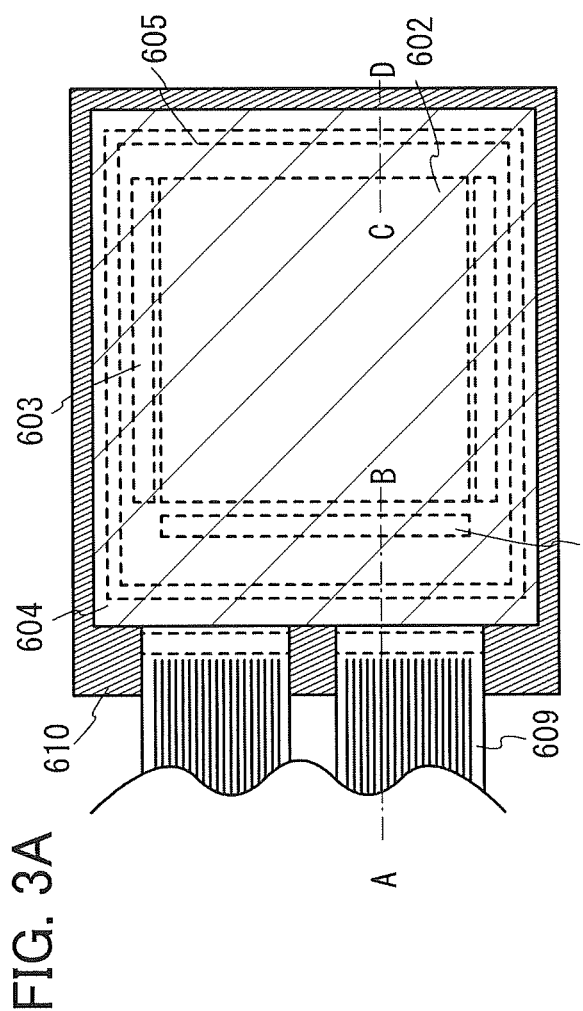
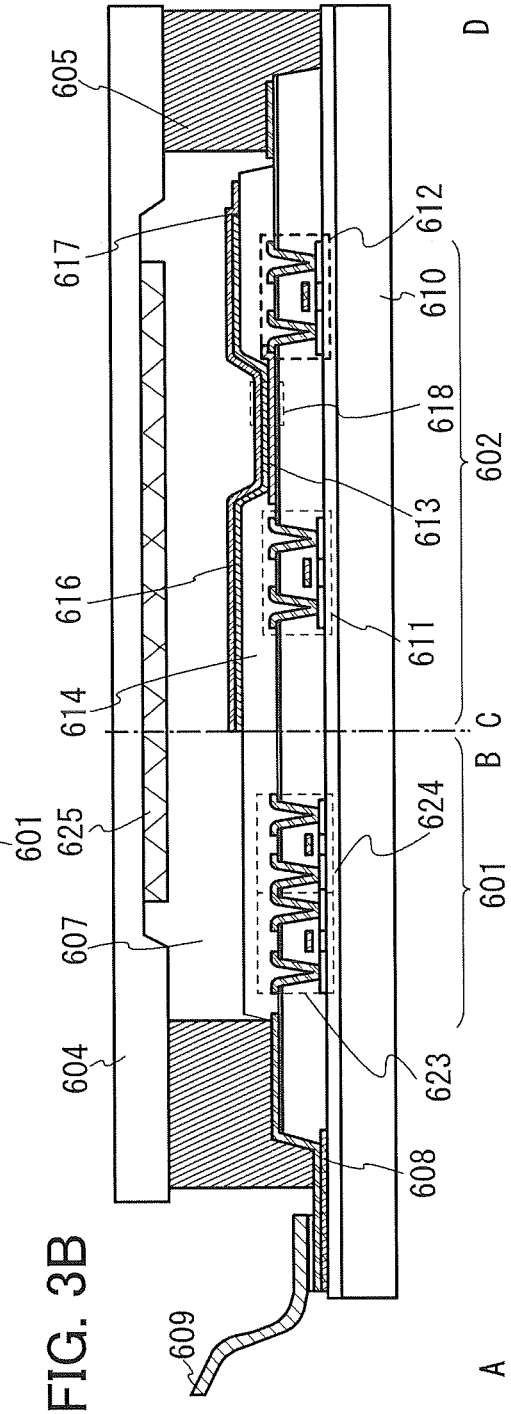
FIG. 3A
FIG. 3B

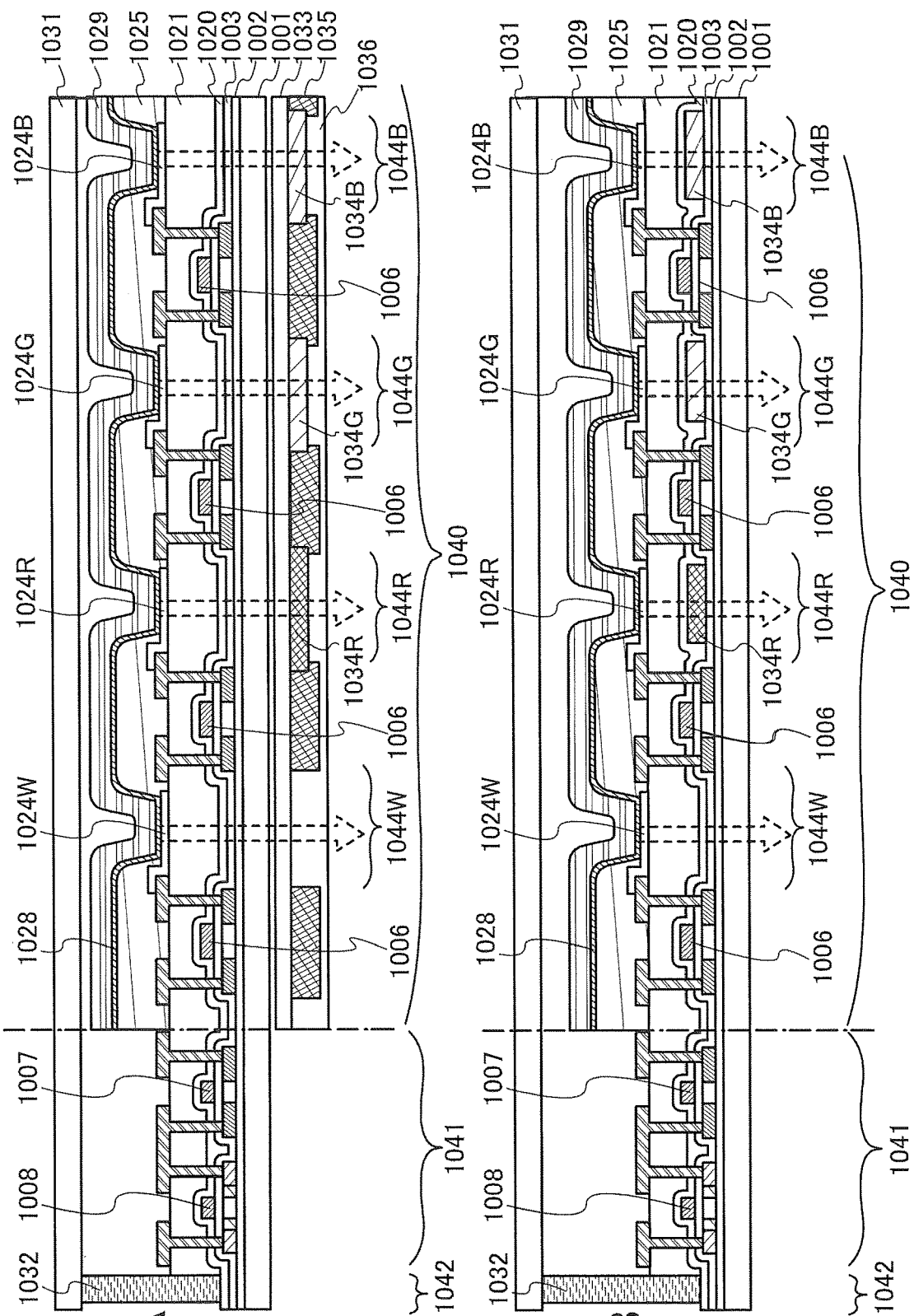

LIGHT-EMITTING ELEMENT, ORGANIC COMPOUND, LIGHT-EMITTING DEVICE, ELECTRONIC DEVICE, AND LIGHTING DEVICE

This application is a 371 of international application PCT/IB2017/057977 filed on Dec. 15, 2017 which is incorporated herein by reference.

TECHNICAL FIELD

One embodiment of the present invention relates to a light-emitting element including a benzofuropyrazine compound or a benzothienopyrazine compound. One embodiment of the present invention relates to a novel organic compound. One embodiment of the present invention relates to a benzofuropyrazine compound or a benzothienopyrazine compound. One embodiment of the present invention relates to a light-emitting device, an electronic device, and a lighting device each including the organic compound.

Note that one embodiment of the present invention is not limited to the above technical field. One embodiment of the present invention relates to an object, a method, or a manufacturing method. In addition, the present invention relates to a process, a machine, manufacture, or a composition of matter. In particular, one embodiment of the present invention relates to a semiconductor device, a light-emitting device, a display device, a lighting device, a light-emitting element, or a manufacturing method thereof. In addition, one embodiment of the present invention relates to a novel method for synthesizing a benzofuropyrazine compound or benzothienopyrazine compound including a π-electron rich heteroaromatic ring. Thus, specific examples of one embodiment of the present invention disclosed in this specification include a light-emitting element, a light-emitting device, an electronic device, and a lighting device, each of which includes the organic compound, and manufacturing methods of them.

BACKGROUND ART

Light-emitting elements (organic EL elements) including organic compounds and utilizing electroluminescence (EL) have been put to more practical use. In the basic structure of such a light-emitting element, an organic compound layer containing a light-emitting material (an electroluminescent (EL) layer) is provided between a pair of electrodes. Carriers are injected by application of voltage to the element, and light emission can be obtained from the light-emitting material by using the recombination energy of the carriers.

The light-emitting elements are self-luminous elements and thus have advantages such as high visibility and no need for backlight when used as pixels of a display, and are suitable as flat panel display elements. In addition, it is also a great advantage that a display including such light-emitting elements can be manufactured as a thin and lightweight display. Furthermore, an extremely high response speed is also a feature thereof.

In such light-emitting elements, light-emitting layers can be successively formed two-dimensionally, so that planar light emission can be obtained. This feature is difficult to obtain with point light sources typified by incandescent lamps and LEDs or linear light sources typified by fluorescent lamps. Furthermore, light emission from an organic compound can be light emission which does not include UV light by selecting a material; thus, light-emitting elements also have great potential as planar light sources used in lighting devices and the like.

Displays or lighting devices including light-emitting elements can be suitably used for a variety of electronic devices as described above; thus, research and development of light-emitting elements have progressed for higher efficiency or longer element lifetimes. In particular, an organic compound is mainly used in an EL layer and greatly affects an improvement in the characteristics of the light-emitting element. For this reason, a variety of novel organic compounds have been developed.

The lifetime and properties of a light-emitting element including an organic compound are greatly affected by the properties of a host material and an electron-transport material in some cases.

A variety of substances having a skeleton is used as host materials; in particular, a diazine skeleton has a high triplet excitation level and thus various compounds having a diazine skeleton have been reported. Light-emitting elements including these compounds have improved characteristics and reliability, but do not sufficiently meet a need for various high-level characteristics such as efficiency and resistance yet (e.g., Patent Documents 1 and 2).

REFERENCE

Patent Document

[Patent Document 1] Japanese Published Patent Application No. 2014-209611
[Patent Document 2] Japanese Translation of PCT International Application No. 2013-536196

DISCLOSURE OF INVENTION

In view of the above, an object of one embodiment of the present invention is to provide a novel organic compound. In particular, the object is to provide a novel benzofuropyrazine compound or a novel benzothienopyrazine compound. Another object of one embodiment of the present invention is to provide a novel organic compound having an electron-transport property. Another object of one embodiment of the present invention is to provide a highly reliable light-emitting element. Another object of one embodiment of the present invention is to provide a light-emitting element with high emission efficiency. Another object of one embodiment of the present invention is to provide a light-emitting element driven at a low voltage.

Another object of one embodiment of the present invention is to provide a light-emitting element, a light-emitting device, and an electronic device each having high reliability. Another object of one embodiment of the present invention is to provide a light-emitting element, a light-emitting device, and an electronic device each with low power consumption.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a light-emitting element including an EL layer between a pair of electrodes. The EL layer contains a substance including a benzofuropyrazine skeleton or a benzothienopyrazine skeleton. A benzene ring in the benzofuropyrazine skeleton or the benzothienopyrazine skeleton includes a first substituent with a total number of carbon atoms of 6 to 100 inclusive. A pyrazine ring in the benzofuropyrazine skeleton or the benzothienopyrazine skeleton includes a second substituent with a total number of carbon atoms of 6 to 100 inclusive.

Another embodiment of the present invention is a light-emitting element including an EL layer between a pair of electrodes. The EL layer contains a substance including a benzofuropyrazine skeleton or a substance including a benzothienopyrazine skeleton. A benzene ring in the benzofuropyrazine skeleton or a benzene ring in the benzothienopyrazine skeleton includes a first substituent with a total number of carbon atoms of 10 to 100 inclusive. A pyrazine ring in the benzofuropyrazine skeleton or a pyrazine ring in the benzothienopyrazine skeleton includes a second substituent with a total number of carbon atoms of 10 to 100 inclusive. At this time, it is preferable that each of the first substituent and the second substituent independently include an aromatic ring having 10 to 30 carbon atoms or a heteroaromatic ring having 10 to 30 carbon atoms.

In the above structure, it is preferable that each of the first substituent and the second substituent independently include at least one of a substituted or unsubstituted benzene ring, a substituted or unsubstituted naphthalene ring, a substituted or unsubstituted phenanthrene ring, a substituted or unsubstituted triphenylene ring, a substituted or unsubstituted condensed heteroaromatic ring having 12 to 30 carbon atoms, and a substituted or unsubstituted triarylamine structure, and that the condensed heteroaromatic ring include any one of a dibenzofuran ring, a dibenzothiophene ring, and a carbazole ring.

In the above structure, it is preferable that the second substituent include a skeleton having a hole-transport property. The skeleton having a hole-transport property preferably has a triarylamine structure or includes a π-electron rich heteroaromatic ring. The skeleton having a hole-transport property is preferably a condensed heteroaromatic ring including any one of a carbazole ring, a dibenzofuran ring, and a dibenzothiophene ring.

It is preferable that the EL layer include a light-emitting layer, and that the light-emitting layer contain a substance including the benzofuropyrazine skeleton or the benzothienopyrazine skeleton and a substance capable of converting triplex excitation energy into light emission. This structure is particularly effective in the case where the substance capable of converting triplet excitation energy into light emission is a phosphorescent compound.

Another embodiment of the present invention is an organic compound represented by General Formula (G0) below.

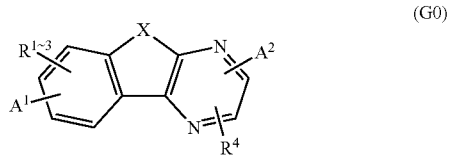

(G0)

In General Formula (G0), X represents oxygen or sulfur; each of $A^1$ and $A^2$ independently represents a substituent having 6 to 100 carbon atoms; and each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

In General Formula (G0), it is preferable that each of $A^1$ and $A^2$ independently represent a substituent having 10 to 100 carbon atoms. At this time, it is preferable that each of the $A^1$ and the $A^2$ independently include an aromatic ring having 10 to 30 carbon atoms or a heteroaromatic ring having 10 to 30 carbon atoms.

In the compound represented by General Formula (G0) shown above, it is more preferable that each of $A^1$ and $A^2$ independently include at least one of a substituted or unsubstituted benzene ring, a substituted or unsubstituted naphthalene ring, a substituted or unsubstituted phenanthrene ring, a substituted or unsubstituted triphenylene ring, a substituted or unsubstituted condensed heteroaromatic ring having 12 to 30 carbon atoms, and a substituted or unsubstituted triphenylamine structure. The condensed heteroaromatic ring preferably includes any one of a dibenzofuran ring, a dibenzothiophene ring, and a carbazole ring.

In the above structure, $A^2$ preferably includes a condensed heteroaromatic ring including any one of a carbazole ring, a dibenzofuran ring, and a dibenzothiophene ring.

Another embodiment of the present invention is an organic compound represented by General Formula (G1) below.

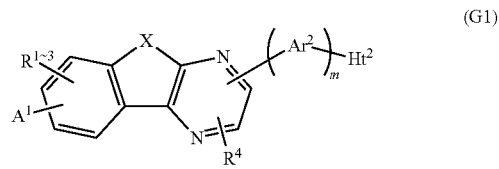

(G1)

In General Formula (G1), X represents oxygen or sulfur; $A^1$ represents a substituent having a total number of carbon atoms of 6 to 100 inclusive; $Ht^2$ represents a substituted or unsubstituted aromatic ring having 10 to 30 carbon atoms or a substituted or unsubstituted heteroaromatic ring having 10 to 30 carbon atoms; $Ar^2$ represents a substituted or unsubstituted arylene group having 6 to 25 carbon atoms; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and m represents an integer of 0 to 3.

In the above structure, $A^1$ is preferably a substituent with a total number of carbon atoms of 10 to 100 inclusive.

$Ht^2$ is preferably a substituted or unsubstituted condensed heteroaromatic ring including any one of a carbazole ring, a dibenzofuran ring, and a dibenzothiophene ring.

Another embodiment of the present invention is an organic compound represented by General Formula (G2) below.

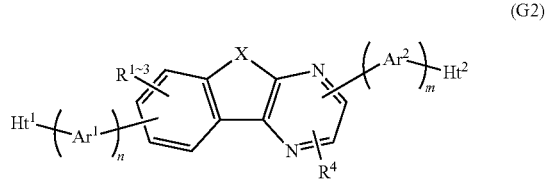

(G2)

In General Formula (G2), X represents oxygen or sulfur; each of $Ht^1$ and $Ht^2$ independently represents an aromatic ring having 10 to 30 carbon atoms or a heteroaromatic ring having 10 to 30 carbon atoms; each of $Ar^1$ and $Ar^2$ independently represents a substituted or unsubstituted arylene group having 6 to 25 carbon atoms; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and each of n and m independently represents an integer of 0 to 3.

In the above structure, it is preferable that each of $Ht^1$ and $Ht^2$ independently represents a substituted or unsubstituted condensed heteroaromatic ring including any one of a carbazole ring, a dibenzofuran ring, and a dibenzothiophene ring.

In the above structure, it is preferable that $Ar^1$ or $Ar^2$ represent a substituted or unsubstituted phenylene group, and that all of $R^1$ to $R^4$ be hydrogen.

Another embodiment of the present invention is an organic compound represented by General Formula (G3) below.

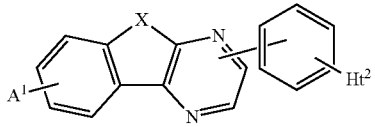
(G3)

In General Formula (G3), X represents oxygen or sulfur; $A^1$ represents a substituent with a total number of carbon atoms of 10 to 100 inclusive; and $Ht^2$ represents a substituted or unsubstituted heteroaromatic ring including any one of a carbazole ring, a dibenzofuran ring, and a dibenzothiophene ring.

Another embodiment of the present invention is an organic compound represented by General Formula (G4) below.

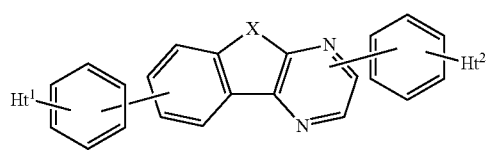
(G4)

In General Formula (G4), X represents oxygen or sulfur; and each of $Ht^1$ and $Ht^2$ independently represents a substituted or unsubstituted heteroaromatic ring including any one of a carbazole ring, a dibenzofuran ring, and a dibenzothiophene ring.

In the above structure, it is preferable that each of $Ht^1$ and $Ht^2$ independently represent any one of groups represented by General Formulae (Ht-1) to (Ht-7).

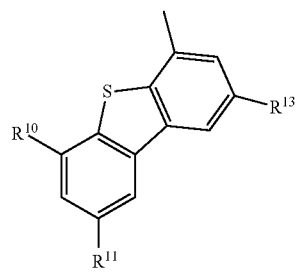
(Ht-1)

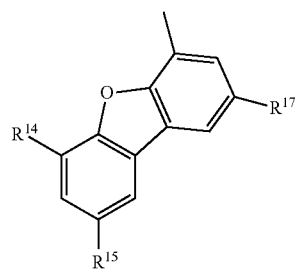
(Ht-2)

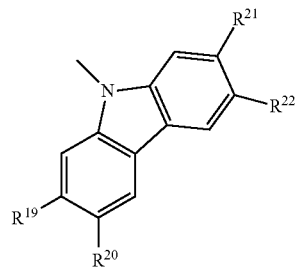
(Ht-3)

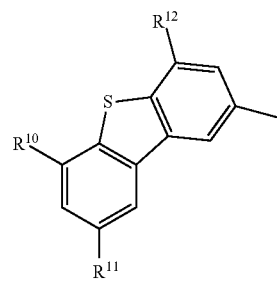
(Ht-4)

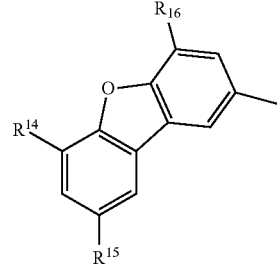
(Ht-5)

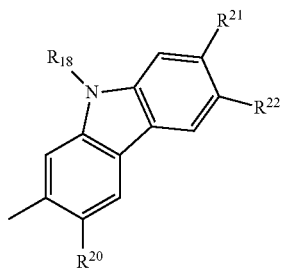

(Ht-6)

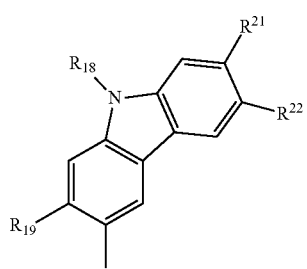

(Ht-7)

In General Formulae (Ht-1) to (Ht-7), each of $R^{10}$ to $R^{22}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 25 carbon atoms.

Another embodiment of the present invention is an organic compound represented by General Formula (G5) below.

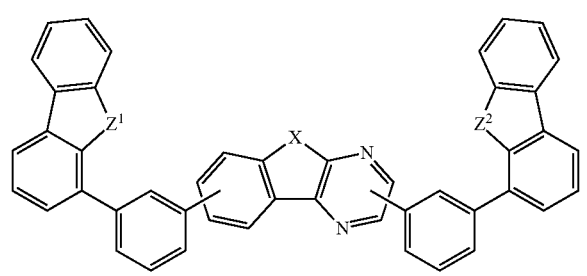

(G5)

In General Formula (G5), X represents oxygen or sulfur; and each of $Z^1$ and $Z^2$ independently represents oxygen or sulfur.

Another embodiment of the present invention is an organic compound represented by Structural Formula (100) or Structural Formula (101).

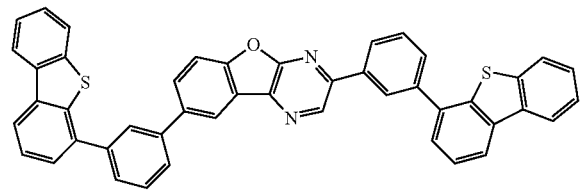

(100)

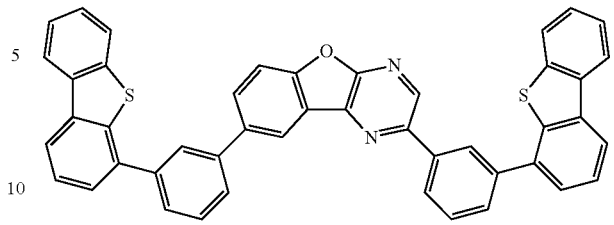

(101)

Another embodiment of the present invention is a light-emitting element that contains any of the above-described organic compounds.

The light-emitting element in the above embodiment includes an EL layer between an anode and a cathode. The EL layer includes at least one of a light-emitting layer, a hole-transport layer, a hole-injection layer, an electron-transport layer, and an electron-injection layer. Note that the EL layer may include another functional layer.

In the above embodiment, the light-emitting layer preferably contains a light-emitting material.

Another embodiment of the present invention is a display device including the light-emitting element having any of the above structures, and at least one of a color filter and a transistor. Another embodiment of the present invention is an electronic device including the display device, and at least one of a housing and a touch sensor. Another embodiment of the present invention is a lighting device including the light-emitting element having any of the above-described structures, and at least one of a housing and a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). A display module in which a connector such as a flexible printed circuit (FPC) or a tape carrier package (TCP) is connected to a light-emitting device, a display module in which a printed wiring board is provided on the tip of a TCP, and a display module in which an integrated circuit (IC) is directly mounted on a light-emitting element by a chip on glass (COG) method are also embodiments of the present invention.

According to one embodiment of the present invention, a novel organic compound can be provided. In particular, a novel benzofuropyrazine compound or a novel benzothienopyrazine compound can be provided. A novel organic compound having an electron-transport property can be provided. A light-emitting element having a long lifetime can be provided. A light-emitting element with high emission efficiency can be provided. A light-emitting element driven at a low voltage can be provided. A light-emitting element, a light-emitting device, and an electronic device each having high reliability can be provided. A light-emitting element, a light-emitting device, and an electronic device each having low power consumption can be provided.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF DRAWINGS

FIGS. 3A and 3B are conceptual diagrams illustrating an active matrix light-emitting device of one embodiment of the present invention.

FIGS. 4A and 4B are conceptual diagrams illustrating an active matrix light-emitting device of one embodiment of the present invention.

BEST MODE FOR CARRYING OUT THE INVENTION

Figure 1A:
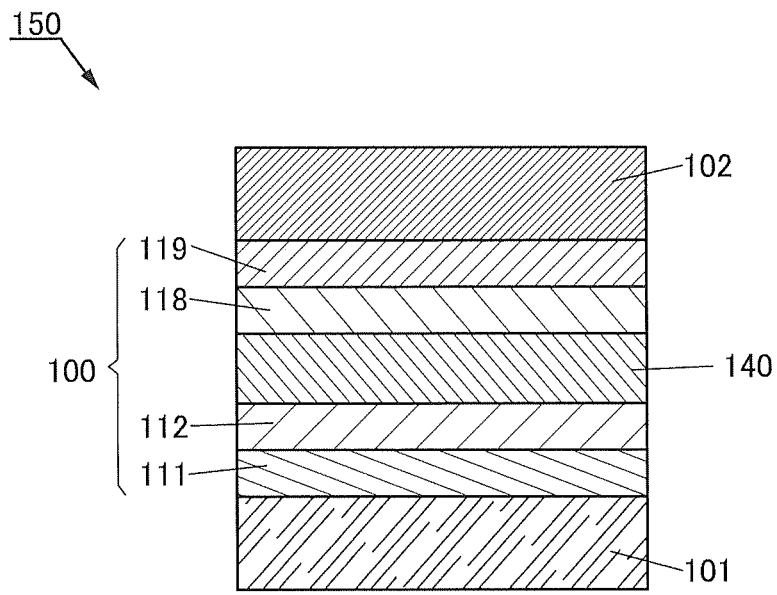
FIGS. 1A and 1B are schematic cross-sectional views illustrating a light-emitting element of one embodiment of the present invention and FIG. 1C is a schematic diagram illustrating the correlation of energy levels in a light-emitting layer.

Embodiments of the present invention will be described below. Note that it is easily understood by those skilled in the art that modes and details disclosed herein can be modified in various ways without departing from the spirit and scope of the present invention. Therefore, the present invention is not construed as being limited to the description of the following embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as those which specify one embodiment of the present invention.

In the structures of the present invention described in this specification and the like, the same portions or portions having similar functions in different drawings are denoted by the same reference numerals, and description of such portions is not repeated. Furthermore, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that in this specification, the terms "film" and "layer" can be interchanged with each other depending on the case or circumstances. For example, the term "conductive layer" can be changed into the term "conductive film" in some cases, and the term "insulating film" can be changed into the term "insulating layer" in some cases.

Embodiment 1

In this embodiment, an organic compound and a light-emitting element of embodiments of the present invention are described below, for example.

The organic compound of one embodiment of the present invention is represented by General Formula (G0) below.

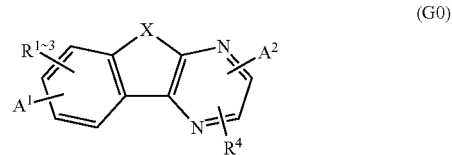

(G0)

In General Formula (G0), X represents oxygen or sulfur, each of $A^1$ and $A^2$ independently represents a substituent having 6 to 100 carbon atoms. Each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

A light-emitting element including such an organic compound has high emission efficiency and is driven at a low voltage. Since the organic compound has high resistance to repetition of oxidation and reduction and a stable excited state, the light-emitting element including the organic compound can have high reliability.

Since $A^1$ has a total number of carbon atoms of 6 to 100 inclusive, the light-emitting element has greatly improved reliability as compared with a light-emitting element with a structure in which all of $A^1$ and $R^1$ to $R^3$ are hydrogen. This is noticeable particularly when the organic compound represented by General Formula (G0) is used as a host material in a light-emitting layer. This is probably because the substituent included in a benzene ring side in a benzofuropyrazine skeleton or a benzothienopyrazine skeleton improves the stability of an excited state of the organic compound and the stability of film quality. The fact that the substituent in an aromatic ring on the opposite side of a heteroaromatic ring (e.g., a pyrazine ring) brings the effect of increasing the reliability is a major breakthrough by the present inventors. In addition, since $A^2$ on the pyrazine side is a second substituent that also has a total number of carbon atoms of 6 to 100 inclusive as shown in General Formula (G0), carbon and nitrogen of the pyrazine ring are easily protected, so that the electrical stability when electrons are transported and the stability in an excited state can be increased. In the case where $A^2$ includes an aromatic ring or a heteroaromatic ring, a lowest unoccupied molecular orbital (also referred to as LUMO) is expanded by the interaction with the pyrazine ring, which gives the advantage in an electron-transport property. Therefore, it is preferable that the organic compound include the both substituents, $A^1$ and $A^2$.

An organic compound of one embodiment of the present invention is the organic compound represented by General Formula (G0). In General Formula (G0), X represents oxygen or sulfur, each of $A^1$ and $A^2$ independently represents a substituent having 10 to 100 carbon atoms. Each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms.

Since each of $A^1$ and $A^2$ is independently a substituent with a total number of carbon atoms of 10 to 100 inclusive, a molecular structure with high heat resistance can be achieved, which is preferable. It is important that not only heat resistance, but also the stability in an excited state, the stability of film quality, and the electrical stability when electrons are transported be further improved. A typical example of a substituent having 6 carbon atoms is a benzene ring (a phenyl group) or a substituent with a size similar to that of the benzene ring. For example, by replacing this substituent with a substituent which includes a condensed aromatic ring or a condensed heteroaromatic ring and has 10 or more carbon atoms, the above-described effect becomes more significant.

Accordingly, in General Formulae (G0) to (G4) shown above or below, each of $A^1$ and $A^2$ preferably includes a substituted or unsubstituted aromatic ring having 10 to 30 carbon atoms or a substituted or unsubstituted heteroaromatic ring having 10 to 30 carbon atoms. With such a structure, t conjugated systems can spread across the entire molecule and a molecular structure having a high carrier-transport property can be achieved, so that a highly reliable light-emitting element driven at a low voltage can be provided. Furthermore, this structure is effective in improving the electrochemical stability and the film quality, leading to an improvement in the reliability of the light-emitting element. Moreover, the molecular weight can be increased without decreasing a sublimation property, so that a material with high heat resistance can be provided. Thus, a molecular structure in which a bulky substituent with a total number of carbon atoms of greater than or equal to 10 is included in each of the benzene ring side and the pyrazine ring side in the benzofuropyrazine skeleton or the benzothienopyrazine skeleton is an important structure of one embodiment of the present invention.

In the above structure, examples of the substituted or unsubstituted aromatic ring having 10 to 30 carbon atoms and the substituted or unsubstituted heteroaromatic ring having 10 to 30 carbon atoms include a substituent including a plurality of benzene rings, and condensed aromatic rings such as a naphthalene ring, a fluorene ring, a phenanthrene ring, and a triphenylene ring. Other examples include a condensed heteroaromatic ring including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring).

Note that the substituent having 6 to 100 carbon atoms may include the substituted or unsubstituted aromatic ring, heteroaromatic ring, condensed aromatic ring, or condensed heteroaromatic ring having 10 to 30 carbon atoms, and may include a benzene ring. That is, the substituted or unsubstituted condensed aromatic ring, the substituted or unsubstituted condensed heteroaromatic ring, and a substituted or unsubstituted benzene ring may be combined. For example, the condensed heteroaromatic ring may be bonded to the benzofuropyrazine skeleton or the benzothienopyrazine skeleton through a phenylene group or a biphenyldiyl group.

In General Formulae (G0) to (G4) shown above or below, it is more preferable that each of $A^1$ and $A^2$ independently include at least one of a substituted or unsubstituted benzene ring, a substituted or unsubstituted naphthalene ring, a substituted or unsubstituted phenanthrene ring, a substituted or unsubstituted triphenylene ring, a substituted or unsubstituted condensed heteroaromatic ring having 12 to 30 carbon atoms, and a substituted or unsubstituted triarylamine structure. This structure facilitates synthesis. Light-emitting elements including these substituents can have high reliability because these substituents have high electrochemical stability. In the above structure, the condensed heteroaromatic ring is preferably a ring including a dibenzofuran ring, a dibenzothiophene ring, or a carbazole ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) in view of the stability and heat resistance of the ring. The triarylamine structure is preferably a triphenylamine structure, in which case the T1 level is increased. Note that the number of six-membered heteroaromatic rings having a lone electron-pair, such as pyridine rings, is too large in $A^1$ and $A^2$, the organic compound serves as a strong base in the excited state and has low reliability. Therefore, each of $A^1$ and $A^2$ is preferably formed with one or more of the above-described rings and structure.

An organic compound of one embodiment of the present invention is represented by General Formula (G1) below.

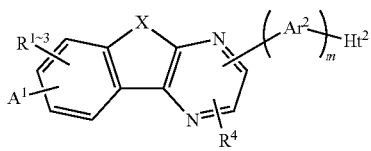

(G1)

In General Formula (G1), X represents oxygen or sulfur; $A^1$ represents a substituent having a total number of carbon atoms of 6 to 100 inclusive; $Ht^2$ represents a substituted or unsubstituted aromatic ring having 10 to 30 carbon atoms or a substituted or unsubstituted heteroaromatic ring having 10 to 30 carbon atoms; $Ar^2$ represents a substituted or unsubstituted arylene group having 6 to 25 carbon atoms; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and m represents an integer of 0 to 3.

In the above structure, $Ht^2$ preferably includes a skeleton having a hole-transport property. Since the benzofuropyrazine skeleton or the benzothienopyrazine skeleton includes the skeleton having a hole-transport property, a highly reliable light-emitting element having high oxidation-reduction characteristics can be provided. Furthermore, the carrier (electrons and holes) transport property is improved, so that the light-emitting element can be driven at a low voltage. In particular, $Ht^2$ is preferably a substituted or unsubstituted condensed heteroaromatic ring including any one of a carbazole ring, a dibenzofuran ring, and a dibenzothiophene ring. An organic compound with such a structure is stable in an excited state and has heat resistance and a high T1 level can be achieved.

An organic compound of one embodiment of the present invention is represented by General Formula (G2) below.

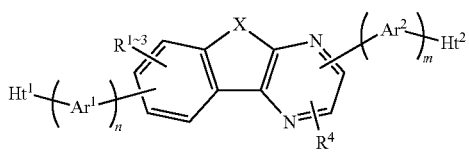

(G2)

In General Formula (G2), X represents oxygen or sulfur; each of $Ht^1$ and $Ht^2$ independently represents an aromatic ring having 10 to 30 carbon atoms or a heteroaromatic ring having 10 to 30 carbon atoms; each of $Ar^1$ and $Ar^2$ independently represents a substituted or unsubstituted arylene group having 6 to 25 carbon atoms; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and each of n and m independently represents an integer of 0 to 3.

In the above structure, it is preferable that $Ar^1$ or $Ar^2$ represent a substituted or unsubstituted phenylene group, and that all of $R^1$ to $R^4$ be hydrogen. Such a structure facilitates synthesis.

In the above structure, it is preferable that each of $Ht^1$ and $Ht^2$ be independently a substituted or unsubstituted condensed heteroaromatic ring including any one of a carbazole ring, a dibenzofuran ring, and a dibenzothiophene ring. An organic compound with such a structure is stable in an excited state and has heat resistance and a high T1 level can be achieved.

An organic compound of one embodiment of the present invention is represented by General Formula (G3) below.

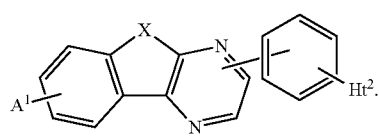

(G3)

In General Formula (G3), X represents oxygen or sulfur; $A^1$ represents a substituent with a total number of carbon atoms of 10 to 100 inclusive; and $Ht^2$ represents a substituted or unsubstituted heteroaromatic ring including any one of a carbazole ring, a dibenzofuran ring, and a dibenzothiophene ring.

An organic compound of one embodiment of the present invention is represented by General Formula (G4) below.

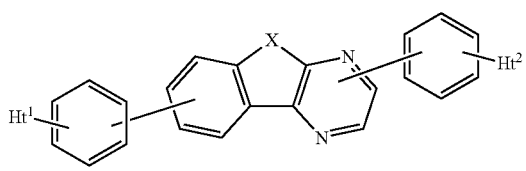

(G4)

In General Formula (G4), X represents oxygen or sulfur; and each of $Ht^1$ and $Ht^2$ independently represents a substituted or unsubstituted heteroaromatic ring including any one of a carbazole ring, a dibenzofuran ring, and a dibenzothiophene ring. An organic compound with such a structure is stable in an excited state and has heat resistance and a high T1 level can be achieved.

In the above structure, the benzofuropyrazine skeleton or the benzothienopyrazine skeleton and each of $Ht^1$ and $Ht^2$ are bonded at the meta position through a phenyl group. With such a structure, a structure with a high T1 level can be achieved. Furthermore, a structure in which a film is unlikely to be crystallized can be achieved. Note that the bonding position between the benzofuropyrazine skeleton or the benzothienopyrazine skeleton and each of $Ht^1$ and $Ht^2$ through a phenyl group is not limited to the meta position.

In the above structure, it is preferable that each of $Ht^1$ and $Ht^2$ be represented by any of General Formulae (Ht-1) to (Ht-7). With use of the substituent, an electrochemically stable structure with a high T1 level can be achieved.

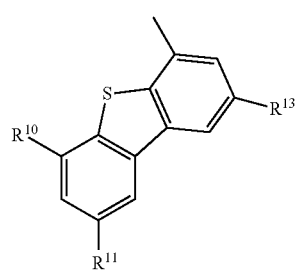

(Ht-1)

(Ht-2)

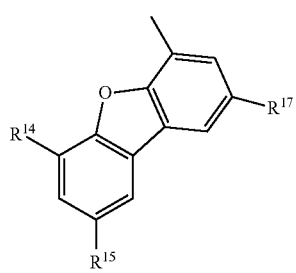

(Ht-3)

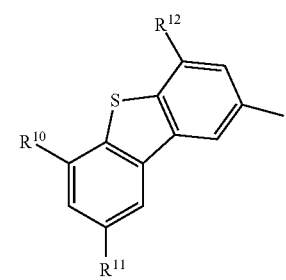

(Ht-4)

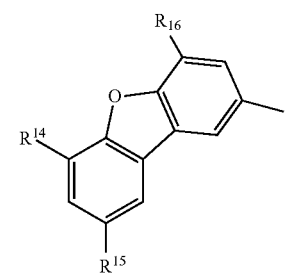

(Ht-5)

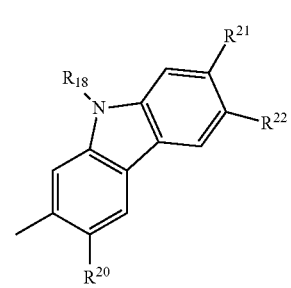

(Ht-6)

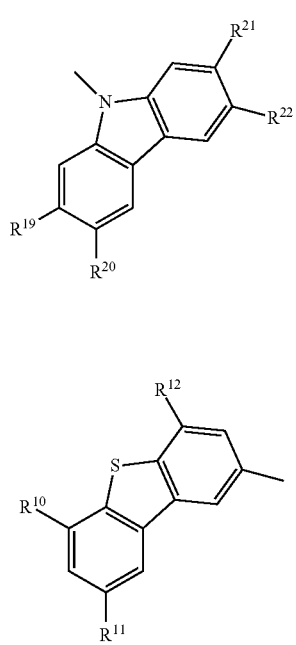

(Ht-7)

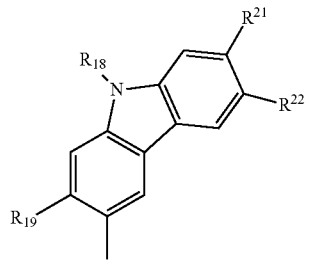

An organic compound of one embodiment of the present invention is represented by General Formula (G5) below.

(G5)

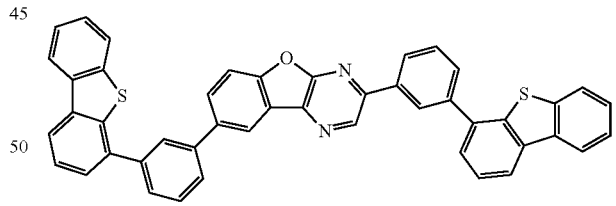

In General Formula (G5), X represents oxygen or sulfur; and each of $Z^1$ and $Z^2$ independently represents oxygen or sulfur.

The benzofuropyrazine skeleton or the benzothienopyrazine skeleton and a dibenzofuran skeleton or a dibenzothiophene skeleton are preferably bonded at the meta position through a phenyl group, in which case a structure with a high T1 level can be achieved.

An organic compound of one embodiment of the present invention is represented by Structural Formula (100) or Structural Formula (101) below.

(100)

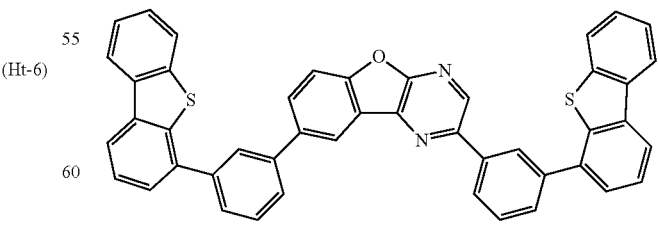

(101)

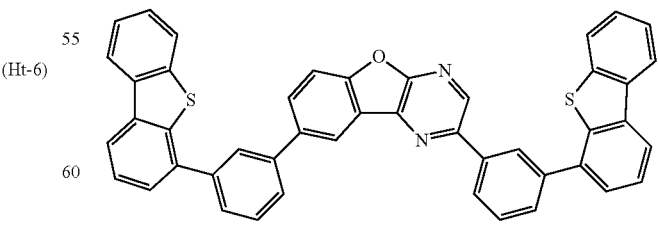

In General Formulae (G1) and (G2), each of $Ar^1$ and $Ar^2$ independently represents a substituted or unsubstituted arylene group having 6 to 25 carbon atoms, and examples of the arylene group include a phenylene group, a naphthylene group, a biphenyldiyl group, a fluorenediyl group, and a spirofluorenediyl group. For example, groups represented by Structural Formulae (Ar-1) to (Ar-27) shown below can be used. Note that the groups represented by $Ar^1$ and $Ar^2$ are not limited to these and may further include a substituent.
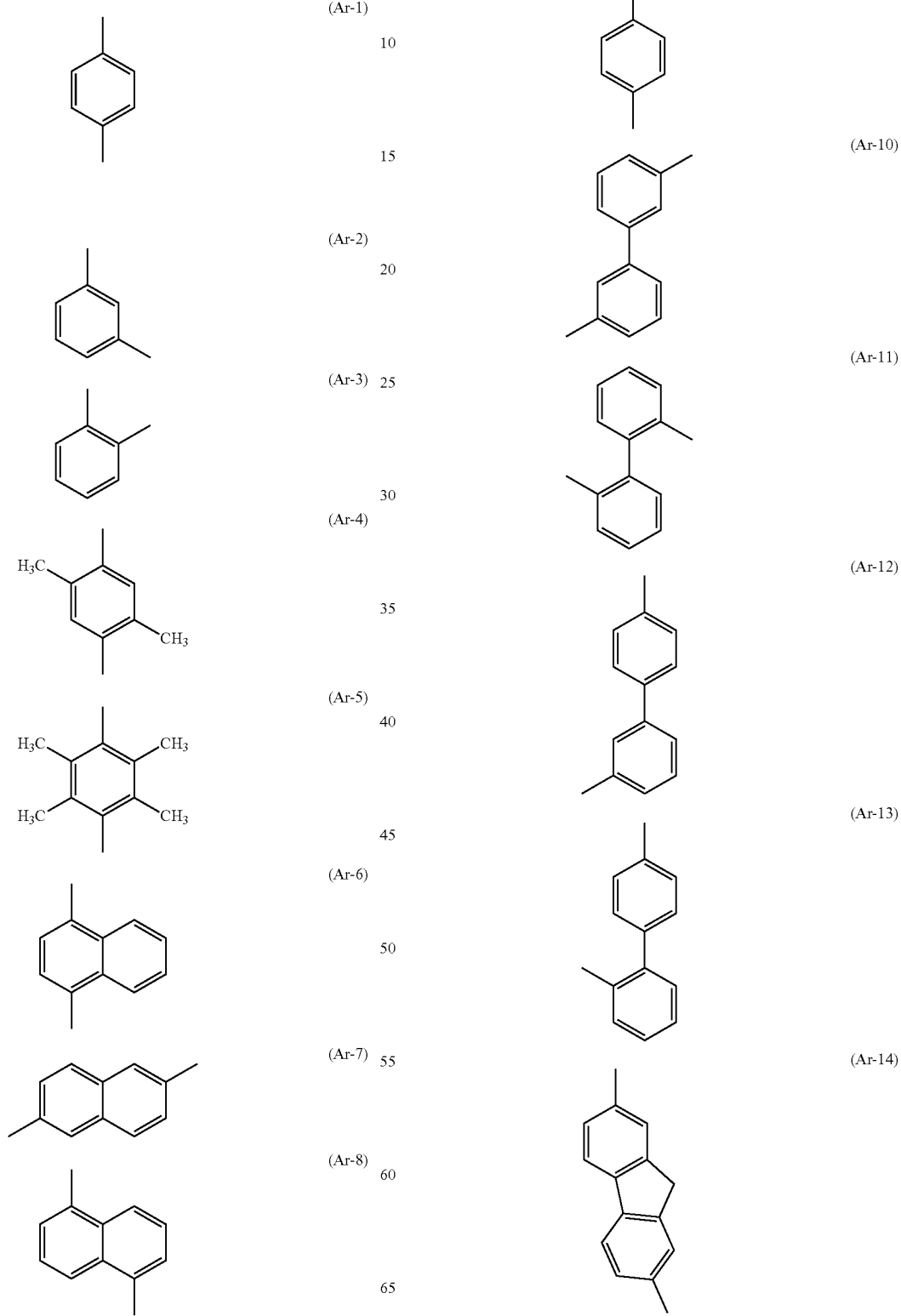

(Ar-15)
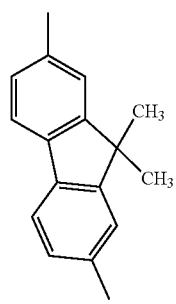
(Ar-16)
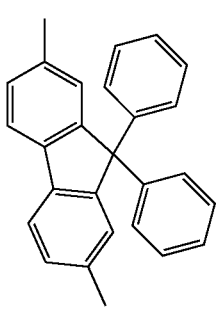
(Ar-17)
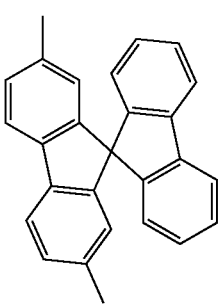
(Ar-18)
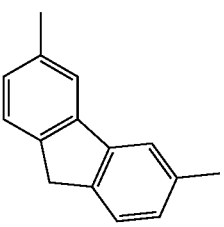
(Ar-19)
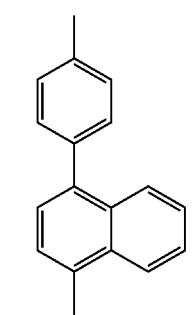
(Ar-20)
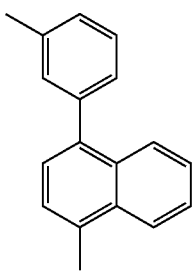
(Ar-21)
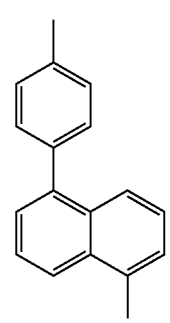
(Ar-22)
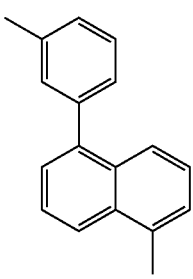
(Ar-23)
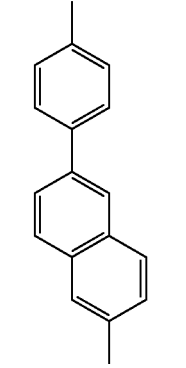
(Ar-24)
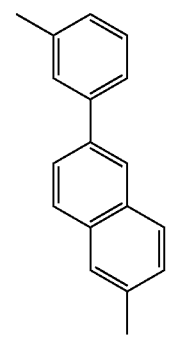

(Ar-25)
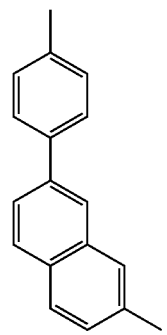

(Ar-26)
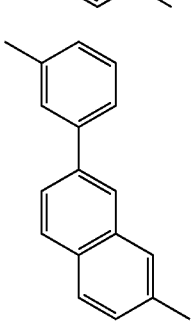

(Ar-27)
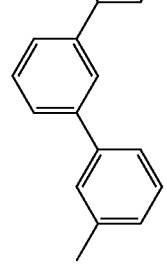

In General Formulae (G0) to (G2) and General Formulae (Ht-1) to (Ht-7), each of $R^1$ to $R^4$ and $R^{10}$ to $R^{22}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group. Specific examples of the cycloalkyl group include a cyclopropyl group, a cyclobutyl group, a cyclopentyl group, and a cyclohexyl group. Specific examples of the aryl group include a phenyl group, a naphthyl group, a biphenyl group, a fluorenyl group, and a spirofluorenyl group. More specific examples are groups represented by Structural Formulae (R-1) to (R-32). Note that the groups represented by $R^1$ to $R^4$ and $R^{10}$ to $R^{22}$ are not limited to these.

(R-1)

(R-2)

(R-3)
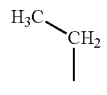

(R-4)
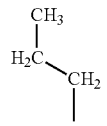

(R-5)
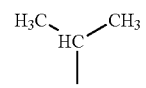

(R-6)
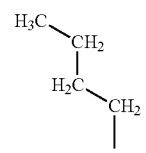

(R-7)
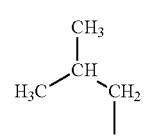

(R-8)
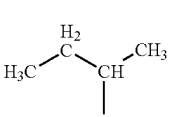

(R-9)
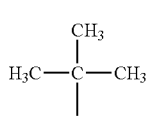

(R-10)
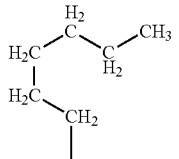

(R-11)
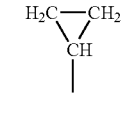

(R-12)
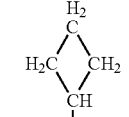

(R-13)
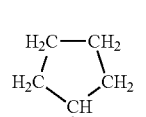

-continued
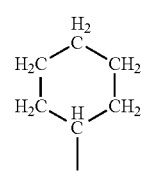 (R-14)
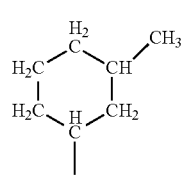 (R-15)
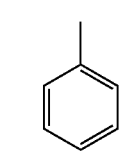 (R-16)
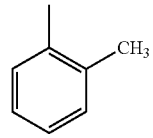 (R-17)
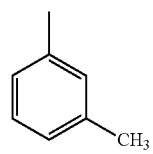 (R-18)
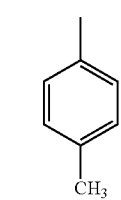 (R-19)
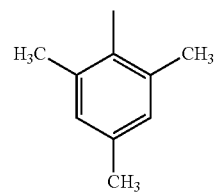 (R-20)
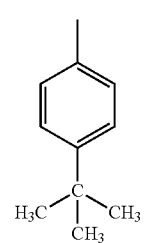 (R-21)
-continued
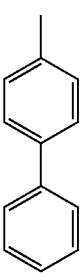 (R-22)
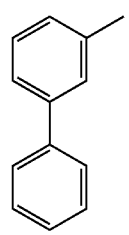 (R-23)
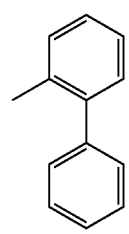 (R-24)
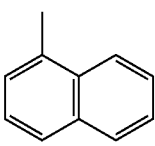 (R-25)
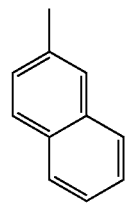 (R-26)
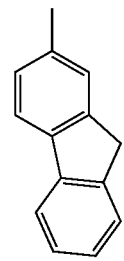 (R-27)
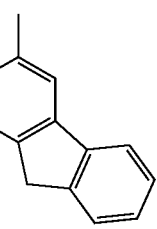 (R-28)

(R-29)
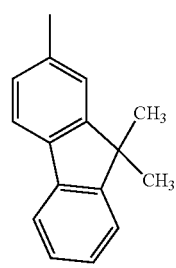

(R-30)
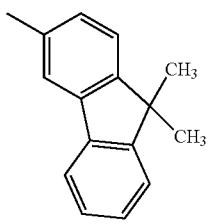

(R-31)
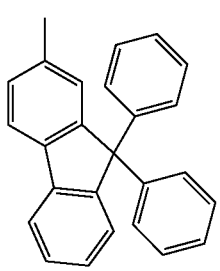

(R-32)
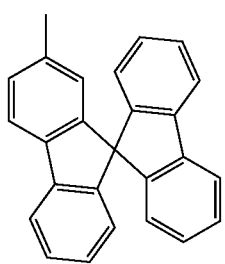

Note that in the above-described organic compound of one embodiment of the present invention, in the case where $A^1$, $A^2$, $Ht^1$, $Ht^2$, $R^1$ to $R^4$, and $R^{10}$ to $R^{22}$ have substituents, examples of the substituents include an alkyl group having 1 to 6 carbon atoms, a substituted or unsubstituted cycloalkyl group having 3 to 7 carbon atoms, and a substituted or unsubstituted aryl group having 6 to 25 carbon atoms. Specific examples of the alkyl group include a methyl group, an ethyl group, a propyl group, an isopropyl group, a butyl group, an isobutyl group, a tert-butyl group, and an n-hexyl group. Specific examples of the cycloalkyl group include a cyclopropyl group, a cyclobutyl group, a cyclopentyl group, and a cyclohexyl group. Specific examples of the aryl group include a phenyl group, a naphthyl group, a biphenyl group, a fluorenyl group, and a spirofluorenyl group.

<Specific Examples of Compounds>

Specific examples of structures of the compounds represented by General Formulae (G0) to (G5) include compounds represented by Structural Formulae (100) to (267). Note that the compounds represented by General Formulae (G0) to (G5) are not limited to the following examples.

(100)
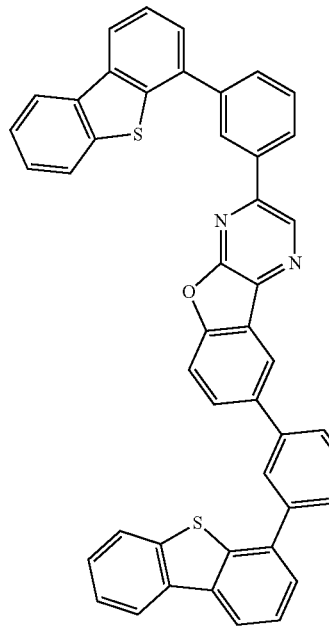

(101)
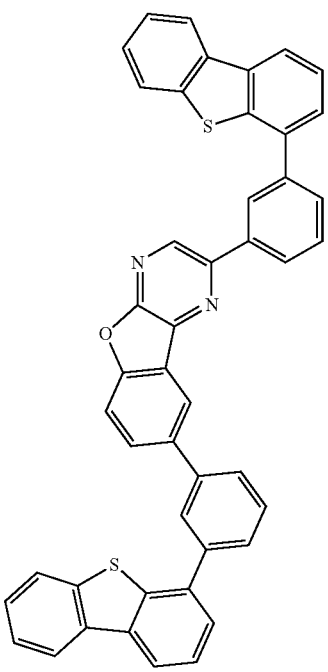

(102)
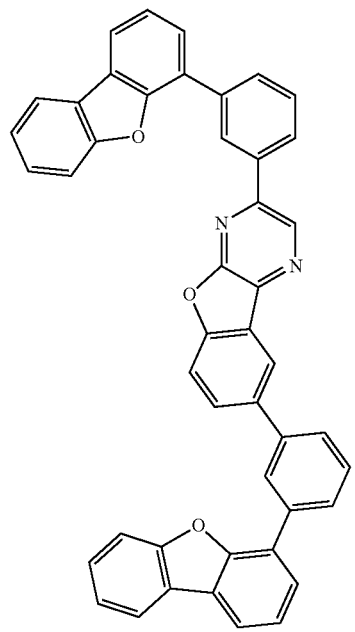
(104)
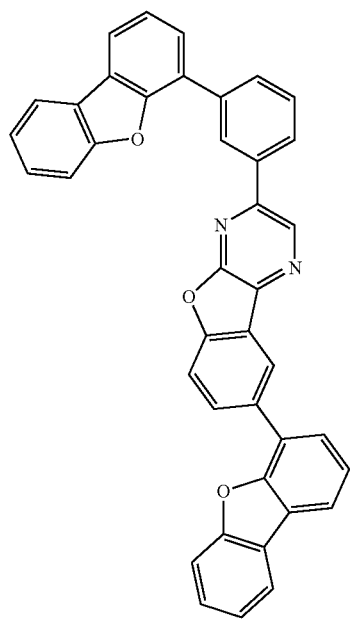
(103)
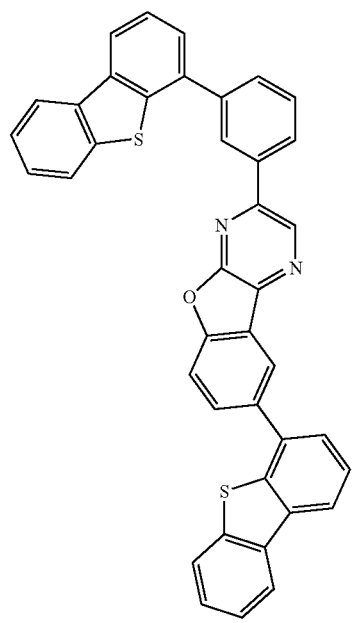
(105)
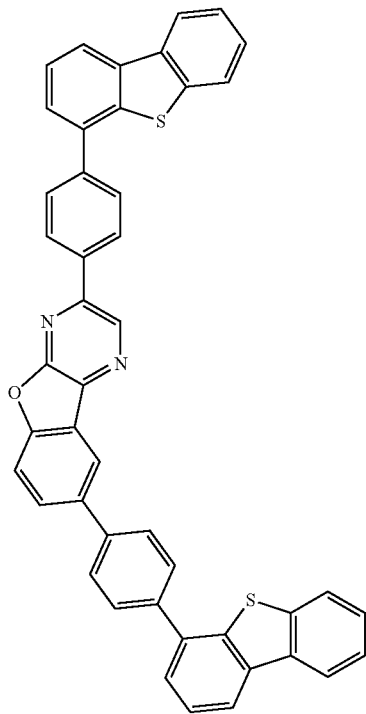

(106)
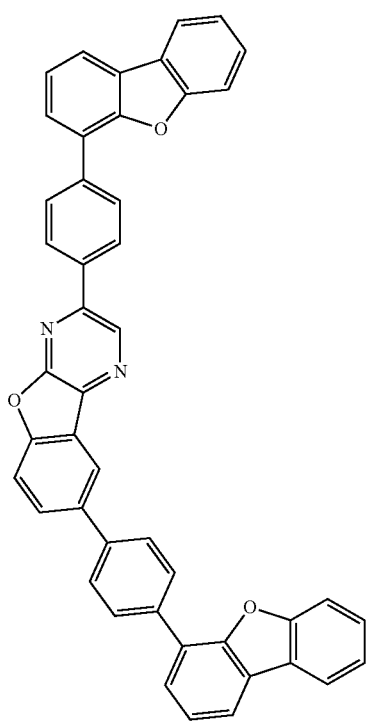
(107)
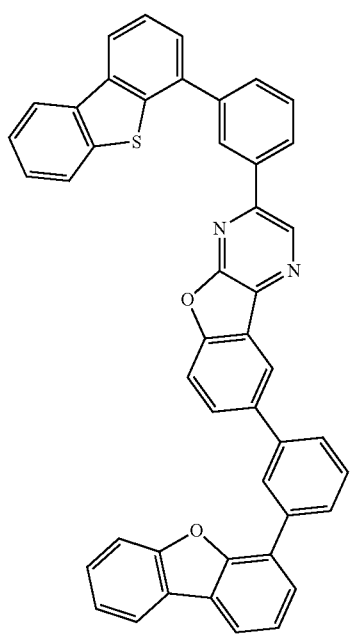
(108)
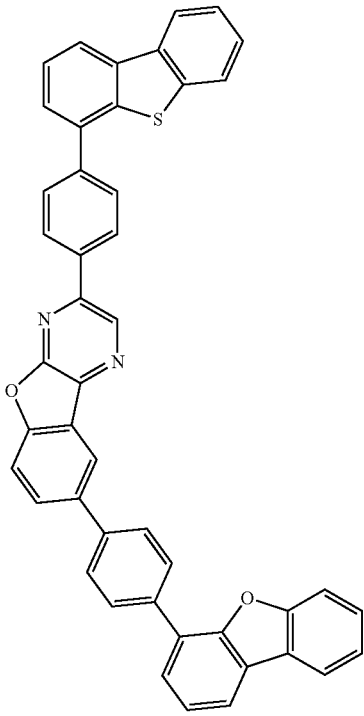
(109)
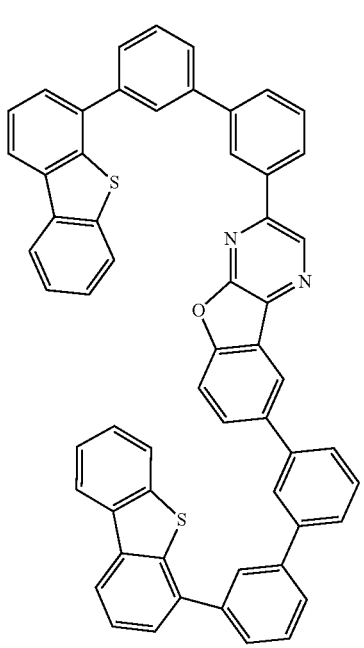

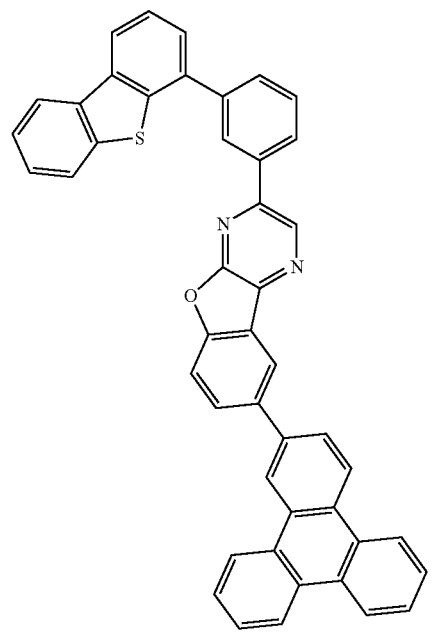
(110)
(111)
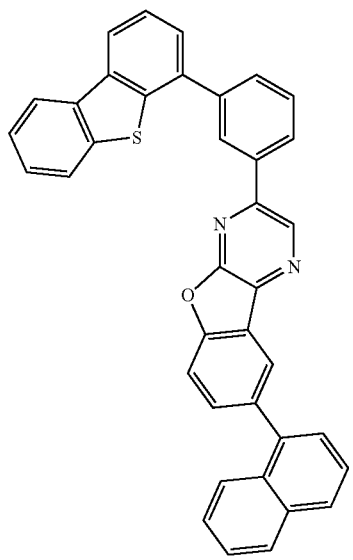
(112)
(113)

(114)
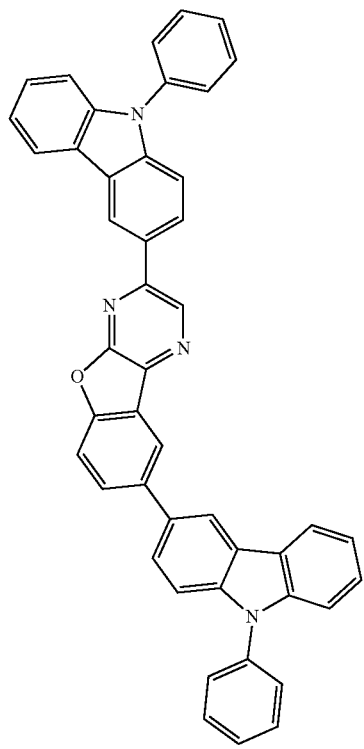
(115)
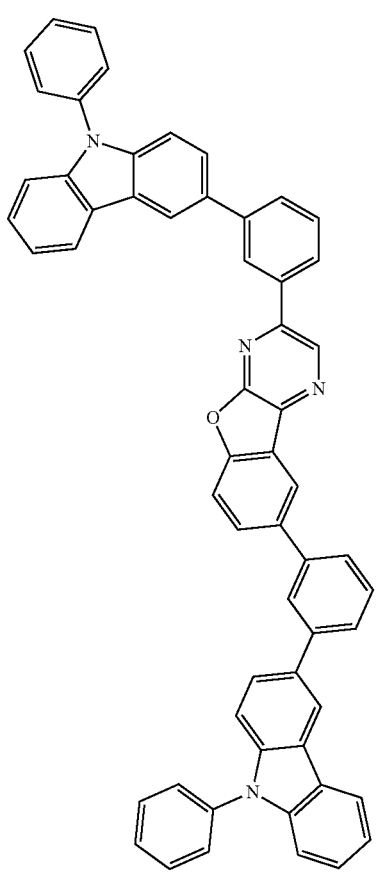
(116)
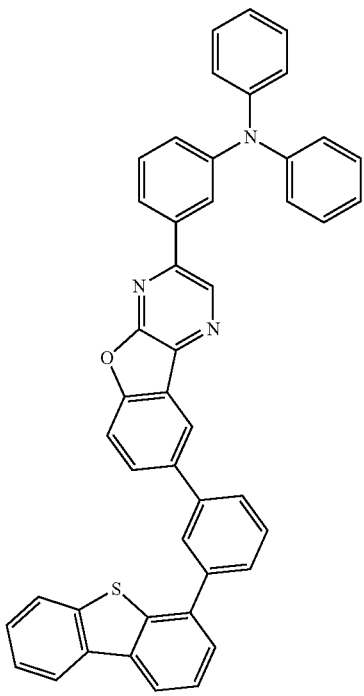
(117)
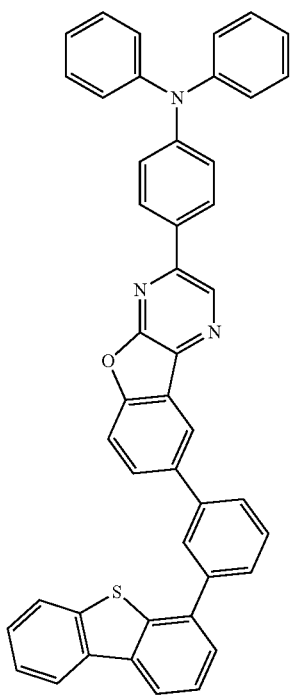

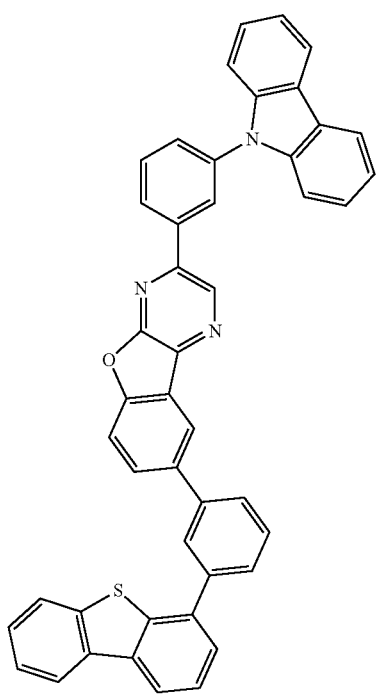
(118)
(119)
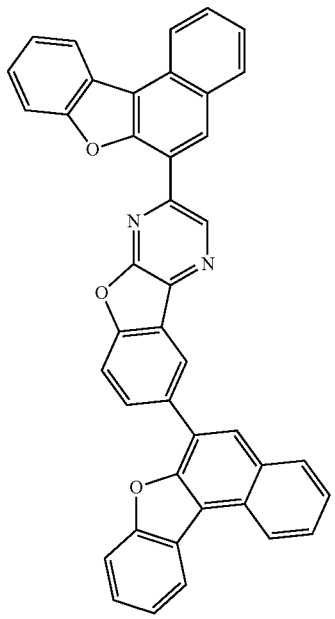
(120)
(121)

(122)
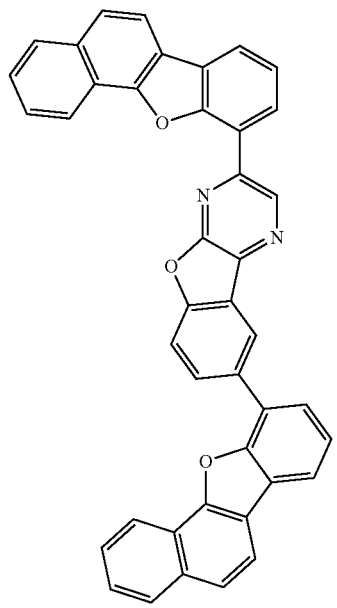
(123)
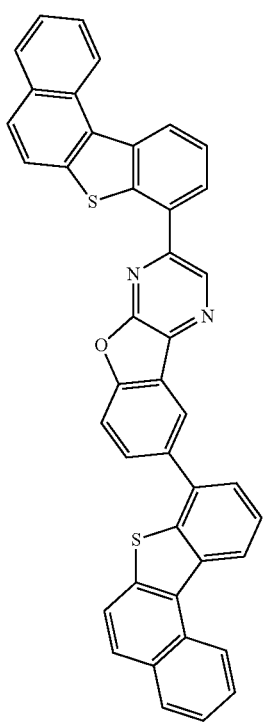
(124)
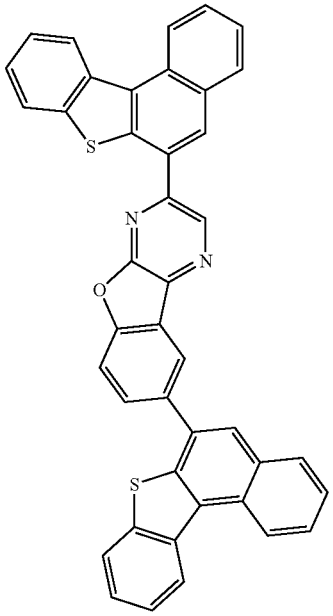
(125)
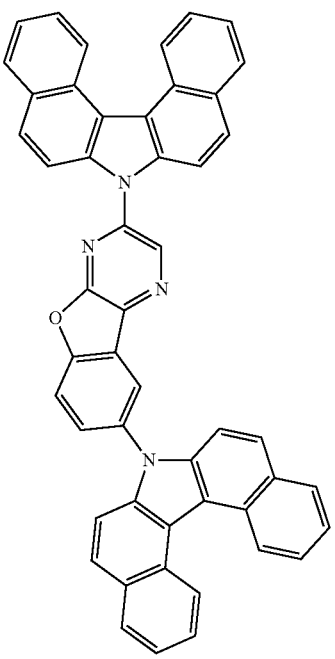

(126)
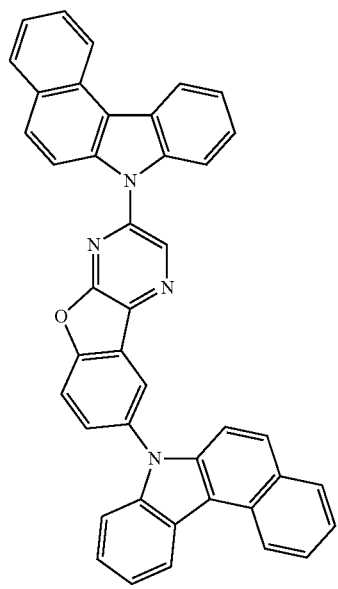
(127)
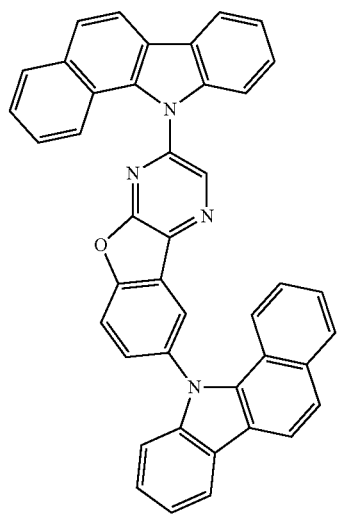
(128)
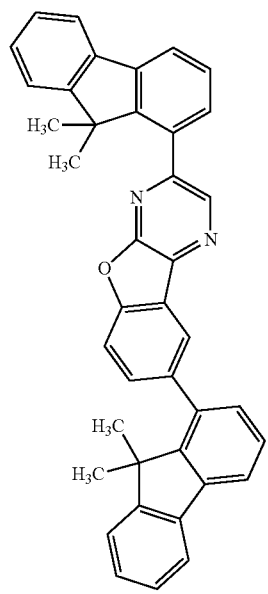
(129)
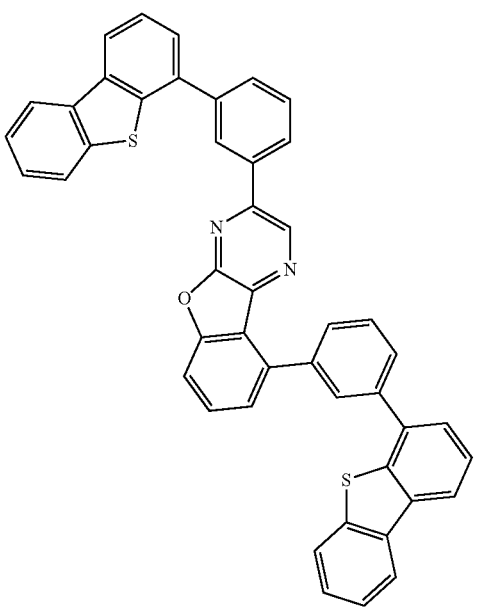

(130)
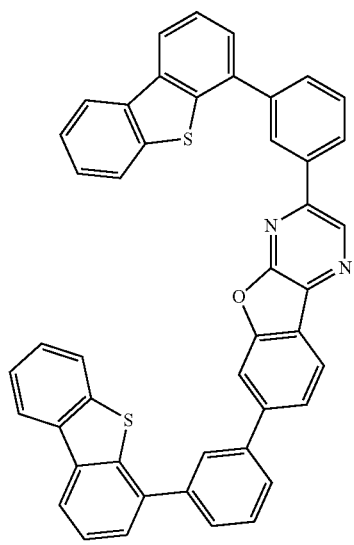
(132)
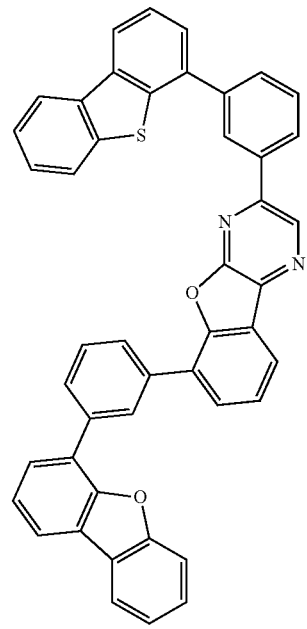
(131)
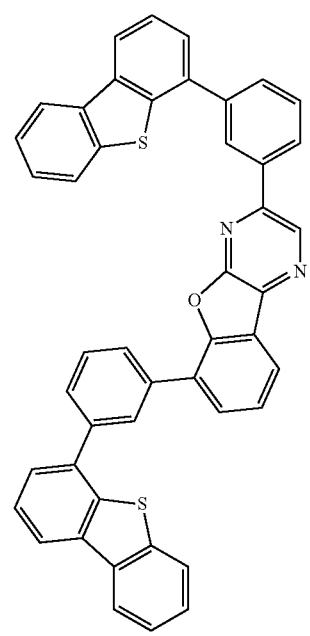
(133)
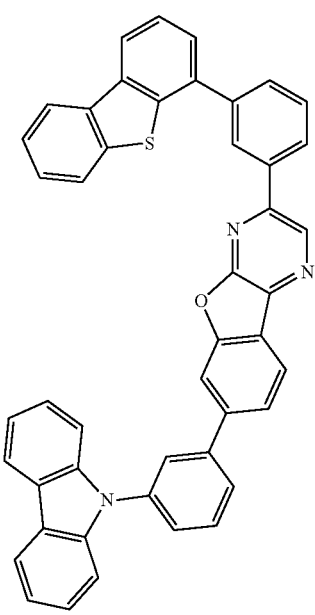

(134)
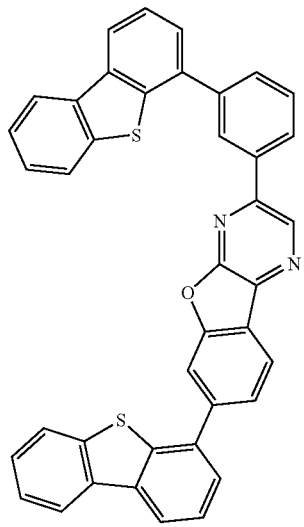
(135)
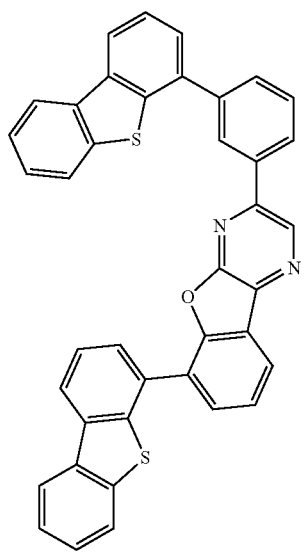
(136)
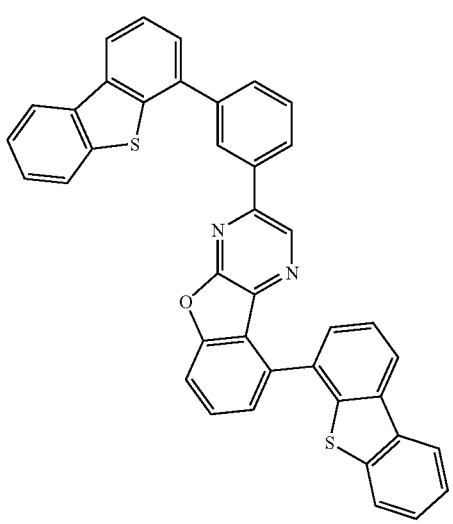
(137)
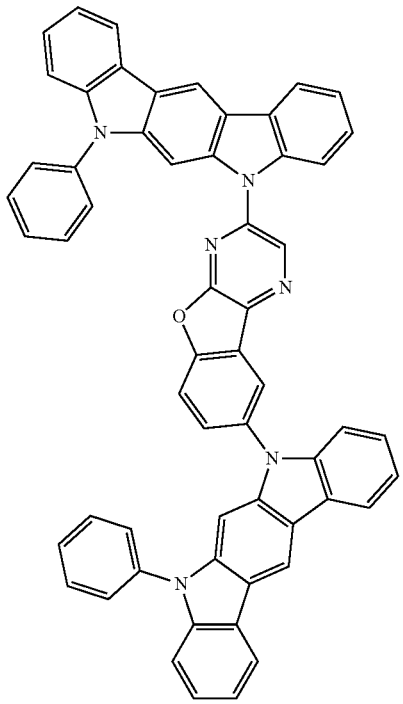
(138)
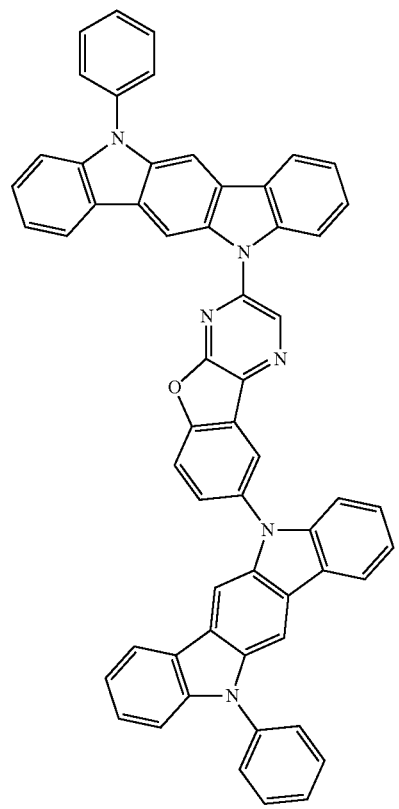

(139)
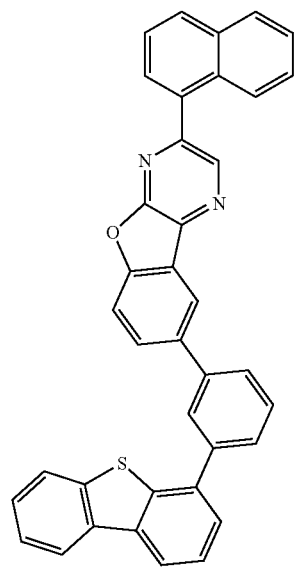
(140)
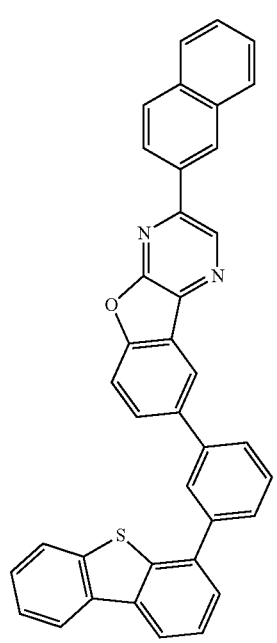
(141)
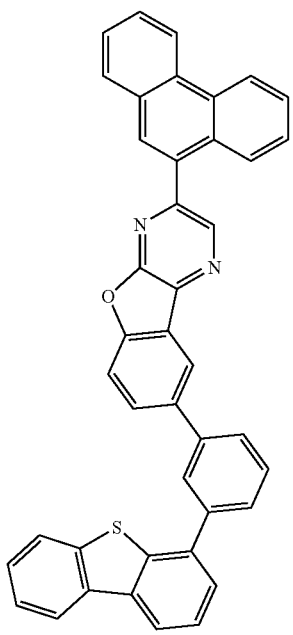
(142)
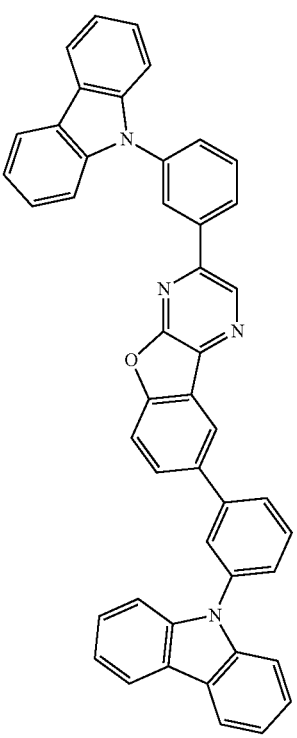

(143)
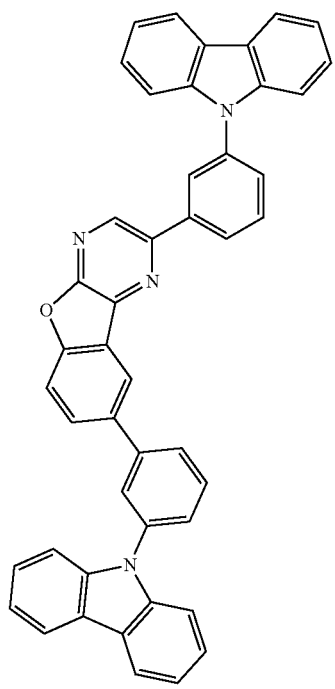
(144)
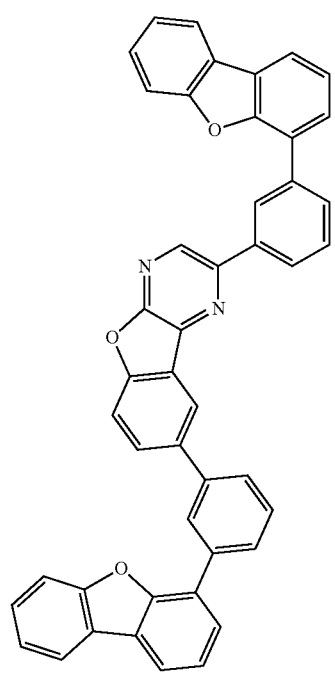
(145)
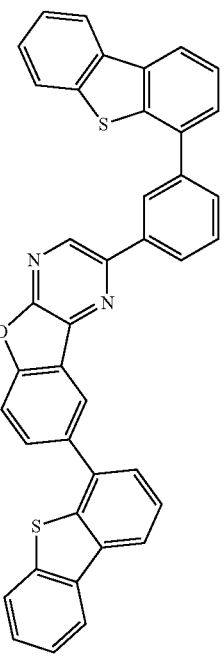
(146)
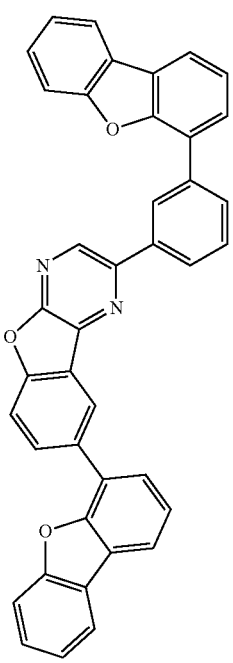

-continued
(147)
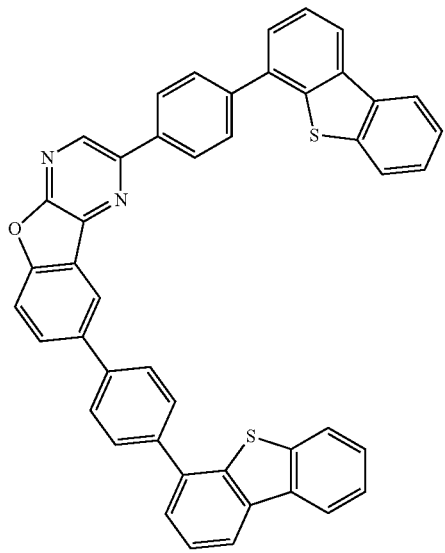
(149)
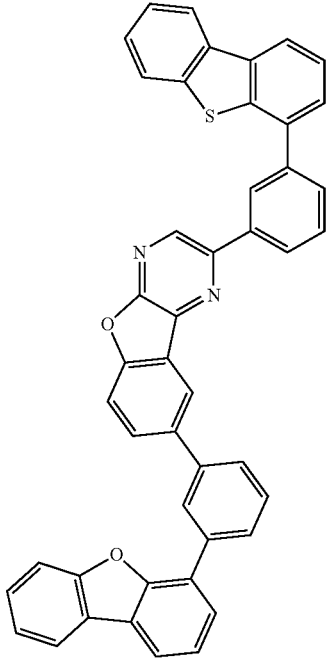
(148)
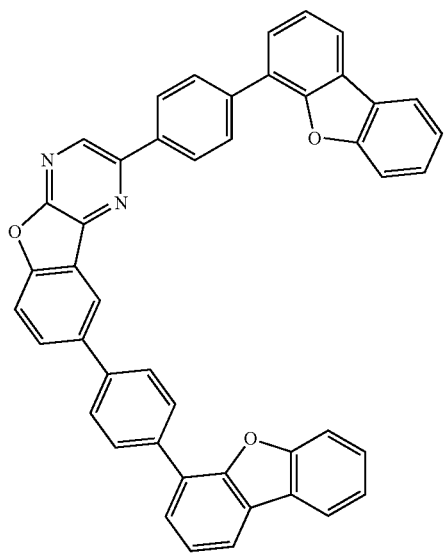
(150)
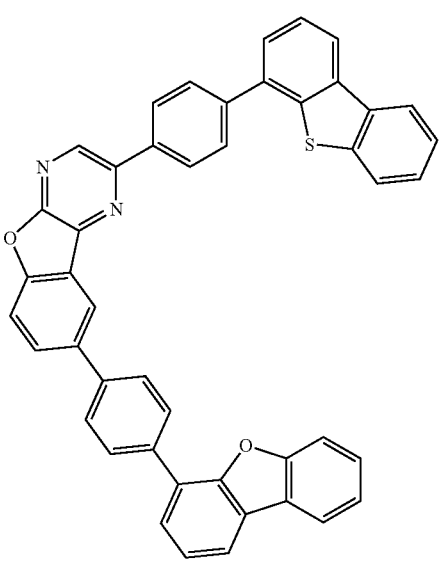

(151)
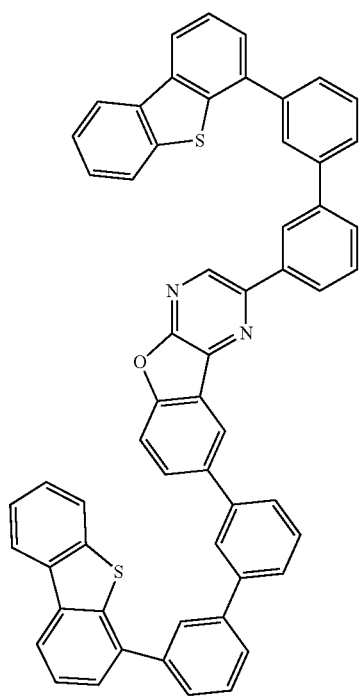
(152)
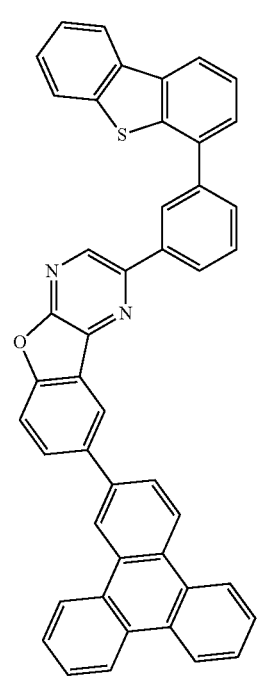
(153)
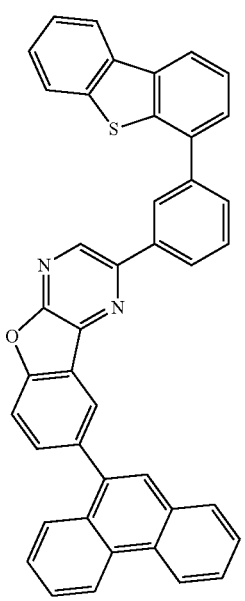
(154)
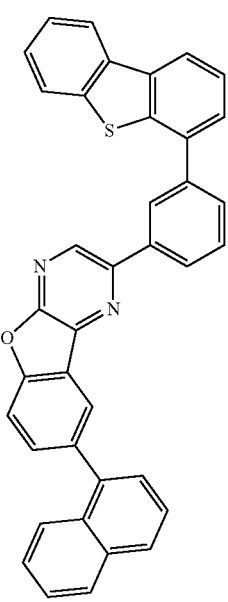

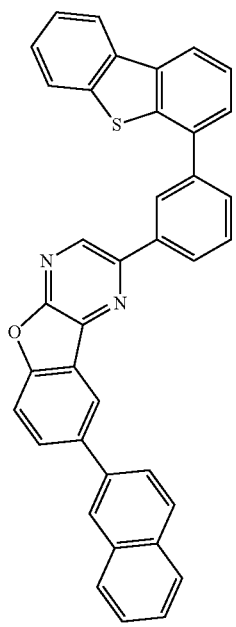
(155)
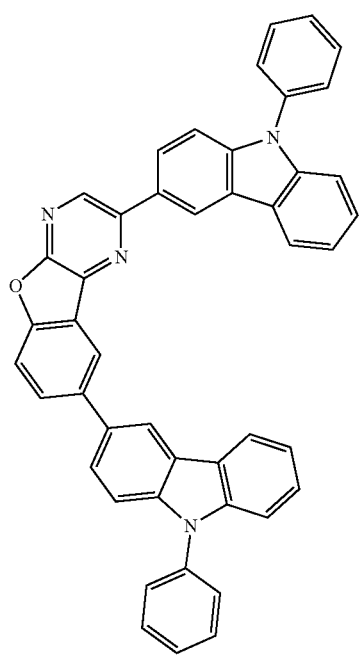
(156)
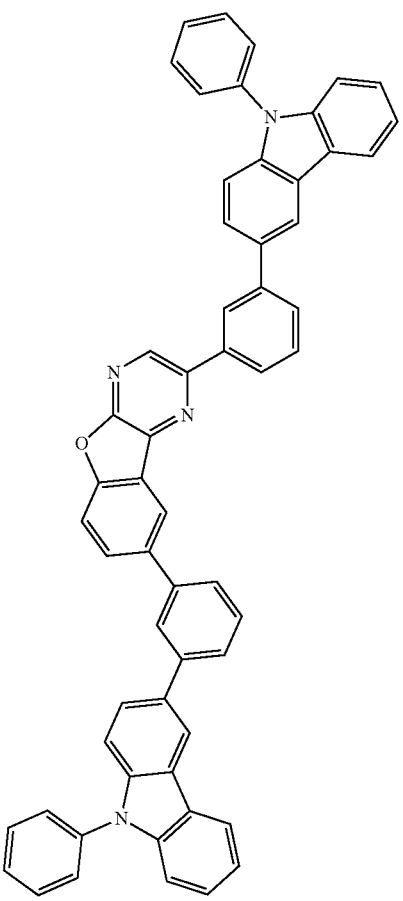
(157)
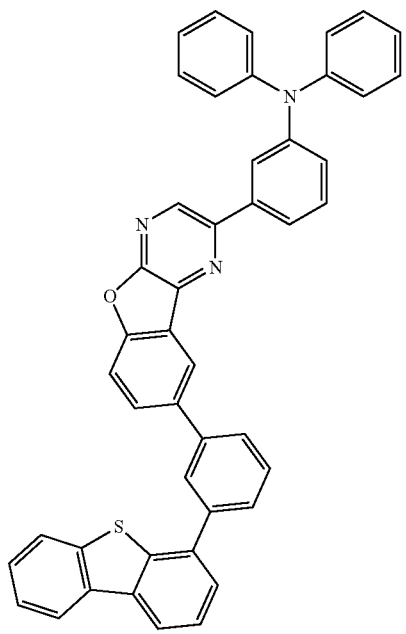
(158)

(159)
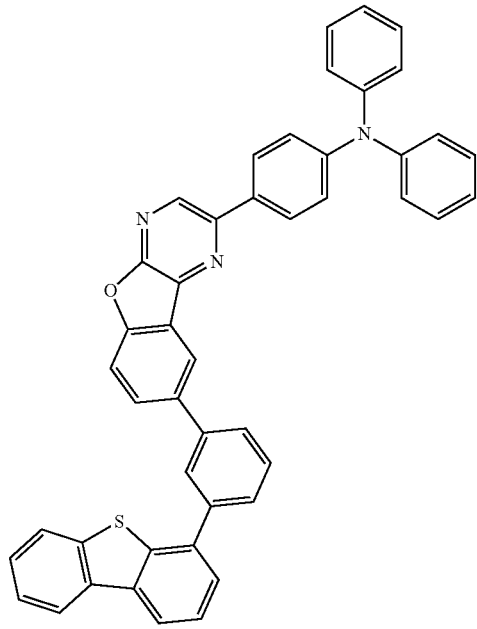
(161)
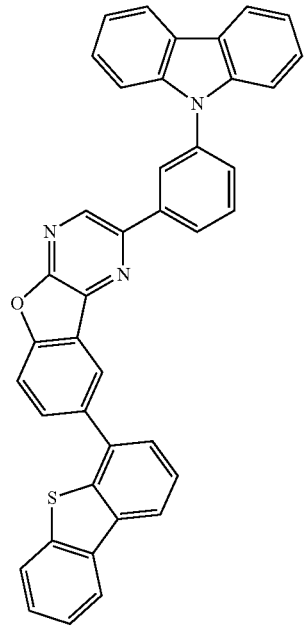
(160)
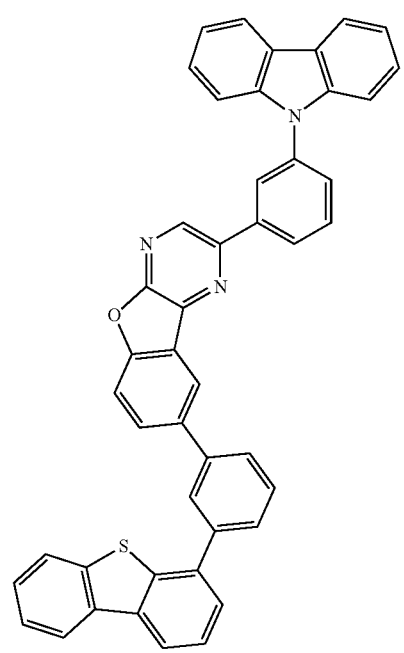
(162)
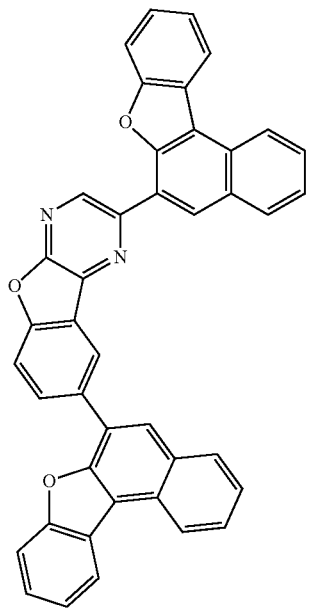

(163)
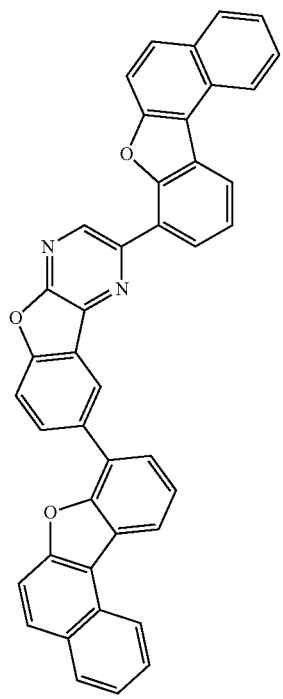
(164)
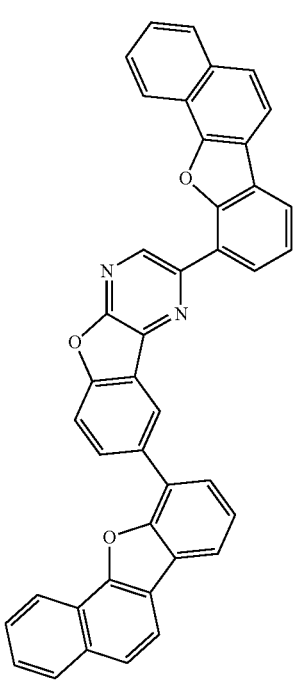
(165)
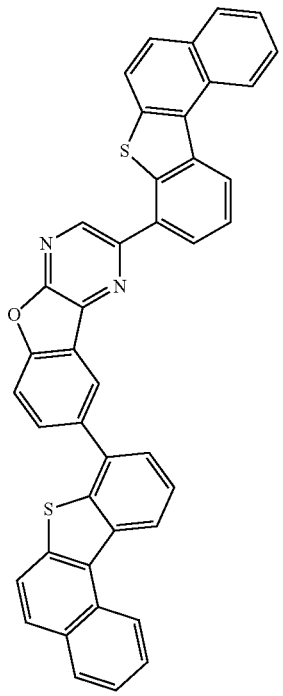
(166)
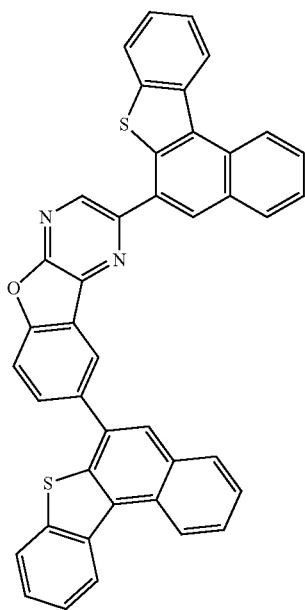

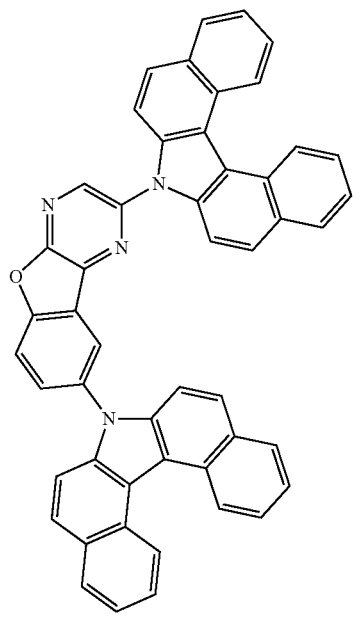
(167)
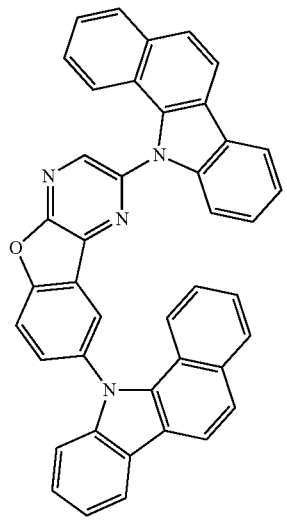
(169)
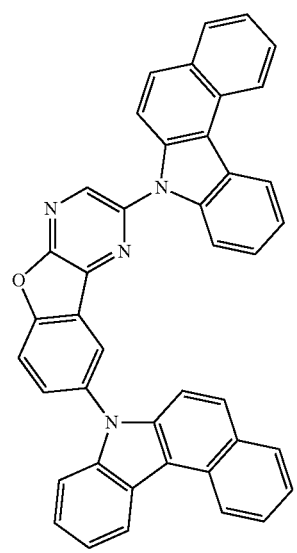
(168)
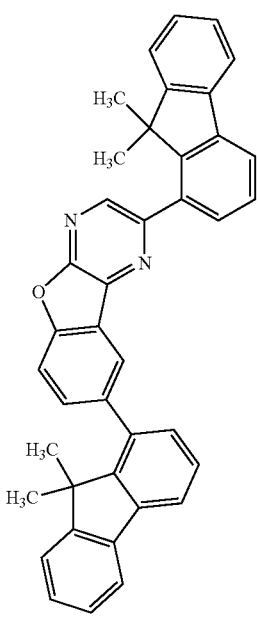
(170)

(171)
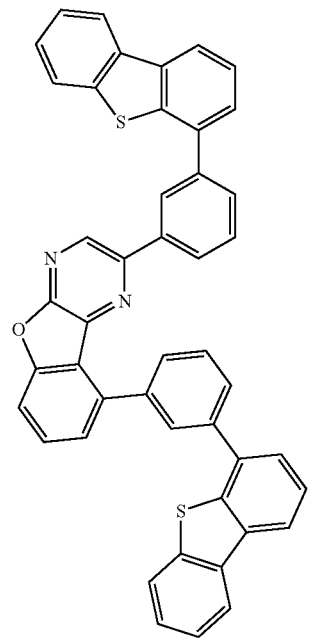
(172)
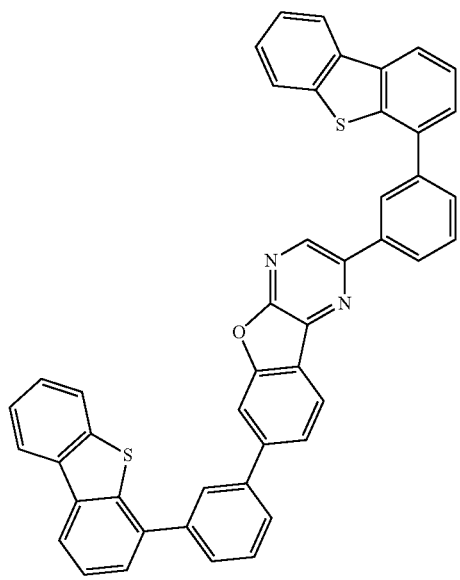
(173)
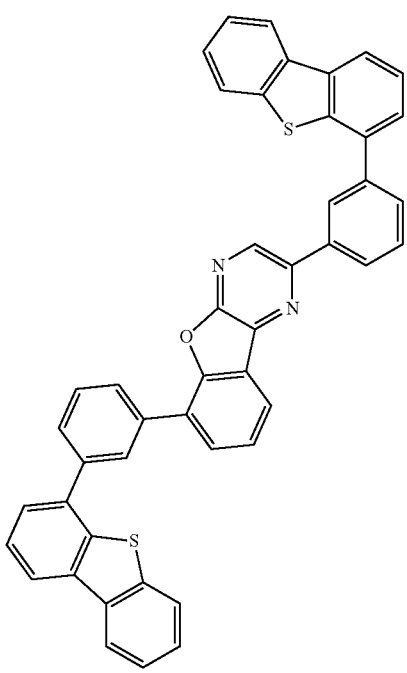
(174)
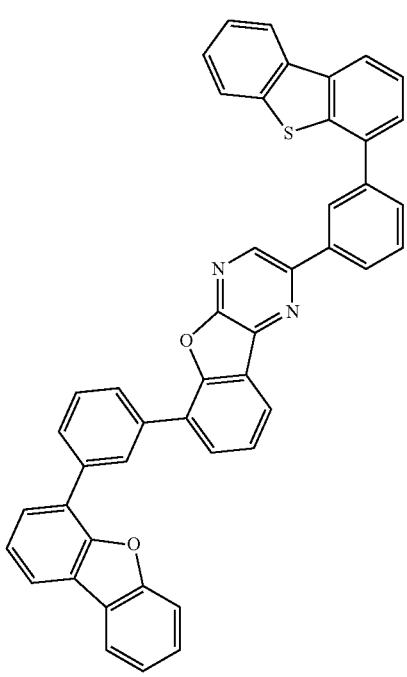

(175)
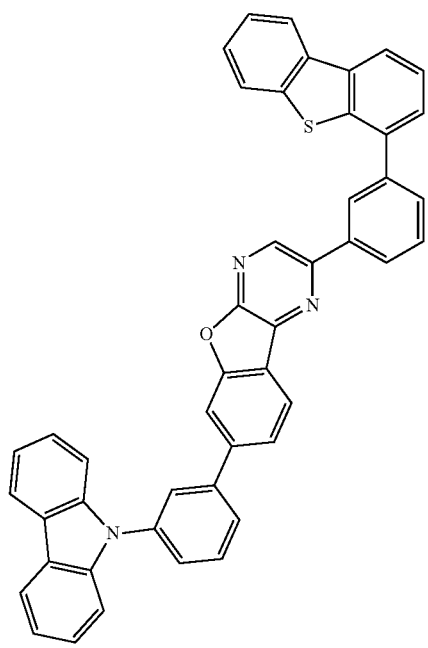
(176)
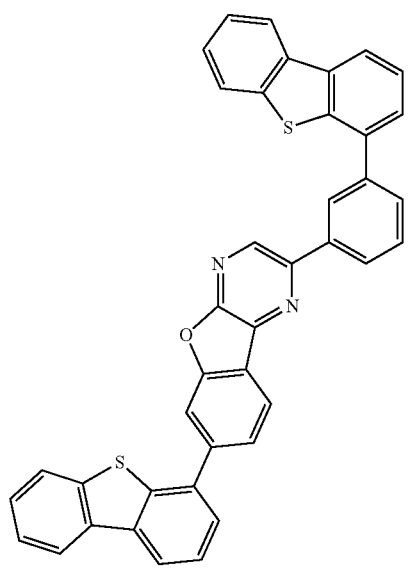
(177)
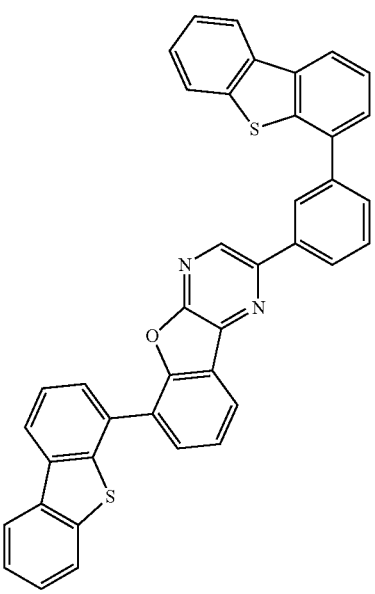
(178)
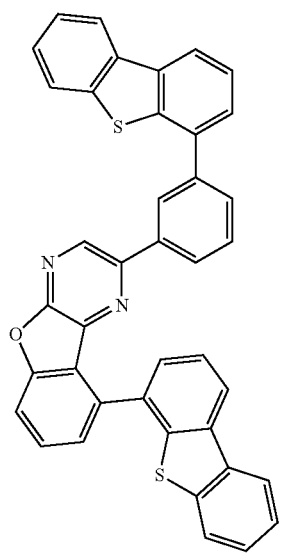

(179)
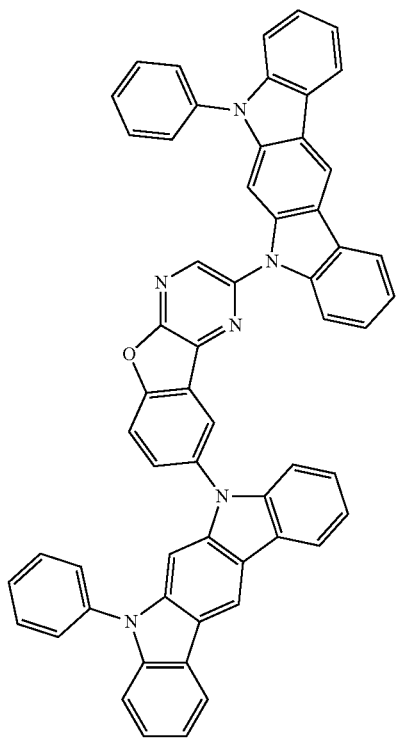
(180)
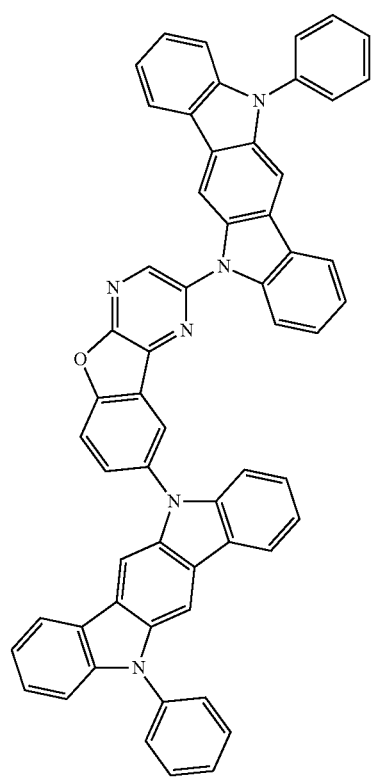
(181)
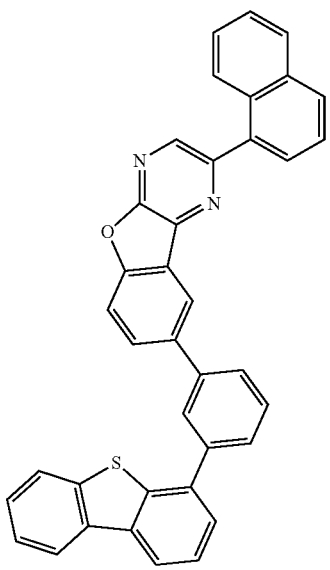
(182)
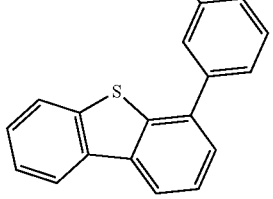
(183)
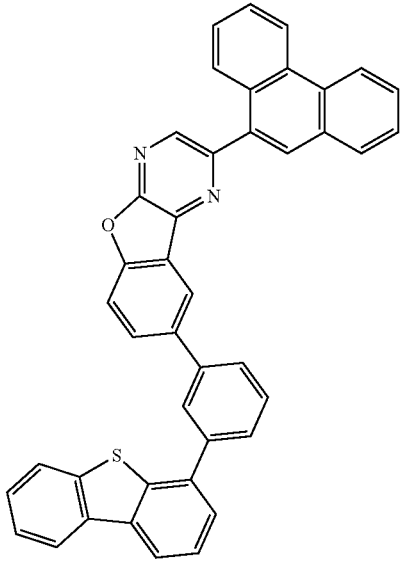

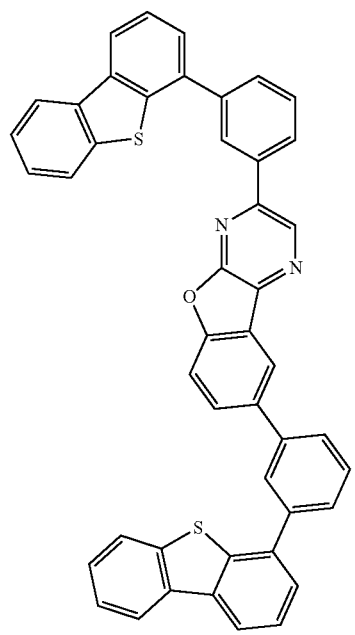
(184)
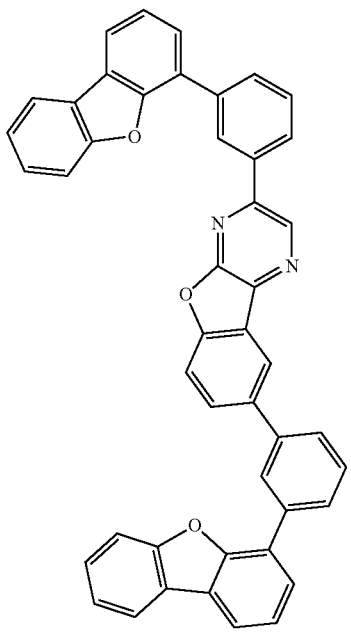
(186)
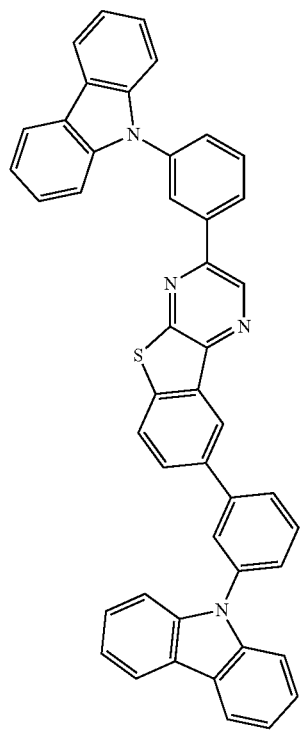
(185)
(187)

(188)
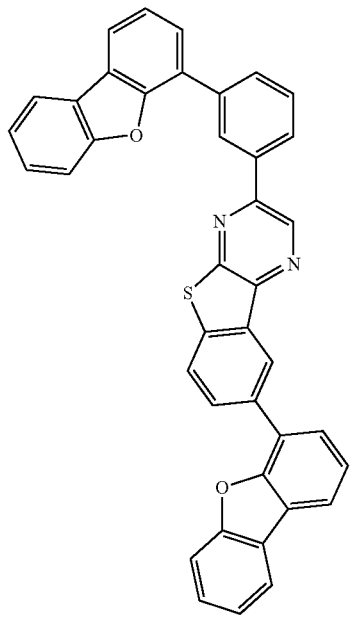
(189)
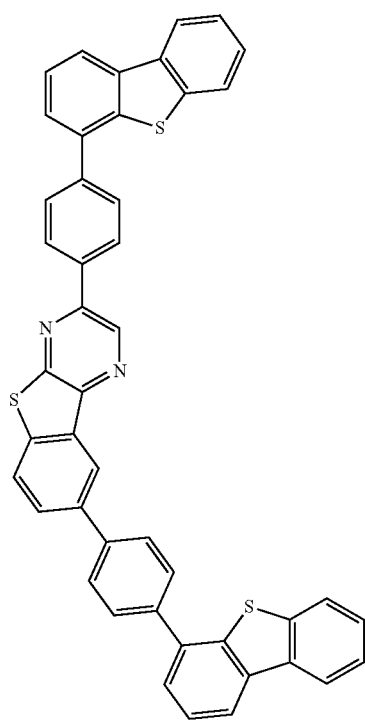
(190)
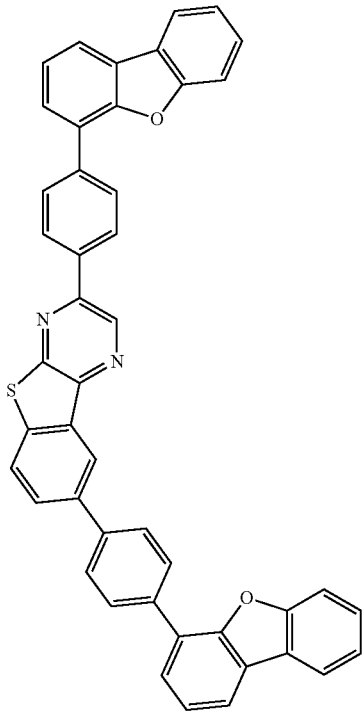
(191)
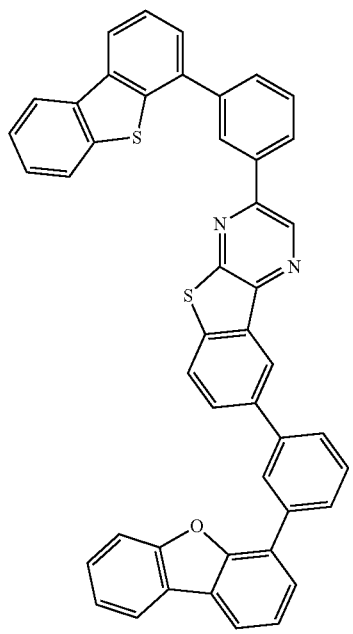

(192)
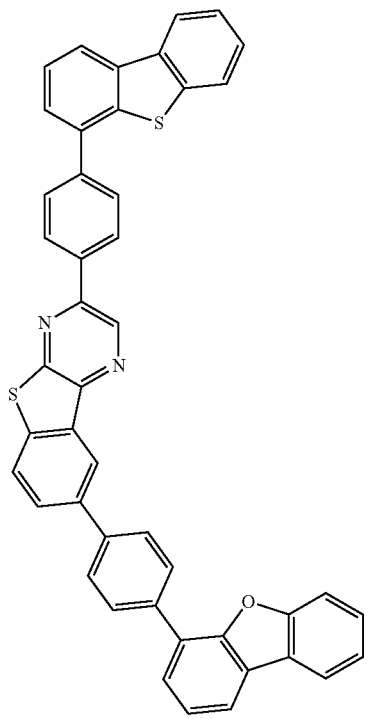
(193)
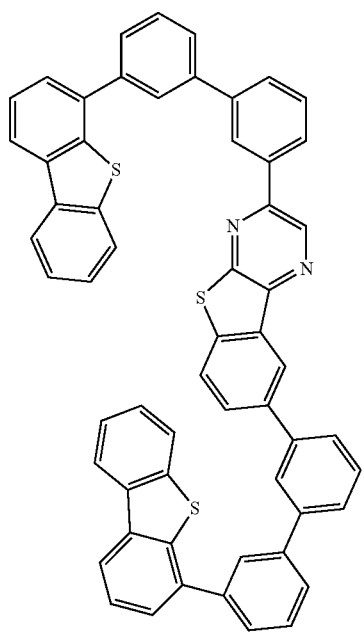
(194)
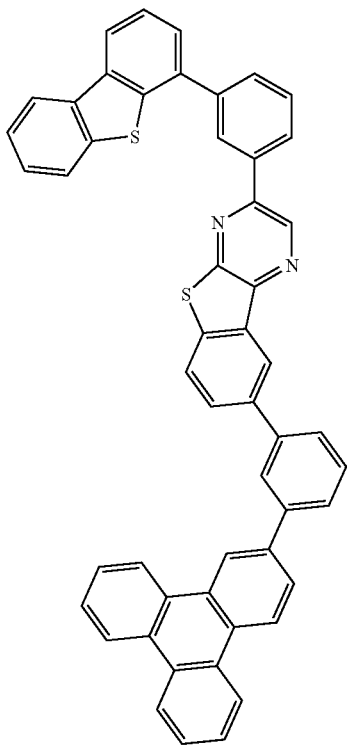
(195)
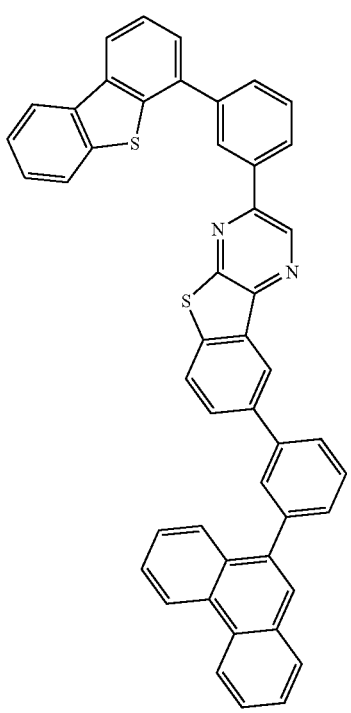

(196)
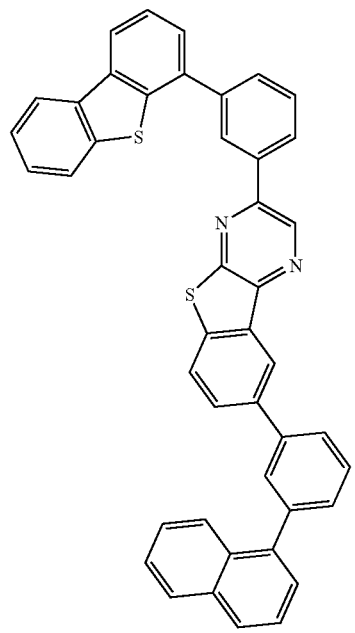
(197)
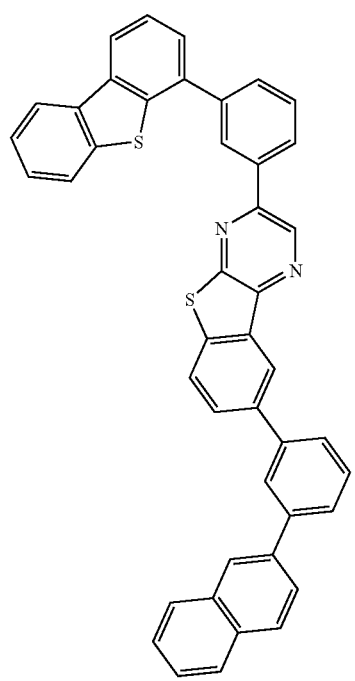
(198)
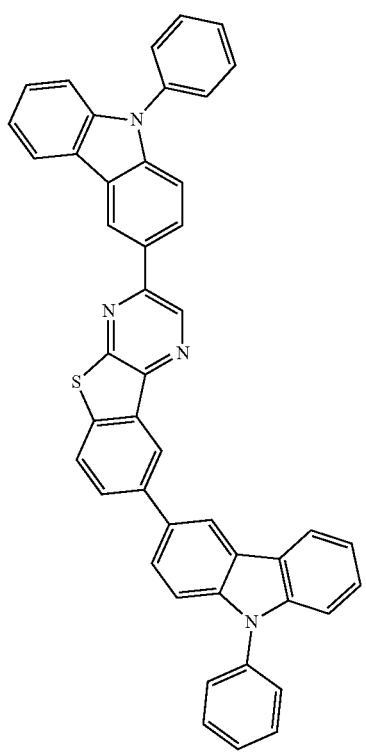
(199)
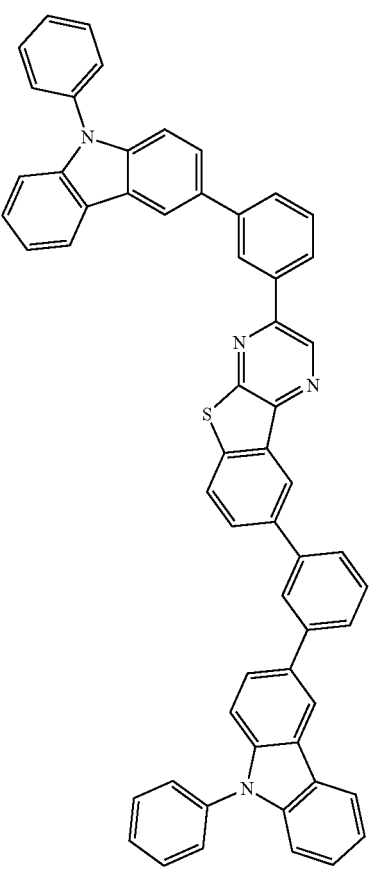

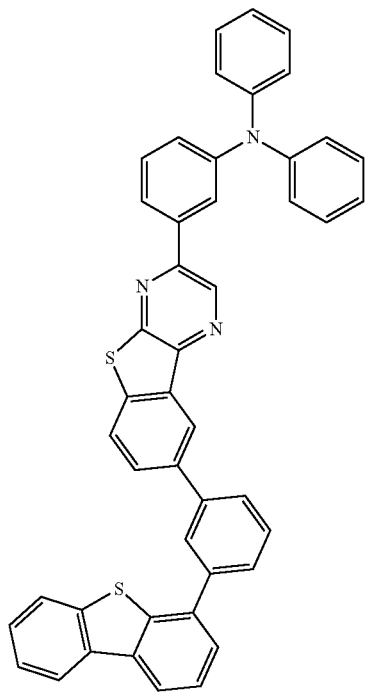
(200)
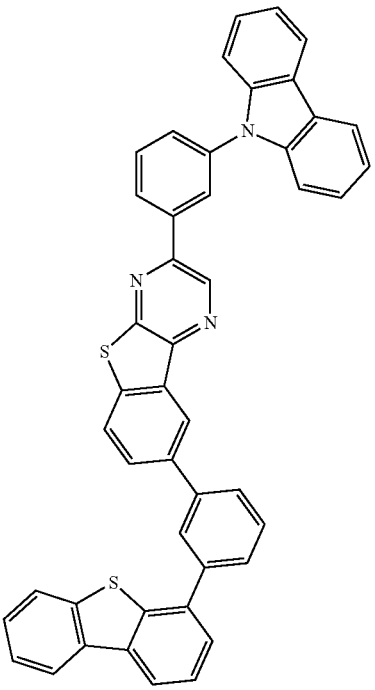
(202)
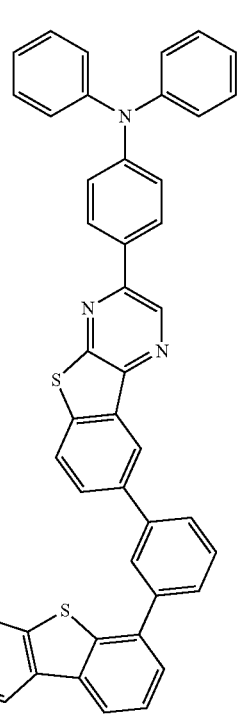
(201)
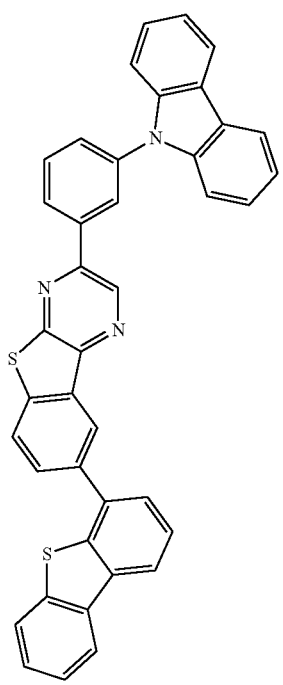
(203)

(204)
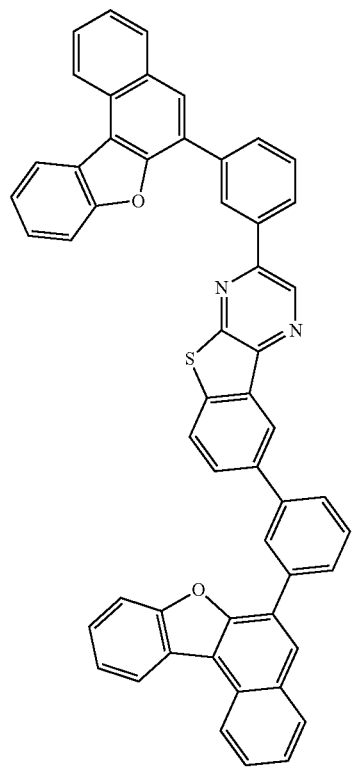
(206)
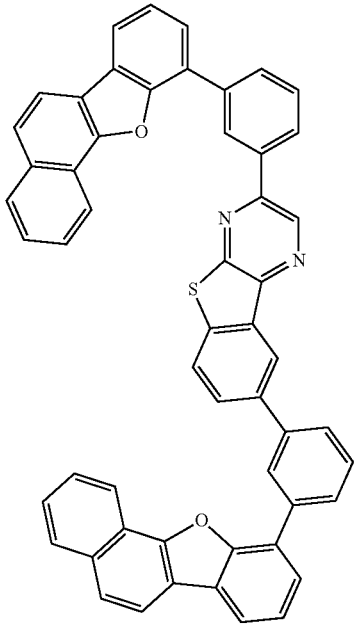
(205)
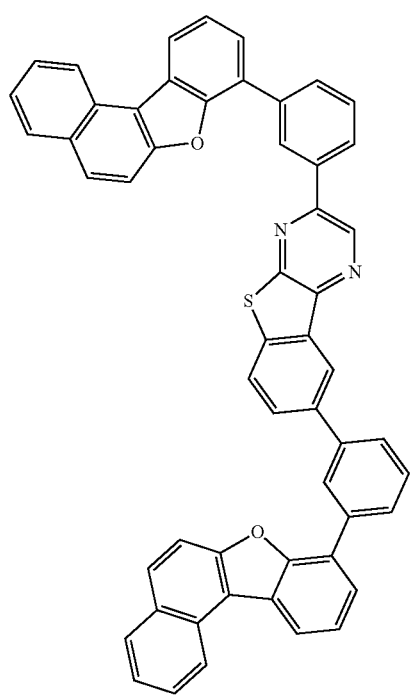
(207)
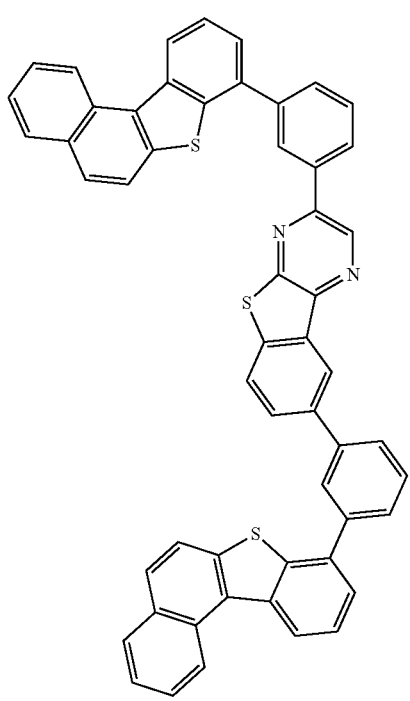

(208)
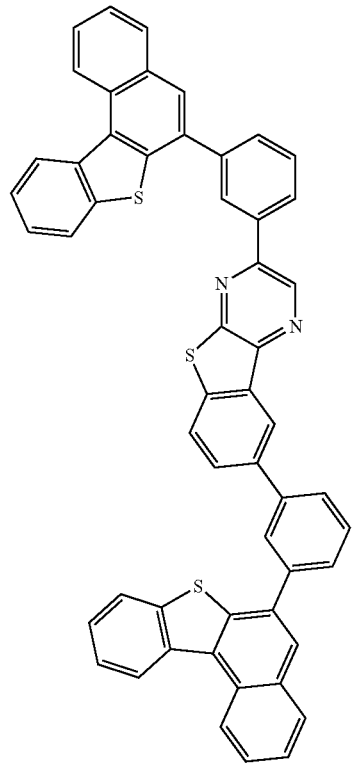
(209)
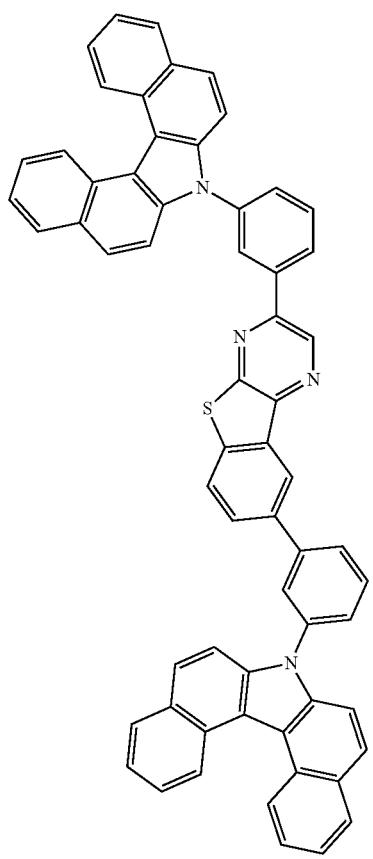
(210)
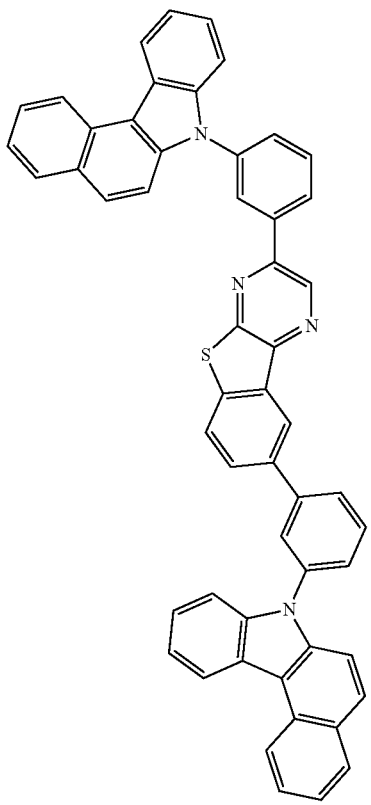
(211)
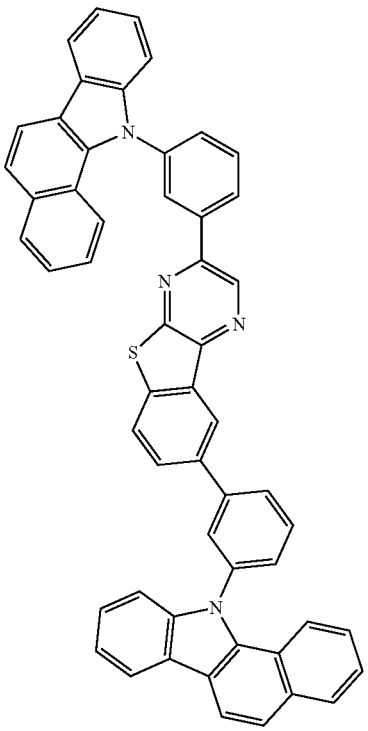

(212)
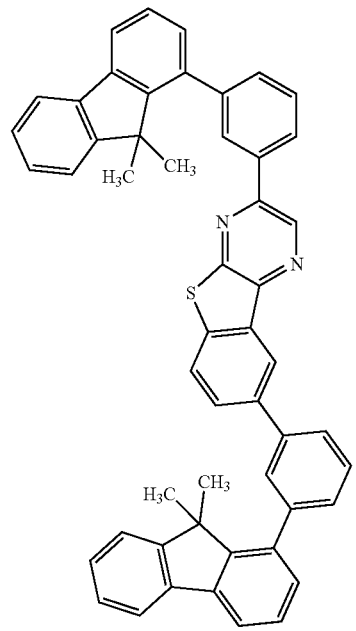
(214)
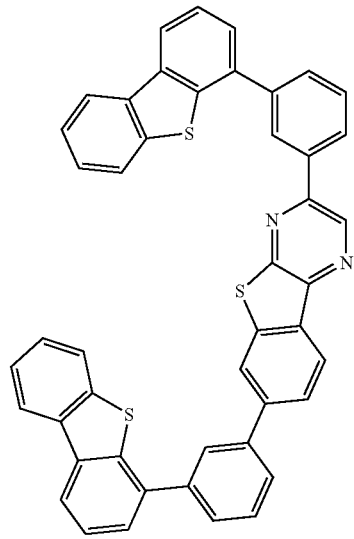
(213)
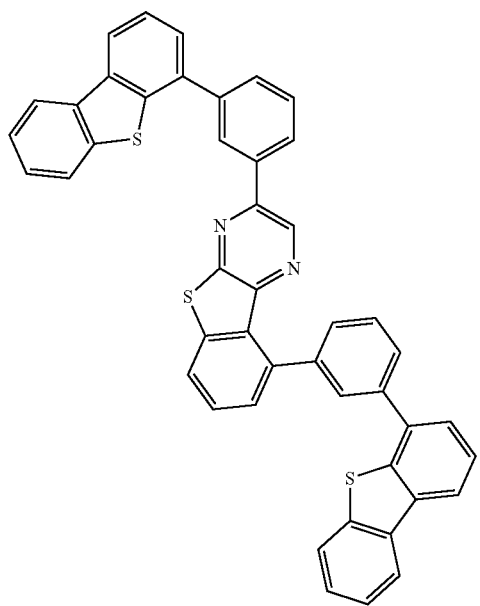
(215)
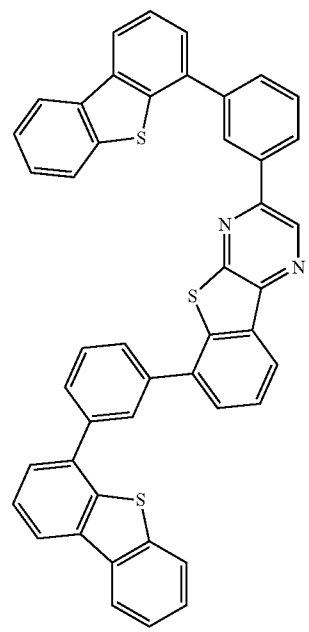

(216)
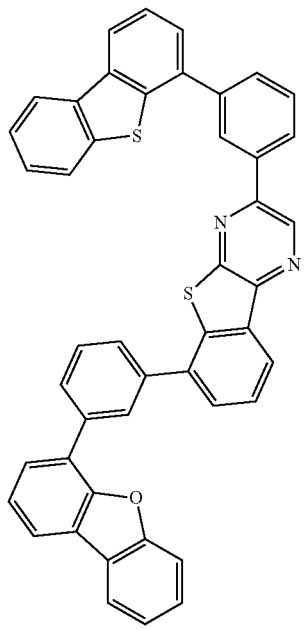
(217)
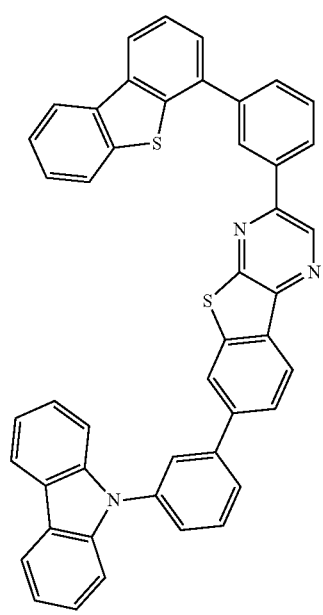
(218)
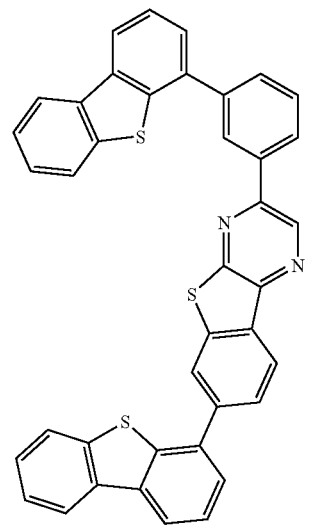
(219)
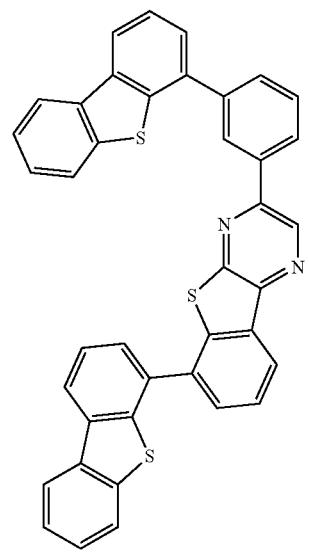
(220)
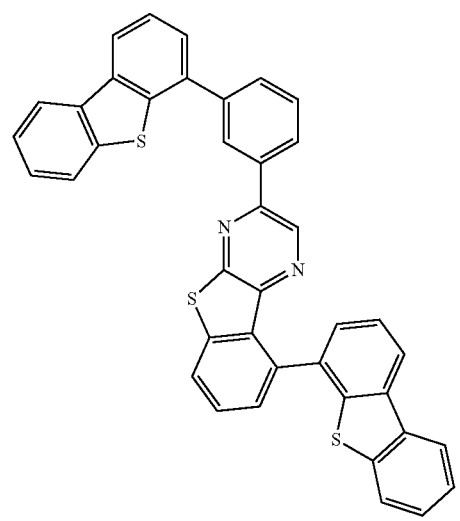

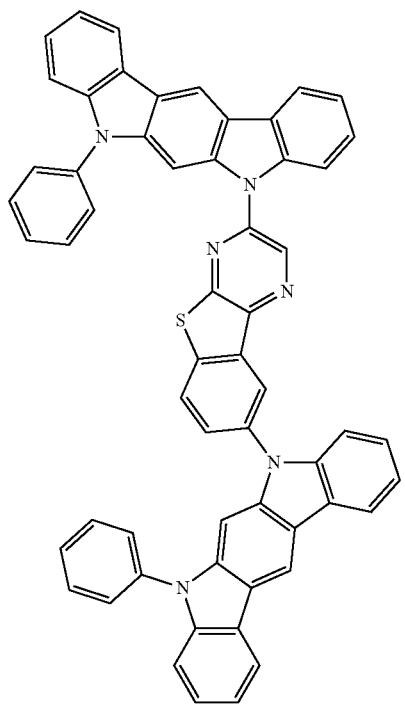
(221)
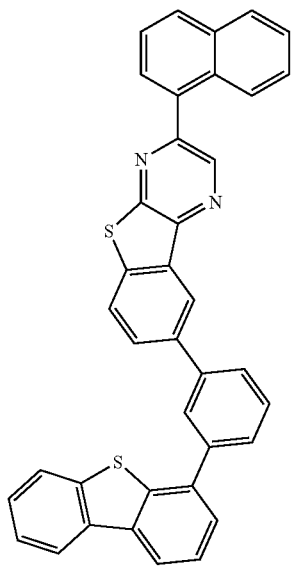
(223)
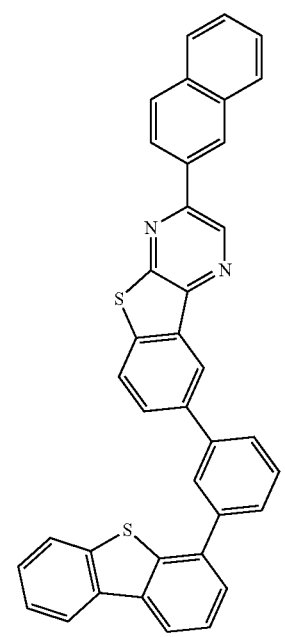
(222)
(224)

87
-continued
(225)
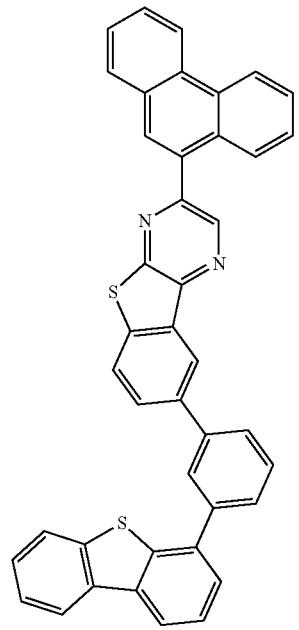
(226)
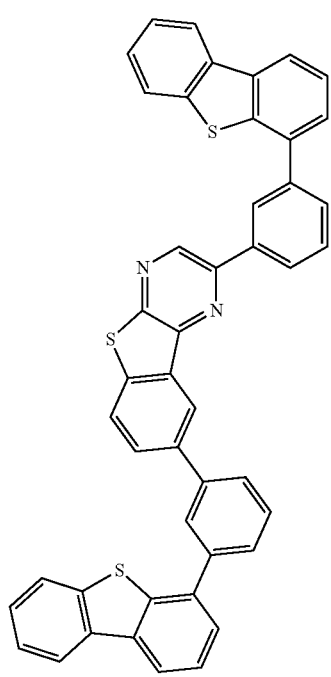
88
-continued
(227)
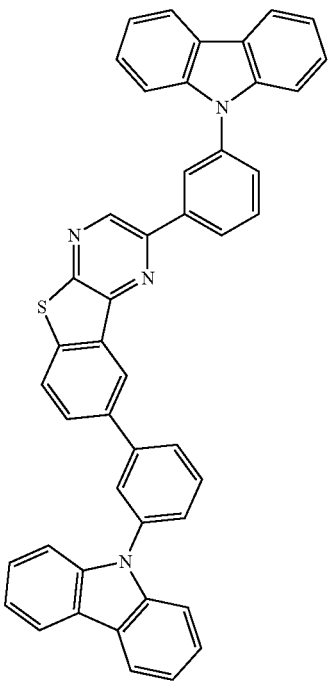
(228)
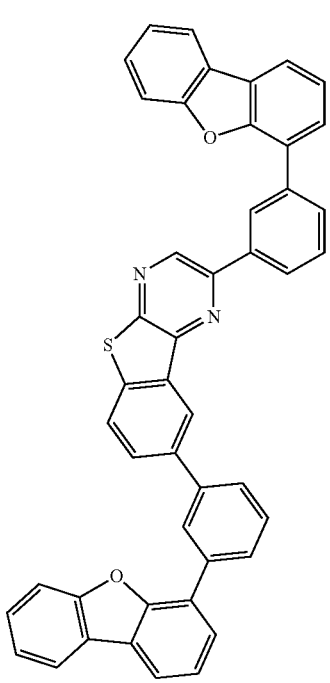

(229)
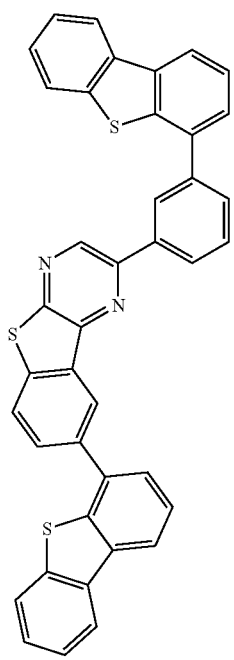
(230)
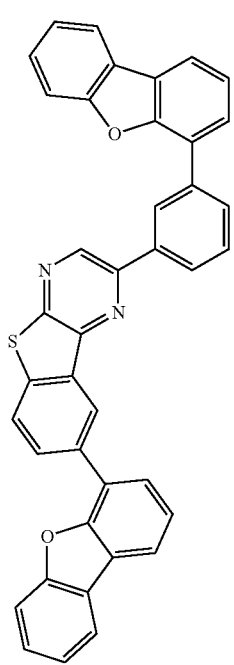
(231)
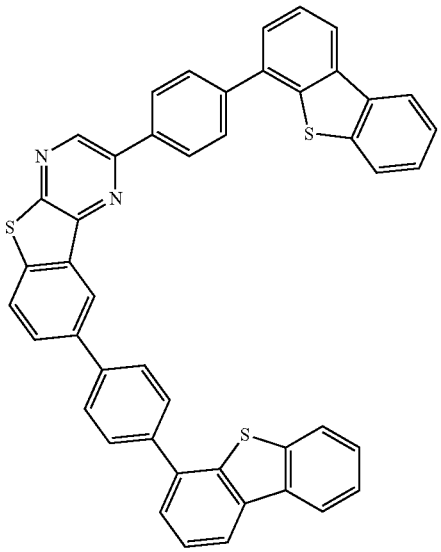
(232)
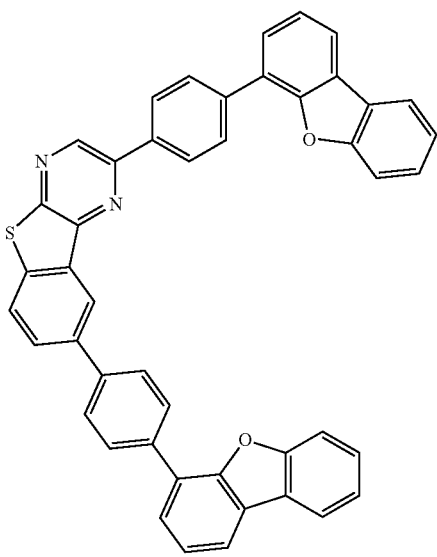

(233)
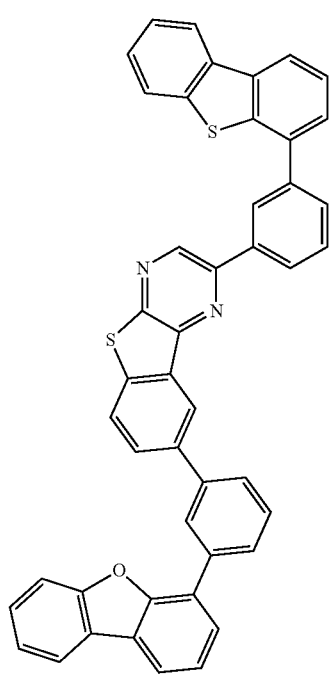
(234)
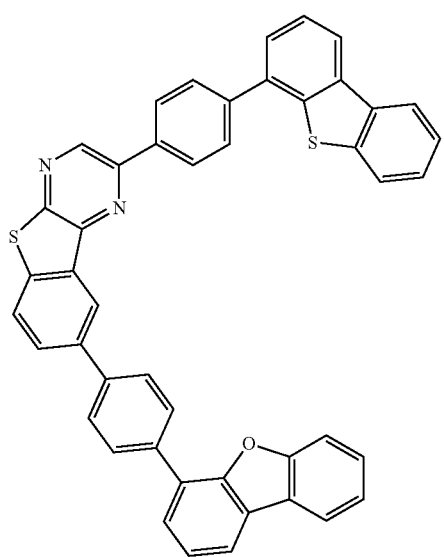
(235)
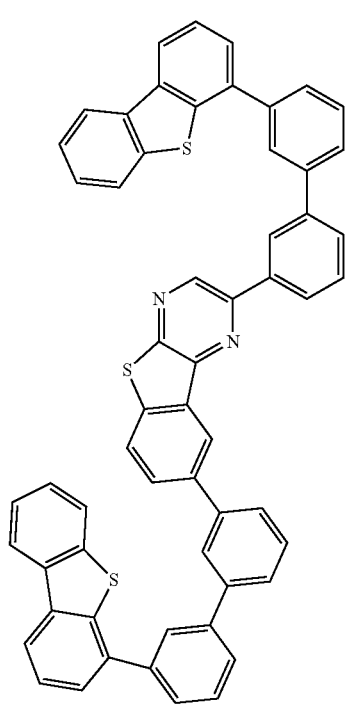
(236)
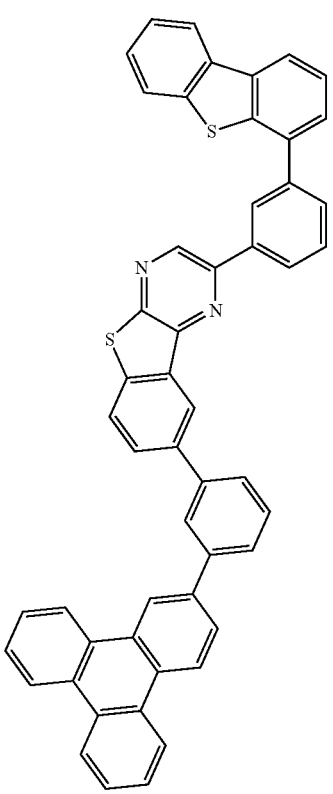

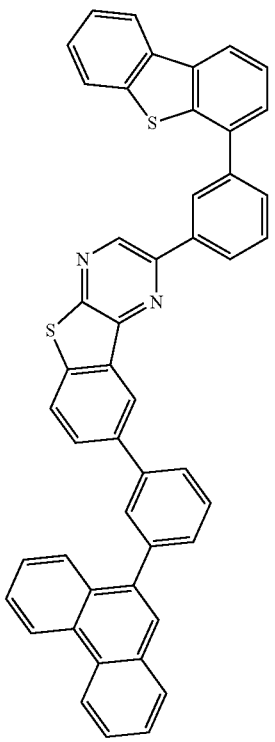
(237)
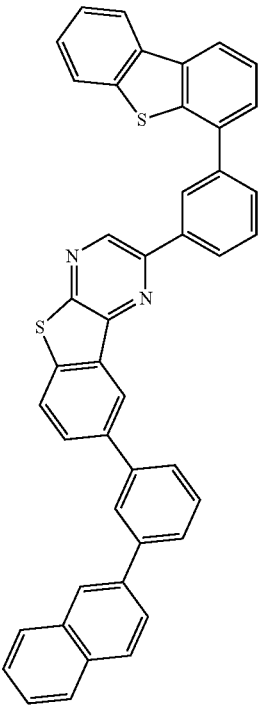
(239)
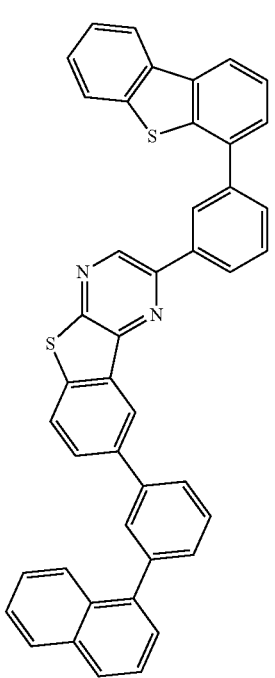
(238)
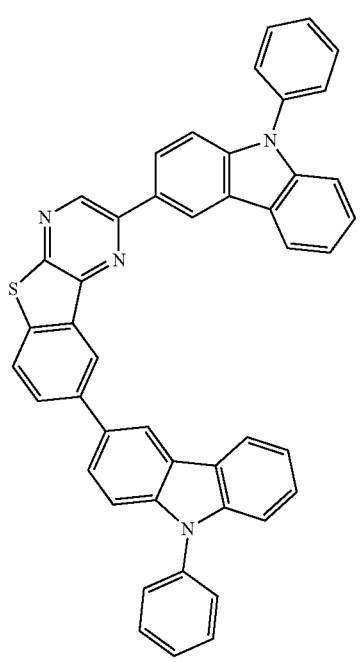
(240)

(241)
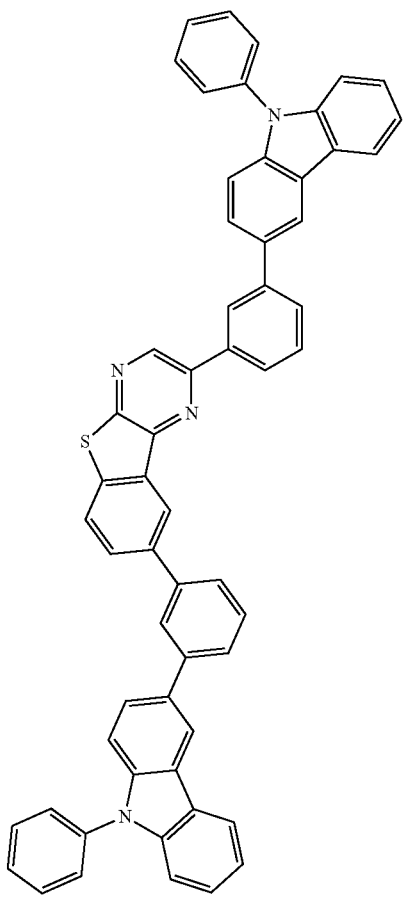
(242)
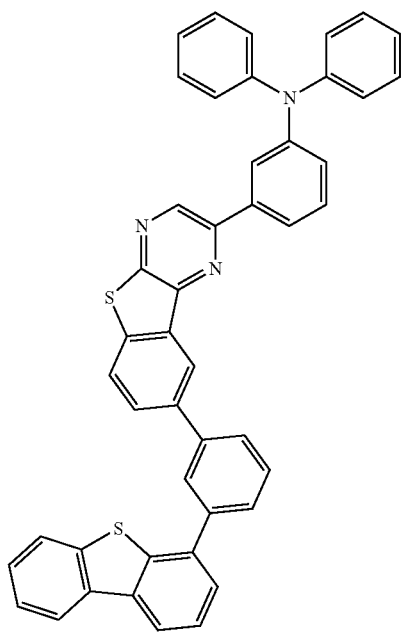
(243)
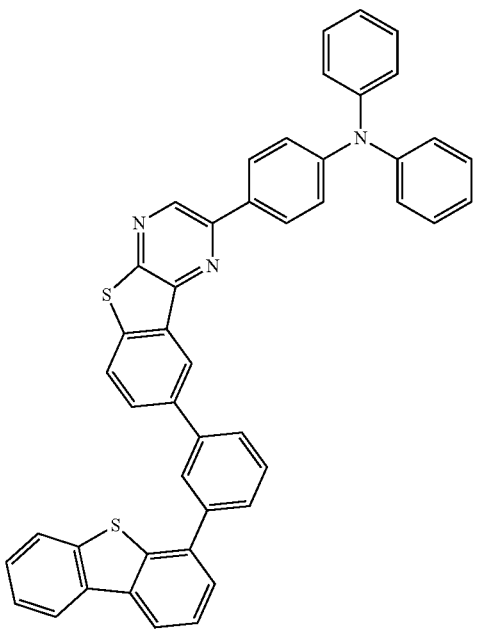
(244)
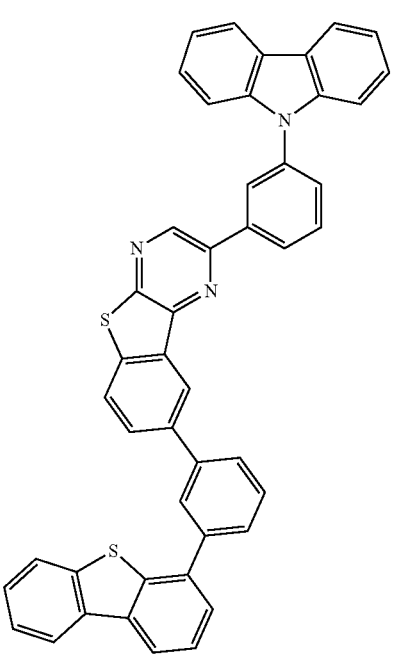

(245)
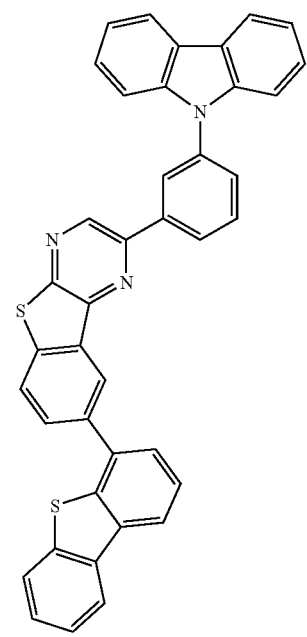
(246)
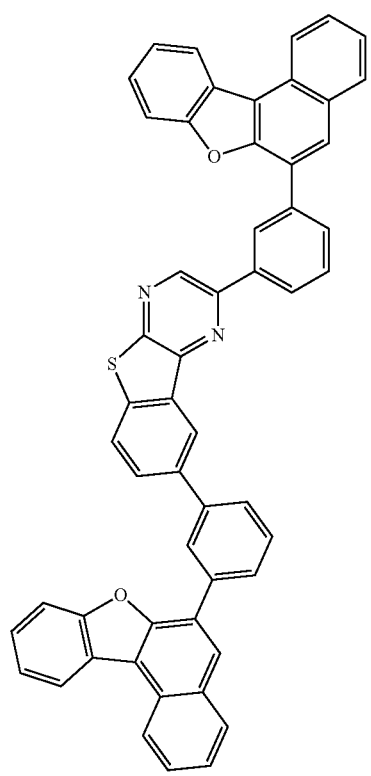
(247)
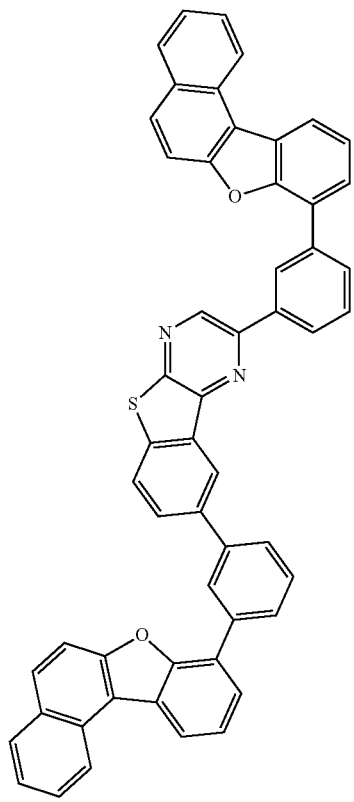
(248)
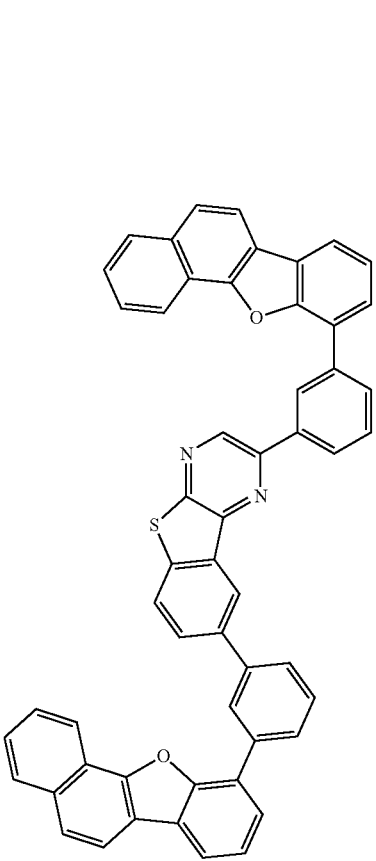

-continued
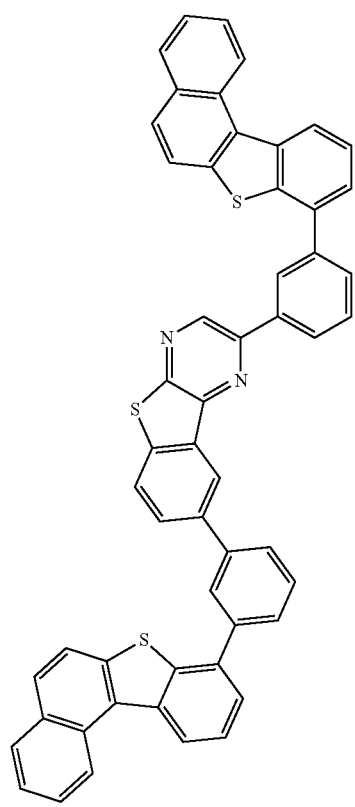
(249)
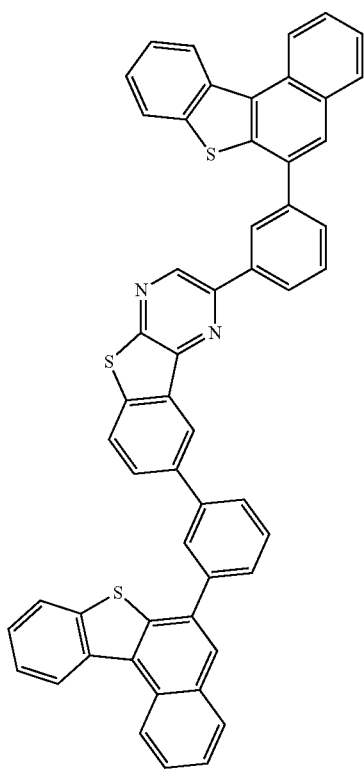
(250)
-continued
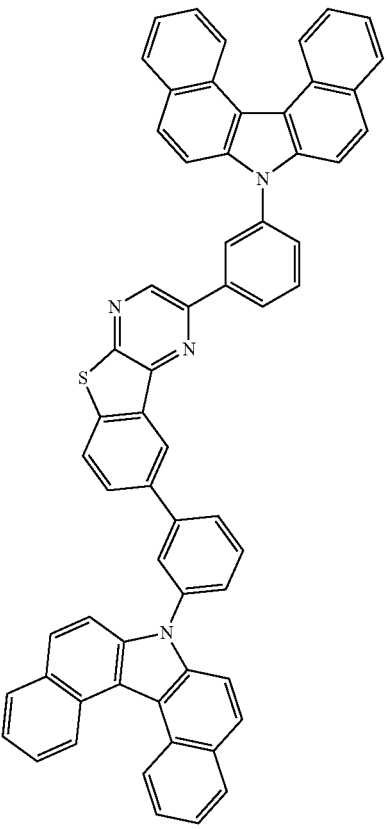
(251)
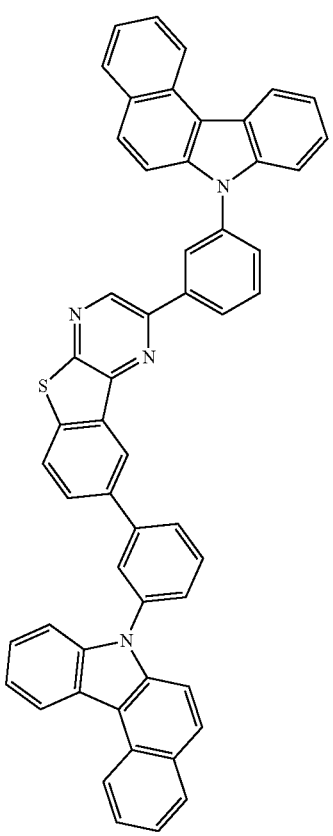
(252)

101
102
(253)
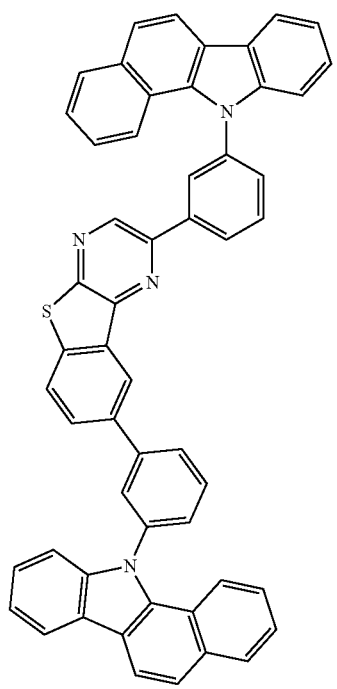
(254)
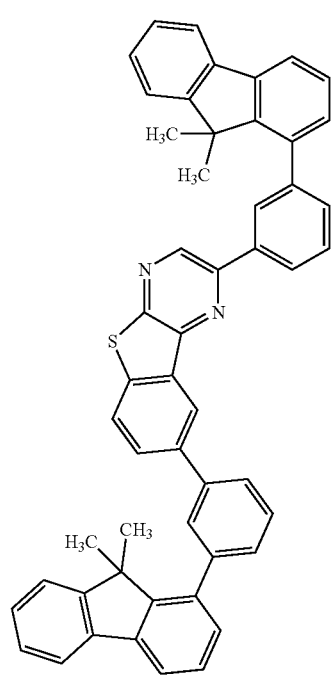
(255)
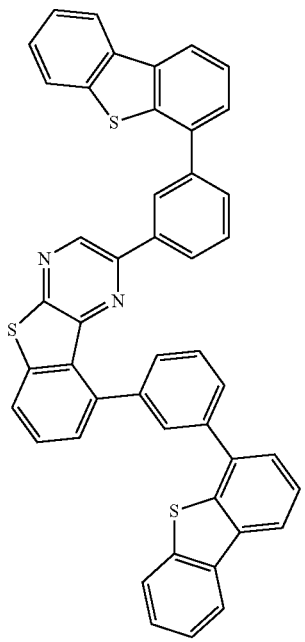
(256)
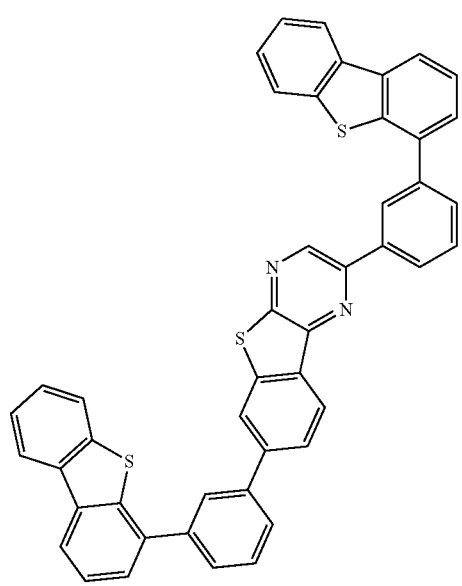

(257)
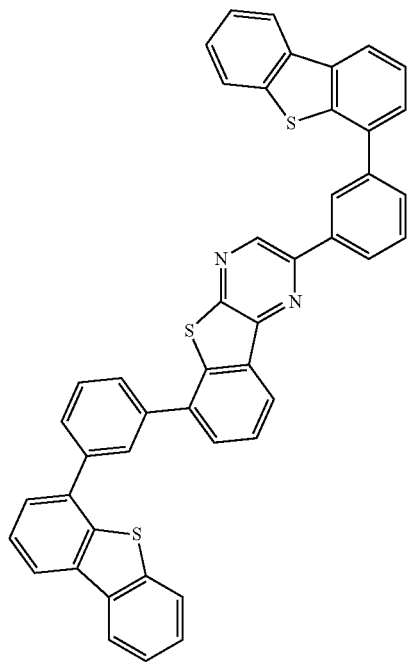
(258)
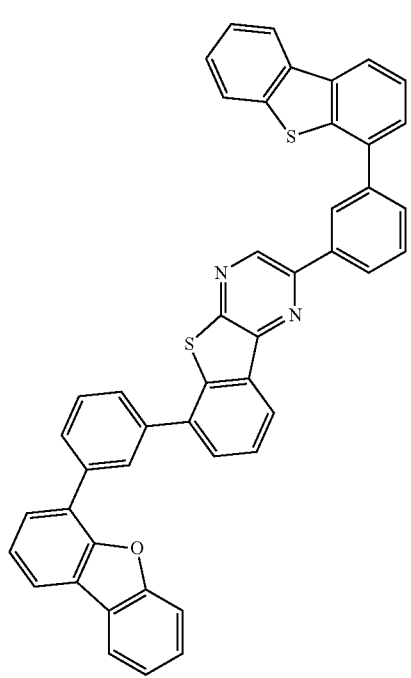
(259)
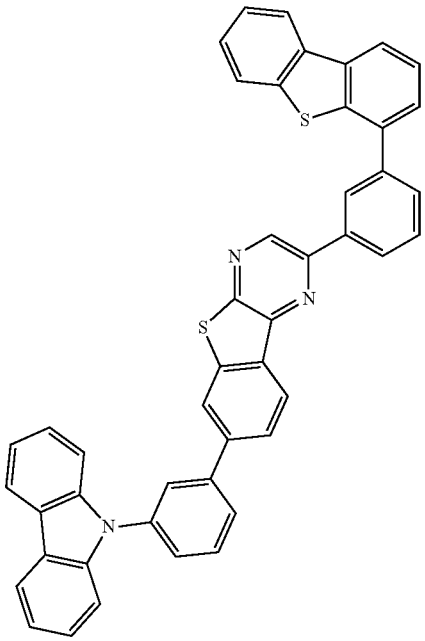
(260)
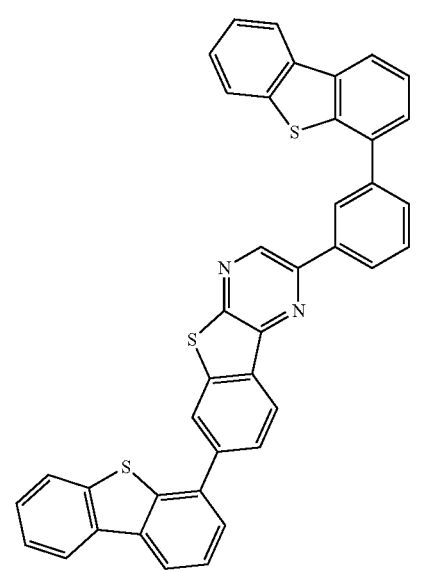

(261)
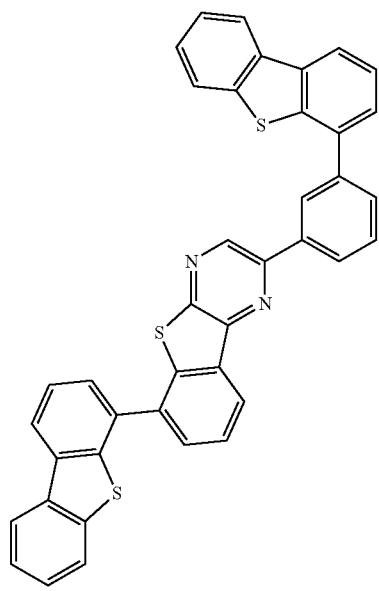
(262)
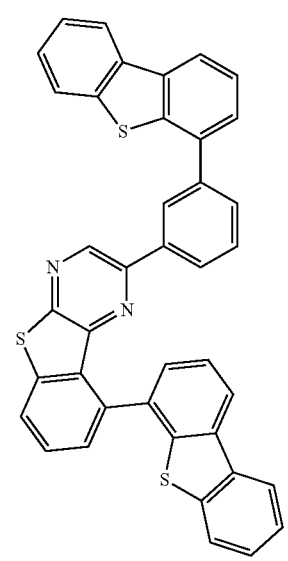
(263)
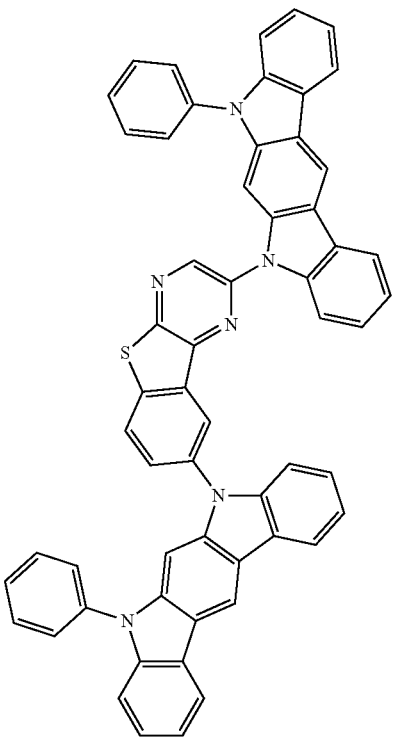
(264)
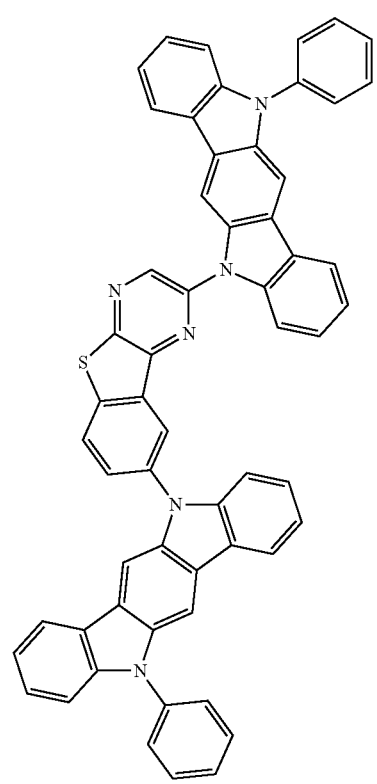

-continued

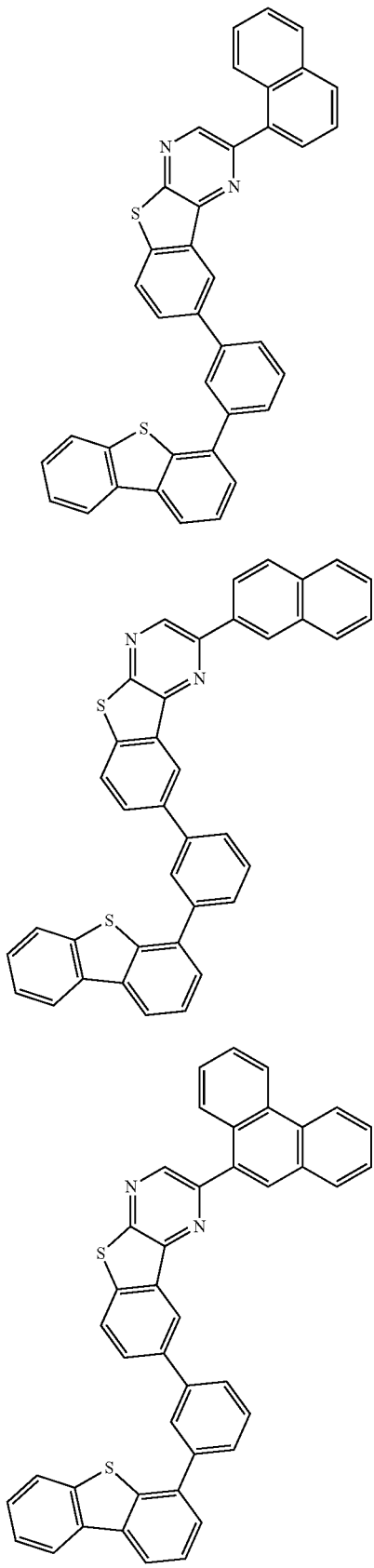

(265)

(266)

(267)

The organic compound of one embodiment of the present invention includes a benzofuropyrazine skeleton or a benzothienopyrazine skeleton. A benzene ring in the benzofuropyrazine skeleton or a benzene ring in the benzothienopyrazine skeleton includes a substituent with a total number of carbon atoms of 6 to 100 inclusive. A pyrazine ring in the benzofuropyrazine skeleton or a pyrazine ring in the benzothienopyrazine skeleton includes a substituent with a total number of carbon atoms of 6 to 100 inclusive.

A light-emitting element including such an organic compound has high emission efficiency and is driven at a low voltage. Since the organic compound has high resistance to repetition of oxidation and reduction and a stable excited state, the light-emitting element including the organic compound can have high reliability.

In general, a compound in which π conjugated systems spread across a molecule (typified by an aromatic compound) is used as a host material or an electron-transport material in the light-emitting element. In particular, a π-electron deficient compound is preferably used. Among π-electron deficient compounds, a condensed heterocyclic skeleton including a diazine skeleton is preferred because of its high T1 level, stability, and high reliability. Particularly, a benzofuropyrazine skeleton and a benzothienopyrazine skeleton are preferred because of its high acceptor property.

Here, the present inventors design the benzene ring side in the benzofuropyrazine skeleton or the benzothienopyrazine skeleton to include the first substituent with a total number of carbon atoms of 6 to 100 inclusive and design the pyrazine ring side in the benzofuropyrazine skeleton or the benzothienopyrazine skeleton to include the second substituent with a total number of carbon atoms of 6 to 100 inclusive. This organic compound can be suitably used as a host material in a light-emitting element. Moreover, the present inventors have found that a light-emitting element including the organic compound as a host material is driven at a low voltage and has high emission efficiency and high reliability.

A light-emitting element in which the benzene ring side in the benzofuropyrazine skeleton or the benzothienopyrazine skeleton includes the first substituent with a total number of carbon atoms of 6 to 100 inclusive has greatly improved reliability as compared with a light-emitting element in which the benzene ring side includes no substituent. This is noticeable particularly when the organic compound of one embodiment of the present invention is used as a host material in a light-emitting layer. This is probably because the substituent included in a benzene ring side in a benzofuropyrazine skeleton or a benzothienopyrazine skeleton improves the stability of an excited state of the organic compound and the stability of film quality. The fact that the substituent in an aromatic ring on the opposite side of a heteroaromatic ring (e.g., a pyrazine ring) brings the effect of increasing the reliability is a major breakthrough by the present inventors. In addition, since the pyrazine ring side in the benzofuropyrazine skeleton or the benzothienopyrazine skeleton includes a second substituent that also has a total number of carbon atoms of 6 to 100 inclusive, carbon and nitrogen of the pyrazine ring are easily protected, so that the electrical stability when electrons are transported and the stability in an excited state can be increased. In the case where the second substituent includes an aromatic ring or a heteroaromatic ring, LUMO is expanded by the interaction with the pyrazine ring, which gives the advantage in an electron-transport property. Therefore, it is preferable that the organic compound include both a substituent on the benzene ring side and a substituent on the pyrazine ring side in the benzofuropyrazine skeleton or the benzothienopyrazine skeleton.

The organic compound of one embodiment of the present invention including a benzofuropyrazine skeleton or a benzothienopyrazine skeleton can be synthesized by a cyclization reaction for obtaining a furan ring or a thiophene ring between a unit including a pyrazine ring and a unit including a benzene ring. The cyclization reaction is preferred because a target substance can be simply obtained at low cost.

Note that the organic compound of one embodiment of the present invention has a high T1 level when the pyrazine ring side in the benzofuropyrazine skeleton or the benzothienopyrazine skeleton includes a substituent at the 2-position and has a low T1 level when the pyrazine ring side includes a substituent at the 3-position. This property is suitable for a host material for a light-emitting substance capable of converting triplet excitation energy into light emission. For example, the T1 level in the case of the 2-position substitution is suitable for the light-emitting substance emitting blue to green light, and the T1 level in the case of the 3-position substitution is suitable for the light-emitting substance emitting red light. Such design flexibility is an effect that is unlikely to be obtained in the case of benzofuropyrimidine.

The organic compound of one embodiment of the present invention including a benzofuropyrazine skeleton or a benzothienopyrazine skeleton has a low LUMO level and a high electron-transport property. Thus, a light-emitting element including the organic compound can be driven at a low voltage. Furthermore, the organic compound has a low LUMO level and has favorable oxidation-reduction characteristics, and thus a light-emitting element including the organic compound can have high reliability.

Since each of the first substituent and the second substituent is independently a substituent with a total number of carbon atoms of 10 to 100 inclusive, a molecular structure with high heat resistance can be achieved, which is preferable. With these substituents, the organic compound of one embodiment of the present invention can have improved stability in an excited state, stability of film quality, and electrical stability when electrons are transported. A typical example of a substituent having 6 carbon atoms is a benzene ring (a phenyl group) or a substituent with a size similar to that of the benzene ring. For example, by replacing this substituent with a substituent which includes a condensed aromatic ring or a condensed heteroaromatic ring and has 10 or more carbon atoms, the above-described effect becomes more significant.

In view of the above, each of the first substituent and the second substituent preferably includes a substituted or unsubstituted aromatic ring having 10 to 30 carbon atoms or a substituted or unsubstituted heteroaromatic ring having 10 to 30 carbon atoms. With such a structure, π conjugated systems can spread across the entire molecule and a molecular structure having a high carrier-transport property can be achieved, so that a highly reliable light-emitting element driven at a low voltage can be provided. Thus, a molecular structure in which a bulky substituent with a total number of carbon atoms of greater than or equal to 10 is included in each of the benzene ring side and the pyrazine ring side in the benzofuropyrazine skeleton or the benzothienopyrazine skeleton is an important structure of one embodiment of the present invention.

In the above structure, examples of the substituted or unsubstituted aromatic ring having 10 to 30 carbon atoms or the substituted or unsubstituted heteroaromatic ring having 10 to 30 carbon atoms include condensed aromatic rings such as a naphthalene ring, a fluorene ring, a phenanthrene ring, and a triphenylene ring. Other examples include a condensed heteroaromatic ring including a carbazole ring, a dibenzofuran ring, or a dibenzothiophene ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring).

Note that examples of the first substituent and the second substituent include an aromatic hydrocarbon group, a heteroaromatic hydrocarbon group, and a substituent including an aromatic amine skeleton. Examples that are more specific include a substituted or unsubstituted benzene ring, a substituted or unsubstituted naphthalene ring, a substituted or unsubstituted phenanthrene ring, a substituted or unsubstituted triphenylene ring, a substituted or unsubstituted condensed heteroaromatic ring having 12 to 30 carbon atoms, and a substituted or unsubstituted triarylamine structure. Light-emitting elements including these substituents can have high reliability because these substituents have high electrochemical stability. The condensed heteroaromatic ring is preferably a ring including a dibenzofuran ring, a dibenzothiophene ring, or a carbazole ring (e.g., a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring) in view of the stability and heat resistance of the ring. The triarylamine structure is preferably a triphenylamine structure, in which case the T1 level is increased.

Note that the number of six-membered heteroaromatic rings having a lone electron-pair, such as pyridine rings, is too large in the first substituent and the second substituent, the organic compound serves as a strong base in the excited state and has low reliability. Therefore, each of the first substituent and the second substituent is preferably formed with one or more of the above-described rings and structure.

Here, the second substituent preferably includes a skeleton having a hole-transport property. Since the benzofuropyrazine skeleton or the benzothienopyrazine skeleton includes the skeleton having a hole-transport property, a highly reliable light-emitting element having high oxidation-reduction characteristics can be provided. Furthermore, the carrier (electrons and holes) transport property is improved, so that the light-emitting element can be driven at a low voltage.

The skeleton having a hole-transport property preferably includes a triarylamine structure or a t-electron rich heteroaromatic ring. An organic compound including a triarylamine structure or a π-electron rich heteroaromatic ring has a high hole-transport property, and thus a light-emitting element including the organic compound can be driven at a low voltage. An example of the t-electron rich heteroaromatic ring is a ring including any of a pyrrole ring, a furan ring, and a thiophene ring. The organic compound preferably has a structure in which the π-electron rich heteroaromatic ring includes any of a dibenzofuran ring, a dibenzothiophene ring, and a carbazole ring, in which case the organic compound has high heat resistance, a stable structure, and a high T1 level. The triarylamine structure is preferably a triphenylamine structure because it has a high hole-transport property. However, the skeleton having a hole-transport property is not limited to these.

The substituent included in the pyrazine ring side in the benzofuropyrazine skeleton or the benzothienopyrazine skeleton may include one or more of arylene groups and skeletons having a hole-transport property, and a terminal of the substituent is preferably a skeleton having a hole-transport property. The substituent of the pyrazine ring side in the benzofuropyrazine skeleton or the benzothienopyrazine skeleton preferably has a structure in which the pyrazine ring and the skeleton having a hole-transport property are directly bonded or a structure in which the skeleton having a hole-transport property is bonded to the benzofuropyrazine skeleton or the benzothienopyrazine skeleton through one or more of arylene groups. An organic compound with such a structure can have a high T1 level.

The substituent included in the pyrazine side in the benzofuropyrazine skeleton or the benzothienopyrazine skeleton preferably includes a substituent at the 2-position. An organic compound with such a structure can have a high T1 level. Note that the substitution site is not limited to the 2-position.

The organic compound of one embodiment of the present invention includes the benzofuropyrazine skeleton having an electron-transport property or the benzothienopyrazine skeleton having an electron-transport property and a substituent having a hole-transport property in one molecule, and thus can be regarded as a bipolar material. This material has a high carrier-transport property and is preferably used as a host material, in which case a light-emitting element using this material can be driven at a low voltage.

The organic compound of one embodiment of the present invention includes a π-electron rich heteroaromatic ring (e.g., a dibenzofuran skeleton, a dibenzothiophene skeleton, or a carbazole skeleton) and a π-electron deficient heteroaromatic ring (a benzofuropyrazine skeleton or a benzothienopyrazine skeleton). Accordingly, a donor-acceptor excited state is easily formed in a molecule. Furthermore, the π-electron rich heteroaromatic ring and the π-electron deficient heteroaromatic ring are bonded directly or through an arylene group, which can improve both the donor property and the acceptor property. By increasing both the donor property and the acceptor property in the molecule, an overlap between a region where the highest occupied molecular orbital (HOMO) is distributed and a region where the LUMO is distributed can be small, and the energy difference between the singlet excitation energy level and the triplet excitation energy level of the compound can be small. Moreover, the triplet excitation energy level of the compound can be kept high. Note that a molecular orbital refers to spatial distribution of electrons in a molecule, and can show the probability of finding of electrons. With the molecular orbital, the electron configuration of the molecule (the spatial distribution and energy of electrons) can be described in detail.

When a difference between the singlet excitation energy level and the triplet excitation energy level is small, with low thermal energy at 100° C. or lower, preferably at approximately room temperature, the triplet excitation energy can be upconverted to the singlet excitation energy by reverse intersystem crossing. That is, the compound of one embodiment of the present invention is suitable as a compound having a function of converting triplet excitation energy into singlet excitation energy. In addition, the compound is suitable as a compound having a function of converting triplet excitation energy into singlet excitation energy and converting the singlet excitation energy into light emission. For efficient reverse intersystem crossing, the difference between the singlet excitation energy level and the triplet excitation energy level is preferably greater than 0 eV and less than or equal to 0.3 eV, more preferably greater than 0 eV and less than or equal to 0.2 eV, still more preferably greater than 0 eV and less than or equal to 0.1 eV.

Note that when the region where the HOMO is distributed and the region where the LUMO is distributed overlap each other and transition dipole moment between the HOMO level and the LUMO level is larger than 0, light emission can be obtained from an excited state related to the HOMO level and the LUMO level (e.g., the lowest singlet excited state). Therefore, the compound of one embodiment of the present invention is suitable as a light-emitting material having a function of converting the triplet excitation energy into the singlet excitation energy; in other words, the compound is suitable as a thermally activated delayed fluorescence material.

As described above, the organic compound of one embodiment of the present invention is suitable as a host material for a light-emitting substance capable of converting triplet excitation energy into light emission. Accordingly, a light-emitting element including an EL layer between a pair of electrodes, in which the EL layer includes a substance including the benzofuropyrazine skeleton or the benzothienopyrazine skeleton and includes a light-emitting layer and the light-emitting layer includes a substance including the benzofuropyrazine skeleton or the benzothienopyrazine skeleton and a substance capable of converting triplet excitation energy into light emission, is also one embodiment of the present invention. At this time, the substance capable of converting triplet excitation energy into light emission is preferably a phosphorescent compound to be described later.

Note that a film of the organic compound of this embodiment can be formed by an evaporation method (including a vacuum evaporation method), an inkjet method, a coating method, a gravure printing method, or the like.

Note that this embodiment can be combined with any of the other embodiments as appropriate.

Embodiment 2

In this embodiment, a method for synthesizing the benzofuropyrazine compound or benzothienopyrazine compound, which is an organic compound of one embodiment of the present invention and represented by General Formula (G0), will be described. A variety of reactions can be applied to the method for synthesizing the compound. For example, the compound represented by General Formula (G0) can be synthesized through simple synthesis schemes shown below.

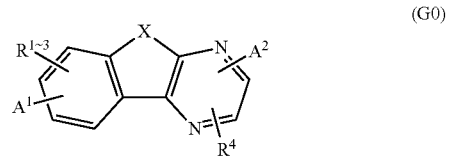

(G0)

First, a benzofuropyrazine compound or benzothienopyrazine compound represented by (M-1), which is a starting material of General Formula (G0), can be synthesized through Synthesis Scheme (A-1) shown below. An intermediate (Am-3) can be obtained by coupling of a methyloxy group-substituted or methylthio group-substituted aryl boronic acid (m-1) and an amino group-substituted and halogen-substituted pyrazine compound (m-2). By a cyclization reaction of this intermediate with tert-butyl nitrite, the benzofuropyrazine compound or benzothienopyrazine compound represented by (M-1) can be obtained.

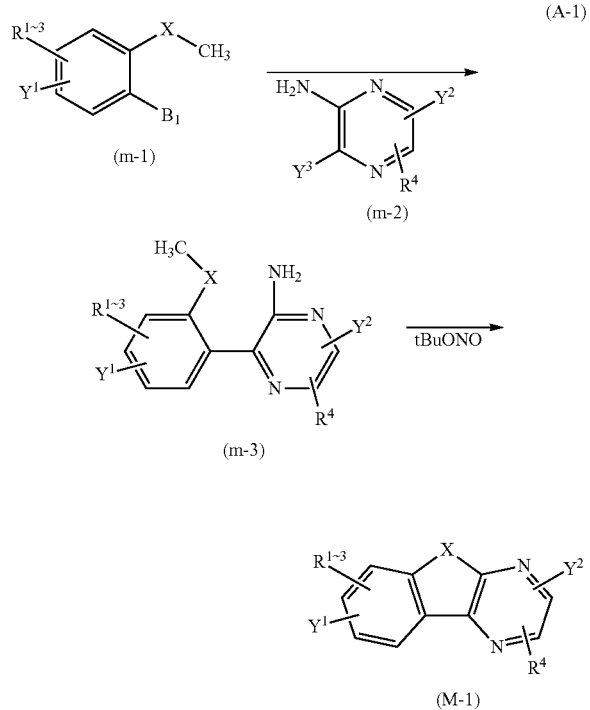

(A-1)

(m-1)

(m-2)

(m-3)

(M-1)

In Synthesis Scheme (A-1), X represents oxygen or sulfur, and each of $Y^1$ and $Y^2$ independently represents halogen; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; and $B_1$ represents a boronic acid, a boronic ester, a cyclic-triolborate salt, or the like. As the cyclic-triolborate salt, a lithium salt, a potassium salt, or a sodium salt may be used.

Next, the benzofuropyrazine compound or benzothienopyrazine compound, which is an organic compound of one embodiment of the present invention and represented by General Formula (G0), can be obtained by coupling of the benzofuropyrazine compound or benzothienopyrazine compound represented by (M-1) obtained through Synthesis Scheme (A-1) and the boronic acid compounds (M-2) and (M-3) as shown in Synthesis Scheme (A-2). Alternatively, the benzofuropyrazine compound or benzothienopyrazine compound represented by General Formula (G0) can be obtained by coupling of an intermediate, which is obtained by coupling of the benzofuropyrazine compound or benzothienopyrazine compound represented by (M-1) and the boronic acid compound (M-3), and the boronic acid compound (M-2).

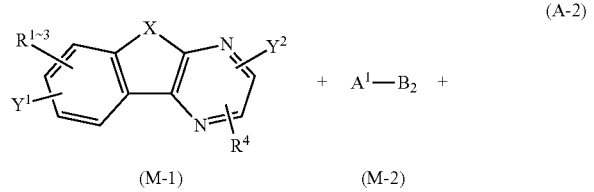

(A-2)

(M-1)    (M-2)

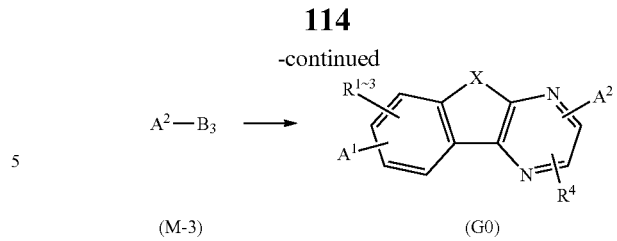

(M-3)    (G0)

In Synthesis Scheme (A-2), X represents oxygen or sulfur, and each of $A^1$ and $A^2$ independently represents a substituent having 6 to 100 carbon atoms; each of $R^1$ to $R^4$ independently represents hydrogen, an alkyl group having 1 to 6 carbon atoms, a substituted or unsubstituted cycloalkyl group having 3 to 7 carbon atoms, or a substituted or unsubstituted aryl group having 6 to 25 carbon atoms; each of $Y^1$ and $Y^2$ independently represents halogen; and each of $B_2$ and $B_3$ independently represents a boronic acid, a boronic ester, a cyclic-triolborate salt, or the like. As the cyclic-triolborate salt, a lithium salt, a potassium salt, or a sodium salt may be used.

Since various kinds of the above-described compounds (m-1), (m-2), (M-2), and (M-3) are commercially available or can be synthesized, various kinds of the benzofuropyrazine compound or benzothienopyrazine compound represented by General Formula (G0) can be synthesized. Thus, a feature of the compound of one embodiment of the present invention is the abundance of variations.

Examples of methods for synthesizing the benzofuropyrazine compound or benzothienopyrazine compound of one embodiment of the present invention are described above, but the present invention is not limited to these methods and any other synthesis methods can be employed.

Note that the compound described in this embodiment can be used in combination with any of the structures described in the other embodiments as appropriate.

Embodiment 3

In this embodiment, a light-emitting element of one embodiment of the present invention will be described below with reference to FIGS. 1A to 1C.

<Structure Example 1 of Light-Emitting Element>

First, a structure of the light-emitting element of one embodiment of the present invention will be described with reference to FIGS. 1A to 1C.

FIG. 1A is a schematic cross-sectional view of a light-emitting element 150 of one embodiment of the present invention.

The light-emitting element 150 includes a pair of electrodes (an electrode 101 and an electrode 102) and an EL layer 100 between the pair of electrodes. The EL layer 100 includes at least a light-emitting layer 140.

The EL layer 100 illustrated in FIG. 1A includes functional layers such as a hole-injection layer 111, a hole-transport layer 112, an electron-transport layer 118, and an electron-injection layer 119, in addition to the light-emitting layer 140.

In this embodiment, although description is given assuming that the electrode 101 and the electrode 102 of the pair of electrodes serve as an anode and a cathode, respectively, they are not limited thereto for the structure of the light-emitting element 150. That is, the electrode 101 may be a cathode, the electrode 102 may be an anode, and the stacking order of the layers between the electrodes may be reversed. In other words, the hole-injection layer 111, the hole-transport layer 112, the light-emitting layer 140, the electron-transport layer 118, and the electron-injection layer 119 may be stacked in this order from the anode side.

The structure of the EL layer 100 is not limited to the structure illustrated in FIG. 1A, and a structure including at least one layer selected from the hole-injection layer 111, the hole-transport layer 112, the electron-transport layer 118, and the electron-injection layer 119 may be employed. Alternatively, the EL layer 100 may include a functional layer which is capable of lowering a hole- or electron-injection barrier, improving a hole- or electron-transport property, inhibiting a hole- or electron-transport property, or suppressing a quenching phenomenon by an electrode, for example. Note that the functional layers may each be a single layer or stacked layers.

In the light-emitting element 150, at least one of the layers in the EL layer 100 contains the organic compound of one embodiment of the present invention. Note that the layer containing the organic compound is preferably the electron-transport layer 118, and more preferably the light-emitting layer 140. Furthermore, as described above, it is preferable that the organic compound of one embodiment of the present invention be used as a host material 141 in the light-emitting layer 140 and a substance capable of converting triplet excitation energy into light emission (in particular, a phosphorescent compound) be used as a guest material 142.

Figure 1B:
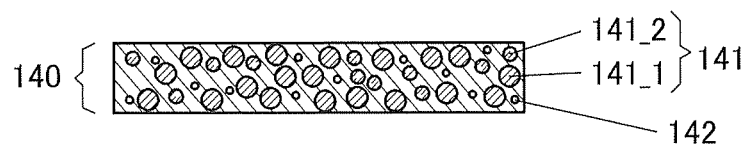

FIG. 1B is a schematic cross-sectional view illustrating an example of the light-emitting layer 140 in FIG. 1A. The light-emitting layer 140 in FIG. 1B includes a host material 141 and a guest material 142. The host material 141 may be a single organic compound or a co-host system including an organic compound 141_1 and an organic compound 141_2. The organic compound of one embodiment of the present invention can be used as the host material 141 or the organic compound 141_1.

The guest material 142 is a light-emitting organic material, and as examples of the light-emitting organic material, a material capable of emitting fluorescence (hereinafter referred to as a fluorescent material) and a material capable of emitting phosphorescence (hereinafter also referred to as a phosphorescent material) can be given. A structure in which a phosphorescent material is used as the guest material 142 will be described below. The guest material 142 may be rephrased as the phosphorescent material.

In the case where two kinds of host materials such as the organic compound 141_1 and the organic compound 141_2 are used (co-host system) in the light-emitting layer as illustrated in FIG. 1B, one electron-transport material and one hole-transport material are generally used as the two kinds of host materials. Such a structure, with which a hole-injection barrier between the hole-transport layer 112 and the light-emitting layer 140 and an electron-injection barrier between the electron-transport layer 118 and the light-emitting layer 140 are reduced and thus the driving voltage can be reduced, is preferable.

<Light Emission Mechanism of Light-Emitting Element>

Next, the light emission mechanism of the light-emitting layer 140 is described below.

The organic compound 141_1 and the organic compound 141_2 included in the host material 141 in the light-emitting layer 140 form an excited complex (also referred to as exciplex).

Figure 1C:
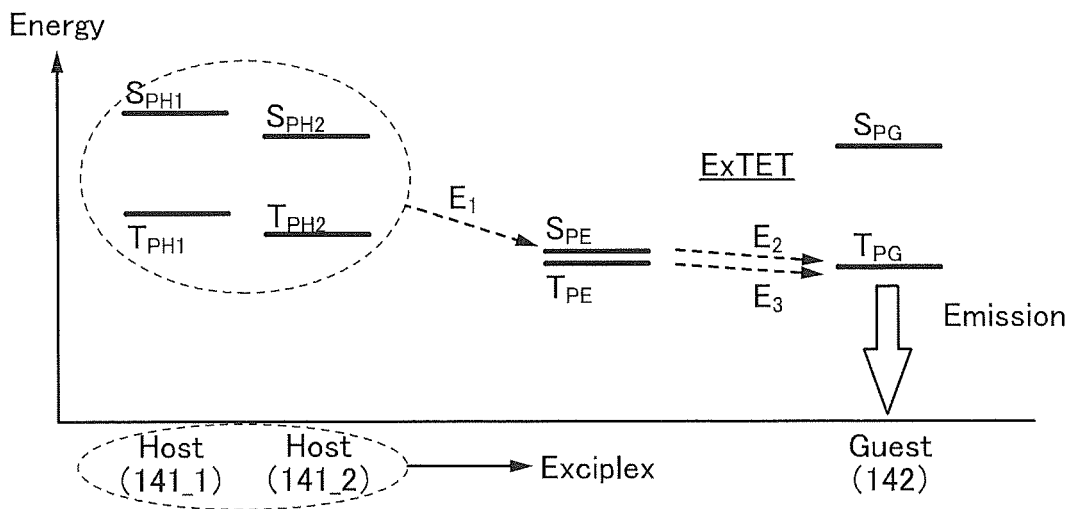

FIG. 1C shows a correlation between the energy levels of the organic compound 141_1, the organic compound 141_2, and the guest material 142 in the light-emitting layer 140. The following explains what terms and numerals in FIG. 1C represent:

Host (141_1): the organic compound 141_1 (host material);
Host (141_2): the organic compound 141_2 (host material);
Guest (142): the guest material 142 (the phosphorescent compound);
$S_{PH1}$: the S1 level of the organic compound 141_1 (host material);
$T_{PH1}$: the T1 level of the organic compound 141_1 (host material);
$S_{PH2}$: the S1 level of the organic compound 141_2 (host material);
$T_{PH2}$: the T1 level of the organic compound 141_2 (host material);
$S_{PG}$: the S1 level of the guest material 142 (the phosphorescent compound);
$T_{PG}$: the T1 level of the guest material 142 (the phosphorescent compound);
$S_{PE}$: the S1 level of the exciplex; and
$T_{PE}$: the T1 level of the exciplex.

The organic compound 141_1 and the organic compound 141_2 form an exciplex, and the S1 level ($S_{PE}$) and the T1 level ($T_{PE}$) of the exciplex are energy levels close to each other (see Route $E_1$ in FIG. 1C).

One of the organic compound 141_1 and the organic compound 141_2 receives a hole and the other receives an electron to readily form an exciplex. Alternatively, when one of the organic compounds is brought into an excited state, the other immediately interacts with the one to form an exciplex. Consequently, most excitons in the light-emitting layer 140 exist as exciplexes. Because the excitation energy levels ($S_{PE}$ and $T_{PE}$) of the exciplex are lower than the S1 levels ($S_{PH1}$ and $S_{PH2}$) of the host materials (the organic compounds 141_1 and 141_2) that form the exciplex, the excited state of the host material 141 can be formed with lower excitation energy. This can reduce the driving voltage of the light emitting element.

Both energies of $S_{PE}$ and $T_{PE}$ of the exciplex are then transferred to the T1 level of the guest material 142 (the phosphorescent compound); thus, light emission is obtained (see Routes $E_2$ and $E_3$ in FIG. 1C).

Furthermore, the T1 level ($T_{PE}$) of the exciplex is preferably higher than the T1 level ($T_{PG}$) of the guest material 142. In this way, the singlet excitation energy and the triplet excitation energy of the formed exciplex can be transferred from the S1 level ($S_{PE}$) and the T1 level ($T_{PE}$) of the exciplex to the T1 level ($T_{PG}$) of the guest material 142.

Note that in order to efficiently transfer excitation energy from the exciplex to the guest material 142, the T1 level ($T_{PE}$) of the exciplex is preferably lower than or equal to the T1 levels ($T_{PH1}$ and $T_{PH2}$) of the organic compounds (the organic compound 141_1 and the organic compound 141_2) which form the exciplex. Thus, quenching of the triplet excitation energy of the exciplex due to the organic compounds (the organic compounds 141_1 and 141_2) is less likely to occur, resulting in efficient energy transfer from the exciplex to the guest material 142.

In the case where the combination of the organic compounds 141_1 and 141_2 is a combination of a compound having a hole-transport property and a compound having an electron-transport property, the carrier balance can be easily controlled depending on the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

The above-described processes through Routes $E_2$ and $E_3$ may be referred to as exciplex-triplet energy transfer (Ex-TET) in this specification and the like. In other words, in the light-emitting layer 140, excitation energy is given from the exciplex to the guest material 142. In this case, the efficiency of reverse intersystem crossing from $T_{PE}$ to $S_{PE}$ and the emission quantum yield from $S_{PE}$ are not necessarily high; thus, materials can be selected from a wide range of options.

Although it is acceptable as long as the combination of the organic compound 141_1 and the organic compound 141_2 can form an exciplex, it is preferable that one have a lower HOMO) level and a lower LUMO (lowest unoccupied molecular orbital) level than the other.

<Material>

Next, components of a light-emitting element of one embodiment of the present invention are described in detail below.

«Light-Emitting Layer»

In the light-emitting layer 140, the host material 141 is present in the largest proportion by weight, and the guest material 142 is dispersed in the host material 141. When the guest material 142 is a fluorescent compound, the S1 level of the host material 141 (the organic compound 141_1 and the organic compound 141_2) in the light-emitting layer 140 is preferably higher than the S1 level of the guest material (the guest material 142) in the light-emitting layer 140. When the guest material 142 is a phosphorescent compound, the T1 level of the host material 141 (the organic compound 141_1 and the organic compound 141_2) in the light-emitting layer 140 is preferably higher than the T1 level of the guest material (the guest material 142) in the light-emitting layer 140.

The organic compound 141_1 is preferably a compound having a nitrogen-containing six-membered heteroaromatic skeleton. In particular, the organic compound of one embodiment of the present invention can be suitably used because it includes a pyrazine skeleton. Other specific examples thereof include compounds having any of a pyridine skeleton, a diazine skeleton (a pyrazine skeleton, a pyrimidine skeleton, and a pyridazine skeleton), and a triazine skeleton. As examples of these basic compounds having a nitrogen-containing heteroaromatic skeleton, compounds such as a pyridine compound, a bipyridine compound, a pyrimidine compound, a triazine compound, a quinoxaline compound, a dibenzoquinoxaline compound, a phenanthroline compound, and a purine compound can be given. As the organic compound 141_1, a material having a property of transporting more electrons than holes (an electron-transport material) can be used, and a material having an electron mobility of $1 \times 10^{-6}$ cm$^2$/Vs or higher is preferable.

Specific examples include heterocyclic compounds having a pyridine skeleton such as bathophenanthroline (abbreviation:BPhen) and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[fh]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-tria zine (abbreviation: PCCzPTzn); and heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the heterocyclic compounds, the heterocyclic compounds having a triazine skeleton, a diazine (pyrimidine, pyrazine, pyridazine) skeleton, or a pyridine skeleton are highly reliable and stable and are thus preferably used. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1 \times 10^{-6}$ cm$^2$/Vs or higher. Note that other substances may also be used as long as their electron-transport properties are higher than their hole-transport properties.

The organic compound 141_2 is preferably a compound having a nitrogen-containing five-membered heterocyclic skeleton or a tertiary amine skeleton. Specific examples thereof include compounds having any of a pyrrole skeleton and an aromatic amine skeleton. As examples, an indole compound, a carbazole compound, a triarylamine compound, and the like can be given. Examples of a nitrogen-containing five-membered heterocyclic skeleton include an imidazole skeleton, a triazole skeleton, and a tetrazole skeleton. As the organic compound 141_2, a material having a property of transporting more holes than electrons (a hole-transport material) can be used, and a material having a hole mobility of $1 \times 10^{-6}$ cm$^2$/Vs or higher is preferable. Furthermore, the hole-transport material may be a high molecular compound.

Examples of the aromatic amine compounds that can be used as the material having a high hole-transport property are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole compound are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole compound are 4,4'-di(N-carbazolyl)biphenyl (abbreviation: CBP), 1,3,5-tris[4-(N-carbazolyl)phenyl]benzene (abbreviation: TCPB), 9-[4-(10- phenyl-9-anthryl)phenyl]-9H-carbazole (abbreviation: CzPA), and 1,4-bis[4-(N-carbazolyl)phenyl]-2,3,5,6-tetraphenylbenzene.

Furthermore, it is possible to use N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), N,N,N',N',N'',N'',N''',N'''-octaphenyldibenzo[g,p]chrysene-2,7,10,15-tetraamine (abbreviation: DBC1), or the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacryla mide] (abbreviation: PTPDMA), and poly[N,N'-bis(4-butylphenyl)-N,N'-bis(phenyl)benzidine] (abbreviation: poly-TPD).

Examples of the material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris[N-(1-naphthyl)-N-phenylamino]triphenylamine (abbreviation: 1'-TNATA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino] spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl) triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluor en-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are amine compounds, carbazole compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), and 2,8-di(9H-carbazol-9-yl)-dibenzothiophene (abbreviation: Cz2DBT). Among the above compounds, compounds having a pyrrole skeleton or an aromatic amine skeleton are preferred because of their high stability and reliability. In addition, the compounds having such skeletons have a high hole-transport property to contribute to a reduction in driving voltage.

As the organic compound 141_2, a compound having a nitrogen-containing five-membered heterocyclic skeleton such as an imidazole skeleton, a triazole skeleton, or a tetrazole skeleton can be used. Specifically, 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and the like can be used, for example.

Although the guest material 142 in the light-emitting layer 140 is not particularly limited, when the guest material 142 is a fluorescent compound, an anthracene compound, a tetracene compound, a chrysene compound, a phenanthrene compound, a pyrene compound, a perylene compound, a stilbene compound, an acridone compound, a coumalin compound, a phenoxazine compound, a phenothiazine compound, or the like is preferred. For example, the following substances can be used.

Specifically, the following examples can be given: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl] pyrene-1,6-diamine (abbreviation: 1,6FLPAPrn), N,N'-bis (3-methylphenyl)-N,N'-bis[3-(9-phenyl-9H-fluoren-9-yl) phenyl]pyrene-1,6-dia mine (abbreviation: 1,6mMemFLPAPm), N,N'-bis[4-(9-phenyl-9H-fluoren-9-yl)phenyl]-N,N'-bis(4-tert-butylphenyl)pyrene-1,6-d iamine (abbreviation: 1,6tBu-FLPAPrn), N,N'-diphenyl-N,N'-bis[4-(9-phenyl-9H-fluoren-9-yl)phenyl]-3,8-dicyclohexylpyrene-1, 6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-pheny lenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd:1',2', 3'-lm]perylene.

As the guest material 142 (phosphorescent compound), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

Examples of the substance that has an emission peak in the blue or green wavelength range include organometallic iridium complexes having a 4H-triazole skeleton, such as tris {2-[5-(2-methylphenyl)-4-(2,6-dimethylphenyl)-4H-1,2,4-triazol-3-yl-κN2]phenyl-κ C}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium(III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium(III) (abbreviation: Ir(Mptz 1-mp)$_3$) and tris(1-methyl-5-phenyl-3-propyl-1H-1,2,4-triazolato)iridium(III) (abbreviation: Ir(Prptzl-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine compound having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: FIr(acac)). Among the materials given above, the organometallic iridium complexes including a nitrogen-containing five-membered heterocyclic skeleton, such as a 4H-triazole skeleton, a 1H-triazole skeleton, or an imidazole skeleton have high triplet excitation energy, reliability, and emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN3]pheny 1-κC}iridium(III) (abbreviation: Ir(dmppm-dmp)$_2$(acac)), and (acetylacetonato)bis(4,6-diphenylpyrimidinato)iridium (III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium (III) acetylacetonate (abbreviation: Ir(ppy)$_2$(acac)), bis (benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), and bis(2-phenylquinolinato-N,C$^{2'}$)iridium(III) acetylacetonate (abbreviation: Ir(pq)$_2$(acac)); organometallic iridium complexes such as bis(2,4-diphenyl-1,3-oxazolato-N,C$^{2'}$)iridium (III) acetylacetonate (abbreviation: Ir(dpo)$_2$(acac)), bis{2-[4'-(perfluorophenyl)phenyl]pyridinato-N,C$^{2'}$ }iridium(III) acetylacetonate (abbreviation: Ir(p-PF-ph)$_2$(acac)), and bis (2-phenylbenzothiazolato-N,C$^{2'}$)iridium(III) acetylacetonate (abbreviation: Ir(bt)$_2$(acac)); and a rare earth metal complex such as tris(acetylacetonato)(monophenanthroline) terbium(III) (abbreviation: Tb(acac)$_3$(Phen)). Among the materials given above, the organometallic iridium complexes having a pyrimidine skeleton have distinctively high reliability and light emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(dlnpm)$_2$(dpm)); organometallic iridium complexes having a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N,C$^{2'}$)iridium(III) (abbreviation: Ir(piq)$_3$) and bis(1-phenylisoquinolinato-N,C$^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: Eu(DBM)$_3$(Phen)) and tris[1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and light emission efficiency and are thus particularly preferable. Further, the organometallic iridium complexes having a pyrazine skeleton can provide red light emission with favorable chromaticity.

An organic compound including a benzofuropyrazine skeleton or a benzothienopyrazine skeleton has a high T1 level, and thus can be suitably used as a host material in a light-emitting layer containing a substance capable of converting triplet excitation energy into light emission as a light-emitting material. Accordingly, the light-emitting material included in the light-emitting layer 140 is preferably a material that can convert the triplet excitation energy into light emission. As an example of the material that can convert the triplet excitation energy into light emission, a thermally activated delayed fluorescence (TADF) material can be given in addition to the above-described phosphorescent compound. Therefore, it is acceptable that the "phosphorescent compound" in the description is replaced with the "thermally activated delayed fluorescence material". Note that the thermally activated delayed fluorescence material is a material having a small difference between the triplet excitation energy level and the singlet excitation energy level and a function of converting triplet excitation energy into singlet excitation energy by reverse intersystem crossing. Thus, the TADF material can up-convert a triplet excited state into a singlet excited state (i.e., reverse intersystem crossing is possible) using a little thermal energy and efficiently exhibit light emission (fluorescence) from the singlet excited state. The TADF is efficiently obtained under the condition where the difference in energy between the triplet excitation energy level and the singlet excitation energy level is preferably larger than 0 eV and smaller than or equal to 0.2 eV, further preferably larger than 0 eV and smaller than or equal to 0.1 eV. As the thermally activated delayed fluorescence material, the compound described in Embodiment 1 is also preferably used.

In the case where the thermally activated delayed fluorescence material is composed of one kind of material, any of the following materials can be used, for example.

First, a fullerene, a compound thereof, an acridine compound such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)).

As the thermally activated delayed fluorescence material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-tria zine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H, 10'H-spiro[acridin-9,9'-anthracen]-10'-one (abbreviation: ACRSA), or the like can be used. The heterocyclic compound is preferable because of having the π-electron rich heteroaromatic ring and the π-electron deficient heteroaromatic ring, for which the electron-transport property and the hole-transport property are high. Among skeletons having the t-electron deficient heteroaromatic ring, a diazine skeleton (a pyrimidine skeleton, a pyrazine skeleton, or a pyridazine skeleton) and a triazine skeleton have high stability and reliability and are particularly preferable. Among skeletons having the π-electron rich heteroaromatic ring, an acridine skeleton, a phenoxazine skeleton, a thiophene skeleton, a furan skeleton, and a pyrrole skeleton have high stability and reliability; therefore, one or more of these skeletons are preferably included. As the pyrrole skeleton, an indole skeleton, a carbazole skeleton, or a 3-(9-phenyl-9H-carbazol-3-yl)-9H-carbazole skeleton is particularly preferred. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both increased and the difference between the energy level in the singlet excited state and the energy level in the triplet excited state becomes small.

The light-emitting layer 140 may include a material other than the host material 141 and the guest material 142.

Examples of the material that can be used for the light-emitting layer 140 are, but not limited to, condensed polycyclic aromatic compounds such as anthracene compounds, phenanthrene compounds, pyrene compounds, chrysene compounds, and dibenzo[g,p]chrysene compounds. Specific example of the condensed polycyclic aromatic compounds include 9,10-diphenylanthracene (abbreviation: DPAnth), 6,12-dimethoxy-5,11-diphenylchrysene, 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a singlet excitation energy level or a triplet excitation energy level higher than the excitation energy level of the guest material 142 are selected from these substances and known substances.

For example, a compound having a heteroaromatic skeleton, such as an oxadiazole compound, can be used for the light-emitting layer 140. As specific examples thereof, heterocyclic compounds such as 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), and 4,4'-bis (5-methylbenzoxazol-2-yl)stilbene (abbreviation: BzOs) can be given.

In addition, a metal complex (e.g., a zinc- or aluminum-based metal complex) with a heterocycle, for example, can be used for the light-emitting layer 140. As examples, metal complexes having a quinoline ligand, a benzoquinoline ligand, an oxazole ligand, and a thiazole ligand can be given. Specific examples thereof include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato) aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used.

The light-emitting layer 140 can have a structure in which two or more layers are stacked. For example, in the case where the light-emitting layer 140 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. A light-emitting material included in the first light-emitting layer may be the same as or different from a light-emitting material included in the second light-emitting layer. In addition, the materials may have functions of emitting light of the same color or light of different colors. Light-emitting materials having functions of emitting light of different colors are used for the two light-emitting layers, so that light of a plurality of emission colors can be obtained at the same time. It is particularly preferable to select light-emitting materials of the light-emitting layers so that white light can be obtained by combining light emission from the two light-emitting layers.

Note that the light-emitting layer 140 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

«Hole-Injection Layer»

The hole-injection layer 111 has a function of reducing a barrier for hole injection from one of the pair of electrodes (the electrode 101 or the electrode 102) to promote hole injection and is formed using a transition metal oxide, a phthalocyanine compound, or an aromatic amine, for example. As the transition metal oxide, molybdenum oxide, vanadium oxide, ruthenium oxide, tungsten oxide, manganese oxide, and the like can be given. As the phthalocyanine compound, phthalocyanine, metal phthalocyanine, and the like can be given. As the aromatic amine, a benzidine compound, a phenylenediamine compound, and the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron-accepting property and a layer containing a hole-transport material may also be used. In a steady state or in the presence of an electric field, electric charge can be transferred between these materials. As examples of the material having an electron-accepting property, organic acceptors such as a quinodimethane compound, a chloranil compound, and a hexaazatriphenylene compound can be given. A specific example is a compound having an electron-withdrawing group (a halogen group or a cyano group), such as 7,7,8,8-tetracyano-2,3,5;6-tetrafluoroquinodimethane (abbreviation: F$_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ cm$^2$/Vs or higher is preferable. Specifically, any of the aromatic amine, carbazole compound, aromatic hydrocarbon, stilbene compound, and the like described as examples of the hole-transport material that can be used in the light-emitting layer 140 can be used. Furthermore, the hole-transport material may be a high molecular compound.

As other examples of the hole-transport material, aromatic hydrocarbons such as 2-tert-butyl-9,10-di(2-naphthyl) anthracene (abbreviation: t-BuDNA), 2-tert-butyl-9,10-di(1-naphthyl)anthracene, 9,10-bis(3,5-diphenylphenyl) anthracene (abbreviation: DPPA), 2-tert-butyl-9,10-bis(4-phenylphenyl)anthracene (abbreviation: t-BuDBA), 9,10-di (2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9, 10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5, 8,11-tetra(tert-butyl)perylene can be given. Other examples are pentacene, coronene, and the like. The aromatic hydrocarbon having a hole mobility of $1 \times 10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation:

DPVBi), 9,10-bis[4-(2,2-diphenylvinyl)phenyl]anthracene (abbreviation: DPVPA), and the like.

Other examples are thiophene compounds, furan compounds, fluorene compounds, triphenylene compounds, phenanthrene compounds, and the like such as 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Among the above compounds, compounds including a pyrrole skeleton, a furan skeleton, a thiophene skeleton, or an aromatic amine skeleton are preferred because of their high stability and reliability. In addition, the compounds having such skeletons have a high hole-transport property to contribute to a reduction in driving voltage.

«Hole-Transport Layer»

The hole-transport layer 112 is a layer containing a hole-transport material and can be formed using any of the hole-transport materials given as examples of the material of the hole-injection layer 111. In order that the hole-transport layer 112 can have a function of transporting holes injected into the hole-injection layer 111 to the light-emitting layer 140, the highest occupied molecular orbital (HOMO) level of the hole-transport layer 112 is preferably equal or close to the HOMO level of the hole-injection layer 111.

As the hole-transport material, a substance having a hole mobility of $1 \times 10^{-6}$ cm$^2$/Vs or higher is preferably used. Note that any substance other than the above substances may be used as long as the hole-transport property is higher than the electron-transport property. The layer including a substance having a high hole-transport property is not limited to a single layer, and two or more layers containing the aforementioned substances may be stacked.

«Electron-Transport Layer»

The electron-transport layer 118 has a function of transporting, to the light-emitting layer 140, electrons injected from the other of the pair of electrodes (the electrode 101 or the electrode 102) through the electron-injection layer 119. A material having a property of transporting more electrons than holes can be used as the electron-transport material, and a material having an electron mobility of $1 \times 10^{-6}$ cm$^2$/Vs or higher is preferable. As a compound that easily accepts electrons (a material having an electron-transport property), a π-electron deficient heteroaromatic compound such as a nitrogen-containing heteroaromatic compound or a metal complex can be used. The organic compound of one embodiment of the present invention can be suitably used because it includes a pyrazine skeleton. Other specific examples of the material having an electron-transport property include a pyridine compound, a bipyridine compound, a pyrimidine compound, a triazine compound, a quinoxaline compound, a dibenzoquinoxaline compound, a phenanthroline compound, a triazole compound, a benzimidazole compound, and an oxadiazole compound, which are described above as the electron-transport material that can be used for the light-emitting layer 140. A substance having an electron mobility of $1 \times 10^{-6}$ cm$^2$/Vs or higher is preferable. Note that other than these substances, any substance that has a property of transporting more electrons than holes may be used for the electron-transport layer. The electron-transport layer 118 is not limited to a single layer, and may include stacked two or more layers containing the aforementioned substances.

In addition, metal complexes with a heterocycle, such as metal complexes having a quinoline ligand, a benzoquinoline ligand, an oxazole ligand, and a thiazole ligand, can be given. Specific examples thereof include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used.

Between the electron-transport layer 118 and the light-emitting layer 140, a layer that controls transfer of electron carriers may be provided. This is a layer formed by addition of a small amount of a substance having a high electron-trapping property to a material having a high electron-transport property as described above, and the layer is capable of adjusting carrier balance by suppressing transport of electron carriers. Such a structure is very effective in suppressing a problem (e.g., a decrease in element lifetime) which occurs in the case where the electron-transport property of the electron-transport material is significantly higher than the hole-transport property of the hole-transport material.

«Electron-Injection Layer»

The electron-injection layer 119 has a function of reducing a barrier for electron injection at an interface between the electron-injection layer 119 and the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, and the like can be given. Specifically, an alkali metal, an alkaline earth metal, or a compound thereof, such as lithium fluoride (LiF), sodium fluoride (NaF), cesium fluoride (CsF), calcium fluoride (CaF$_2$), or lithium oxide (LiO$_x$), can be used. Alternatively, a rare earth metal compound like erbium fluoride (ErF$_3$) can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

«Quantum Dot»

A quantum dot is a semiconductor nanocrystal with a size of several nanometers to several tens of nanometers and contains approximately $1 \times 10^3$ to $1 \times 10^6$ atoms. Since energy shift of quantum dots depend on their size, quantum dots made of the same substance emit light with different wavelengths depending on their size; thus, emission wavelengths can be easily adjusted by changing the size of quantum dots.

Since a quantum dot has an emission spectrum with a narrow peak, emission with high color purity can be obtained. In addition, a quantum dot is said to have a theoretical internal quantum efficiency of approximately 100%, which far exceeds that of a fluorescent organic compound, i.e., 25%, and is comparable to that of a phosphorescent organic compound. Therefore, a quantum dot can be used as a light-emitting material to obtain a light-emitting element having high emission efficiency. Furthermore, since a quantum dot which is an inorganic material has high inherent stability, a light-emitting element which is favorable also in terms of lifetime can be obtained.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is a means effective in obtaining blue light because the emission wavelength can be changed by changing the content ratio of elements.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased; thus, emission wavelengths of the quantum dots can be adjusted over a wavelength range of a spectrum of an ultraviolet region, a visible light region, and an infrared region by changing the size of quantum dots. The range of size (diameter) of quantum dots which is usually used is 0.5 nm to 20 nm, preferably 1 nm to 10 nm. The emission spectra are narrowed as the size distribution of the quantum dots gets smaller, and thus light can be obtained with high color purity. The shape of the quantum dots is not particularly limited and may be spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, to improve emission efficiency, concentration quenching of the light-emitting materials is suppressed by dispersing light-emitting materials in host materials. The host materials need to be materials having singlet excitation energy levels or triplet excitation energy levels higher than or equal to those of the light-emitting materials. In the case of using blue phosphorescent materials as light-emitting materials, it is particularly difficult to develop host materials which have triplet excitation energy levels higher than or equal to those of the blue phosphorescent materials and which are excellent in terms of a lifetime. Even when a light-emitting layer is composed of quantum dots and made without a host material, the quantum dots enable emission efficiency to be ensured; thus, a light-emitting element which is favorable in terms of a lifetime can be obtained. In the case where the light-emitting layer is composed of quantum dots, the quantum dots preferably have core-shell structures (including core-multi-shell structures).

In the case of using quantum dots as the light-emitting material in the light-emitting layer, the thickness of the light-emitting layer is set to 3 nm to 100 nm, preferably 10 nm to 100 nm, and the light-emitting layer is made to contain 1 volume % to 100 volume % of the quantum dots. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, blade coating method, a roll coating method, an ink-jet method, a printing method, a spray coating method, a curtain coating method, or a Langmuir-Blodgett method) may be employed. For a light-emitting layer containing a phosphorescent material, a vacuum evaporation method, as well as the wet process, can be suitably employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

«Pair of Electrodes»

The electrodes 101 and 102 function as an anode and a cathode of each light-emitting element. The electrodes 101 and 102 can be formed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor) are mixed. Alternatively, an inorganic carbon-based material such as graphene may be used. The resistivity of the material is preferably lower than or equal to $1\times10^5$ $\Omega\cdot$cm, further preferably lower than or equal to $1\times10^4$ $\Omega\cdot$cm.

Alternatively, the electrode 101 and/or the electrode 102 may be formed by stacking two or more of these materials.

In order to improve the light extraction efficiency, a material whose refractive index is higher than that of an electrode having a function of transmitting light may be formed in contact with the electrode. The material may be electrically conductive or non-conductive as long as it has a function of transmitting visible light. In addition to the oxide conductors described above, an oxide semiconductor and an organic substance are given as the examples of the material. Examples of the organic substance include the materials for the light-emitting layer, the hole-injection layer, the hole-transport layer, the electron-transport layer, and the electron-injection layer. Alternatively, an inorganic carbon-based material or a metal film thin enough to transmit light can be used. Further alternatively, stacked layers with a thickness of several nanometers to several tens of nanometers may be used.

In the case where the electrode 101 or the electrode 102 functions as the cathode, the electrode preferably contains a material having a low work function (lower than or equal to 3.8 eV). For example, it is possible to use an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, or the like.

When the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. In that case, the electrode 101 and the electrode 102 can have a function of adjusting the optical path length so that light of a desired wavelength emitted from each light-emitting layer resonates and is intensified, which is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

«Substrate»

A light-emitting element of one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

In this specification and the like, a light-emitting element can be formed using any of a variety of substrates, for example. The type of a substrate is not limited particularly. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper which includes a fibrous material, a base material film, and the like. As an example of a glass substrate, a barium borosilicate glass substrate, an alumino-borosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. For the above separation layer, a stack including inorganic films, which are a tungsten film and a silicon oxide film, or a structure in which a resin film of polyimide or the like is formed over a substrate can be used, for example.

In other words, after the light-emitting element is formed using a substrate, the light-emitting element may be transferred to another substrate. Example of the substrate to which the light-emitting element is transferred are, in addition to the above substrates, a cellophane substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), and the like), a leather substrate, a rubber substrate, and the like. When such a substrate is used, a light-emitting element with high durability, high heat resistance, reduced weight, or reduced thickness can be formed.

The light-emitting element 150 may be formed over an electrode electrically connected to a field-effect transistor (FET), for example, that is formed over any of the above-described substrates. Accordingly, an active matrix display device in which the FET controls the driving of the light-emitting element 150 can be manufactured.

The structure described above in this embodiment can be combined with any of the structures described in the other embodiments as appropriate.

Embodiment 4

Figure 2:
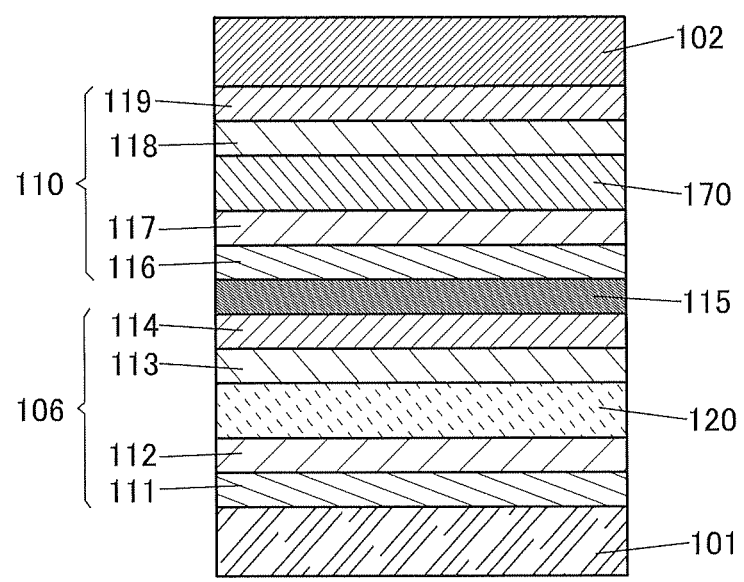
FIG. 2 is a schematic cross-sectional view illustrating a light-emitting element of one embodiment of the present invention.

In this embodiment, a light-emitting element having a structure different from that described in Embodiment 3 will be described below with reference to FIG. 2. In FIG. 2, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

<Structure Example 2 of Light-Emitting Element>

FIG. 2 is a schematic cross-sectional view of a light-emitting element 250.

The light-emitting element 250 illustrated in FIG. 2 includes a plurality of light-emitting units (a light-emitting unit 106 and a light-emitting unit 110) between a pair of electrodes (the electrode 101 and the electrode 102). One of the light-emitting units preferably has the same structure as the EL layer 100 illustrated in FIG. 1A. That is, it is preferable that the light-emitting element 150 illustrated in FIG. 1A include one light-emitting unit while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 2, the light-emitting unit 106 and the light-emitting unit 110 are stacked, and a charge-generation layer 115 is provided between the light-emitting unit 106 and the light-emitting unit 110. Note that the light-emitting unit 106 and the light-emitting unit 110 may have the same structure or different structures. For example, it is preferable that a structure similar to that of the EL layer 100 be used in the light-emitting unit 110.

The light-emitting element 250 includes the light-emitting layer 120 and a light-emitting layer 170. The light-emitting unit 106 includes the hole-injection layer 111, the hole-transport layer 112, the electron-transport layer 113, and the electron-injection layer 114 in addition to the light-emitting layer 170. The light-emitting unit 110 includes a hole-injection layer 116, a hole-transport layer 117, an electron-transport layer 118, and an electron-injection layer 119 in addition to the light-emitting layer 120.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 3 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1 \times 10^{-6}$ cm$^2$/Vs or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer is not necessarily included in the light-emitting unit. Alternatively, when a surface of the light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 110 is configured so that electrons are injected into one of the light-emitting units and holes are injected into the other light-emitting unit when a voltage is applied between the electrode 101 and the electrode 102. For example, in FIG. 3A, the charge-generation layer 115 injects electrons into the light-emitting unit 106 and holes into the light-emitting unit 110 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even when having lower conductivity than the pair of electrodes (the electrodes 101 and 102).

The charge-generation layer 115 formed by using any of the above materials can suppress an increase in driving voltage caused by the stack of the light-emitting layers.

Although FIG. 2 illustrates the light-emitting element including the two light-emitting units, the light-emitting element can include three or more light-emitting units stacked. With a plurality of light-emitting units between a pair of electrodes, which are partitioned by the charge-generation layer as in the light-emitting element 250, it is possible to provide a light-emitting element which can emit high-luminance light with the current density kept low, has a long lifetime, and consumes low power.

Note that in each of the above-described structures, the emission colors of the guest materials used in the light-emitting unit 106 and the light-emitting unit 110 may be the same or different. In the case where guest materials emitting light of the same color are used for the light-emitting unit 106 and the light-emitting unit 110, the light-emitting element 250 can exhibit high emission luminance at a small current value, which is preferable. In the case where guest materials emitting light of different colors are used for the light-emitting unit 106 and the light-emitting unit 110, the light-emitting element 250 can exhibit multi-color light emission, which is preferable. In that case, when a plurality of light-emitting materials with different emission wavelengths are used in one or both of the light-emitting layers 120 and 170, lights with different emission peaks synthesize light emission from the light-emitting element 250. That is, the emission spectrum of the light-emitting element 250 has at least two local maximum values.

The above structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

In the case of a light-emitting element in which three or more light-emitting units are stacked, colors of light emitted from guest materials in the light-emitting units may be the same or different from each other. In the case where the light-emitting element includes a plurality of light-emitting units emitting light of the same color, these light-emitting units can exhibit light of the color with higher emission luminance with a smaller current value as compared with light of the other colors. Such a structure can be suitably used to adjust light emission colors. In particular, the structure is suitably used in the case where guest materials which emit light of different colors with different emission efficiencies are used. For example, when the light-emitting element has a three-layer structure of light-emitting units, the light-emitting units are two light-emitting units including a fluorescent material and emitting light of the same color and one light-emitting unit including a phosphorescent material and emitting light of a color different from the color of the fluorescent material, in which case the intensity of fluorescence and phosphorescence can be adjusted. Thus, the intensity of light emission of colors can be adjusted by changing the number of light-emitting units.

When the light-emitting element includes two fluorescence-emitting units and one phosphorescence-emitting unit, it is preferable that the two fluorescence-emitting units include a blue fluorescent material and the one phosphorescence-emitting unit include a yellow phosphorescent material; that the two fluorescence-emitting units include a blue fluorescent material and the one phosphorescence-emitting unit include a red phosphorescent material and a green phosphorescent material; or that the two fluorescence-emitting units include a blue fluorescent material and the one phosphorescence-emitting unit include a red phosphorescent material, a yellow phosphorescent material, and a green phosphorescent material, in which case white light emission can be obtained efficiently.

At least one of the light-emitting layers 120 and 170 may be divided into layers and each of the divided layers may contain a different light-emitting material. That is, at least one of the light-emitting layers 120 and 170 may consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. A light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

In addition, the light-emitting layer of the light-emitting unit 110 preferably contains a phosphorescent compound. When the structure with the organic compound of one embodiment of the present invention is used for at least one of the plurality of units, a light-emitting element with high heat resistance and high emission efficiency can be provided. Note that this embodiment can be combined with any of the other embodiments as appropriate.

Embodiment 5

FIG. 3A is a top view of the light-emitting device and FIG. 3B is a cross-sectional view taken along the lines A-B and C-D in FIG. 3A. The light-emitting device includes a driver circuit portion (source side driver circuit) 601, a pixel portion 602, and a driver circuit portion (gate side driver circuit) 603, which control light emission of a light-emitting element and are illustrated with dotted lines. Moreover, a reference numeral 604 denotes a sealing substrate, a reference numeral 625 denotes a desiccant, and a reference numeral 605 denotes a sealant. A portion surrounded by the sealant 605 is a space 607.

Note that a lead wiring 608 is a wiring for transmitting signals to be input to the source side driver circuit 601 and the gate side driver circuit 603 and for receiving a video signal, a clock signal, a start signal, a reset signal, and the like from a flexible printed circuit (FPC) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure of the light-emitting device is described with reference to FIG. 3B. The driver circuit portion and the pixel portion are formed over an element substrate 610. Here, the source side driver circuit 601, which is the driver circuit portion, and one pixel of the pixel portion 602 are illustrated.

In the source side driver circuit 601, a CMOS circuit is formed in which an n-channel TFT 623 and a p-channel TFT 624 are combined. The driver circuit may be formed using various circuits such as a CMOS circuit, a PMOS circuit, or an NMOS circuit. Although a driver-integrated type in which the driver circuit is formed over the substrate is described in this embodiment, the driver circuit is not necessarily formed over the substrate, and may be formed outside the substrate.

The pixel portion 602 includes a plurality of pixels including a switching TFT 611, a current controlling TFT 612, and a first electrode 613 electrically connected to a drain of the current controlling TFT 612. Note that an insulator 614 is formed to cover an end portion of the first electrode 613. The insulator 614 can be formed using a positive photosensitive resin film.

In order to improve coverage with a film that is formed over the insulator 614, the insulator 614 is formed to have a curved surface with curvature at its upper or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 µm and less than or equal to 0.3 μm. As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 preferably has the structure described in Embodiment 3 and Embodiment 4. In the light-emitting device of this embodiment, the pixel portion, which includes a plurality of light-emitting elements, may include both the light-emitting element with the structure described in Embodiment 1 and Embodiment 2 and a light-emitting element with a different structure.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with a filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), polyvinyl fluoride (PVF), polyester, acrylic, or the like can be used.

As described above, the light-emitting device including the light-emitting element described in Embodiment 3 and Embodiment 4 can be obtained.

<Structure Example 1 of Light-Emitting Device>

As an example of a light-emitting device, FIGS. 4A and 4B each illustrate a light-emitting device including a light-emitting element exhibiting white light emission and a coloring layer (a color filter).

FIG. 4A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1026, an EL layer 1028, a second electrode 1029 of the light-emitting elements, a sealing substrate 1031, a sealant 1032, and the like.

In FIGS. 4A and 4B, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 4A, light emitted from some of the light-emitting layers does not pass through the coloring layers, while light emitted from the others of the light-emitting layers passes through the coloring layers. Since light that does not pass through the coloring layers is white and light that passes through any one of the coloring layers is red, blue, or green, an image can be displayed using pixels of the four colors.

FIG. 4B illustrates an example in which the red coloring layer 1034R, the green coloring layer 1034G, and the blue coloring layer 1034B are formed between the gate insulating film 1003 and the first interlayer insulating film 1020. As illustrated in FIG. 4B, the coloring layers may be provided between the substrate 1001 and the sealing substrate 1031.

The above-described light-emitting device has a structure in which light is extracted from the substrate 1001 side where the TFTs are formed (a bottom emission structure), but may have a structure in which light is extracted from the sealing substrate 1031 side (a top emission structure).

<Structure Example 2 of Light-Emitting Device>

Figure 5:
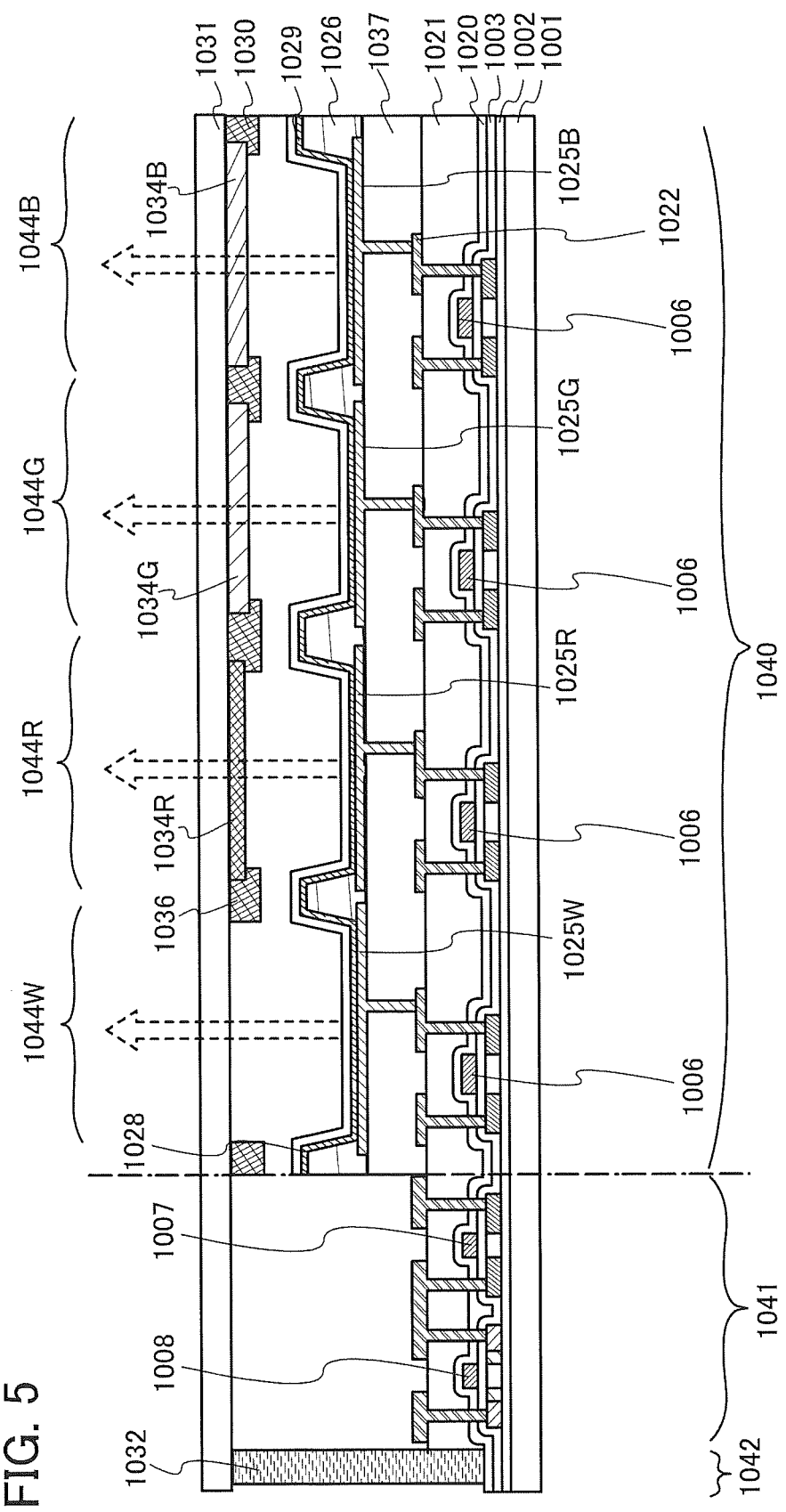
FIG. 5 is a conceptual diagram illustrating an active matrix light-emitting device of one embodiment of the present invention.

FIG. 5 is a cross-sectional view of a light-emitting device having a top emission structure. In this case, a substrate that does not transmit light can be used as the substrate 1001. The process up to the step of forming of a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, or can be formed using any other various materials.

Lower electrodes 1025W, 1025R, 1025G, and 1025B of the light-emitting elements each function as an anode here, but may function as a cathode. Furthermore, in the case of the light-emitting device having a top emission structure as illustrated in FIG. 5, the lower electrodes 1025W, 1025R, 1025G, and 1025B are preferably reflective electrodes. Note that the second electrode 1029 preferably has a function of reflecting light and a function of transmitting light. It is preferable that a microcavity structure be used between the second electrode 1029 and the lower electrodes 1025W, 1025R, 1025G, and 1025B, in which case light having a specific wavelength is amplified. The EL layer 1028 is formed to have a structure similar to the structure described in Embodiment 2, with which white light emission can be obtained.

In FIGS. 4A and 4B and FIG. 5, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 5, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

As described above, the light-emitting device including the light-emitting element described in Embodiment 3 and Embodiment 4 can be obtained.

Note that this embodiment can be combined with any of the other embodiments as appropriate.

Embodiment 6

In this embodiment, electronic devices of one embodiment of the present invention will be described.

According to one embodiment of the present invention, highly reliable electronic devices having flat surfaces can be manufactured. According to one embodiment of the present invention, highly reliable electronic devices with curved surfaces can be manufactured. According to one embodiment of the present invention, flexible and highly reliable electronic devices can be manufactured.

Examples of the electronic devices include a television set, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

The light-emitting device of one embodiment of the present invention can achieve high visibility regardless of the intensity of external light. Thus, the light-emitting device of one embodiment of the present invention can be suitably used for a portable electronic device, a wearable electronic device (wearable device), an e-book reader, or the like.

Figure 6A:
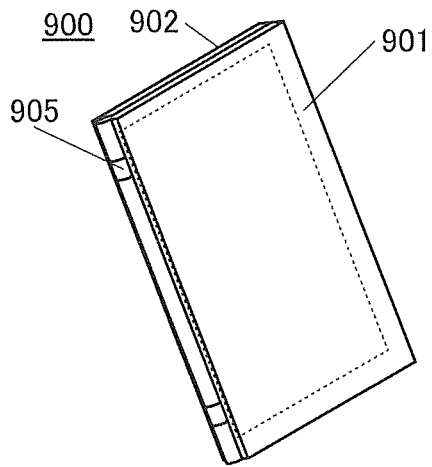
FIGS. 6A to 6D are schematic views illustrating electronic devices of embodiments of the present invention.
Figure 6B:
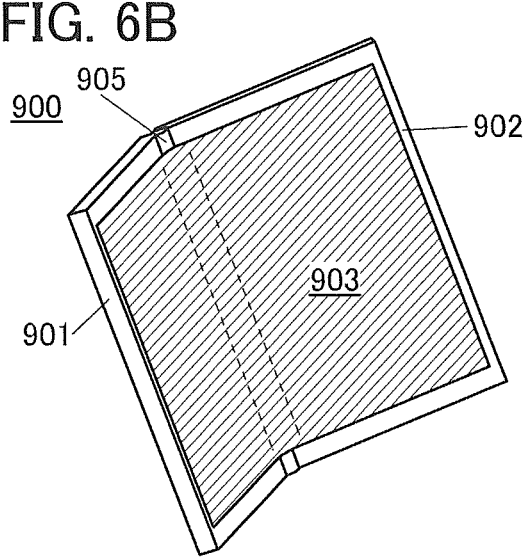

A portable information terminal 900 illustrated in FIGS. 6A and 6B includes a housing 901, a housing 902, a display portion 903, a hinge portion 905, and the like.

The housing 901 and the housing 902 are joined together with the hinge portion 905. The portable information terminal 900 can be opened as illustrated in FIG. 6B from a closed state (FIG. 6A). Thus, the portable information terminal 900 has high portability when carried and excellent visibility when used because of its large display region.

In the portable information terminal 900, the flexible display portion 903 is provided across the housing 901 and the housing 902 which are joined to each other by the hinge portion 905.

The light-emitting device manufactured using one embodiment of the present invention can be used for the display portion 903. Thus, the portable information terminal can be manufactured with high yield.

The display portion 903 can display at least one of a text, a still image, a moving image, and the like. When a text is displayed on the display portion, the portable information terminal 900 can be used as an e-book reader.

When the portable information terminal 900 is opened, the display portion 903 is significantly curved. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being bent since pixels are continuously arranged from the housing 901 to the housing 902.

The display portion 903 functions as a touch panel and can be controlled with a finger, a stylus, or the like.

The display portion 903 is preferably formed using one flexible display. Thus, a continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which the housing 901 and the housing 902 become locked (they are not opened any further) is preferably greater than or equal to 90° and less than 180° and can be typically 90°, 120°, 135°, 150°, 175°, or the like. In that case, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be provided.

A power button, an operation button, an external connection port, a speaker, a microphone, or the like may be provided for the housing 901 and the housing 902.

Either of the housing 901 and the housing 902 is provided with a wireless communication module, and data can be transmitted and received through a computer network such as the Internet, a local area network (LAN), or Wi-Fi (registered trademark).

Figure 6C:
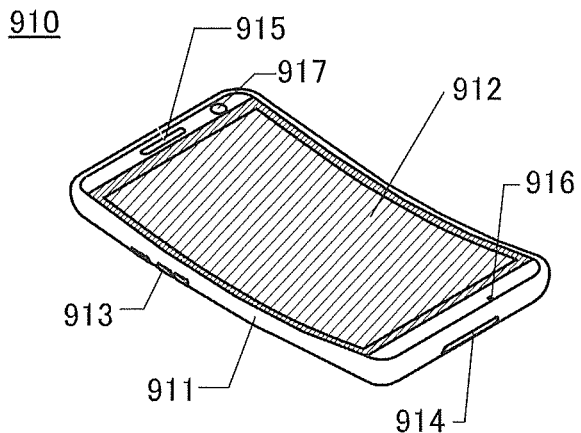

A portable information terminal 910 illustrated in FIG. 6C includes a housing 911, a display portion 912, an operation button 913, an external connection port 914, a speaker 915, a microphone 916, a camera 917, and the like.

The light-emitting device manufactured using one embodiment of the present invention can be used for the display portion 912. Thus, the portable information terminal can be manufactured with high yield.

The portable information terminal 910 includes a touch sensor in the display portion 912. Operations such as making a call and inputting a character can be performed by touch on the display portion 912 with a finger, a stylus, or the like.

With the operation button 913, the power can be turned on or off. In addition, types of images displayed on the display portion 912 can be switched; for example, switching an image from a mail creation screen to a main menu screen is performed with the operation button 913.

When a detection device such as a gyroscope sensor or an acceleration sensor is provided inside the portable information terminal 910, the direction of display on the screen of the display portion 912 can be automatically changed by determining the orientation of the portable information terminal 910 (whether the portable information terminal 910 is placed horizontally or vertically). Furthermore, the direction of display on the screen can be changed by touch on the display portion 912, operation with the operation button 913, sound input using the microphone 916, or the like.

The portable information terminal 910 functions as, for example, one or more of a telephone set, a notebook, and an information browsing system. Specifically, the portable information terminal 910 can be used as a smartphone. The portable information terminal 910 is capable of executing a variety of applications such as mobile phone calls, e-mailing, viewing and editing texts, music reproduction, reproducing a moving image, Internet communication, and computer games, for example.

Figure 6D:
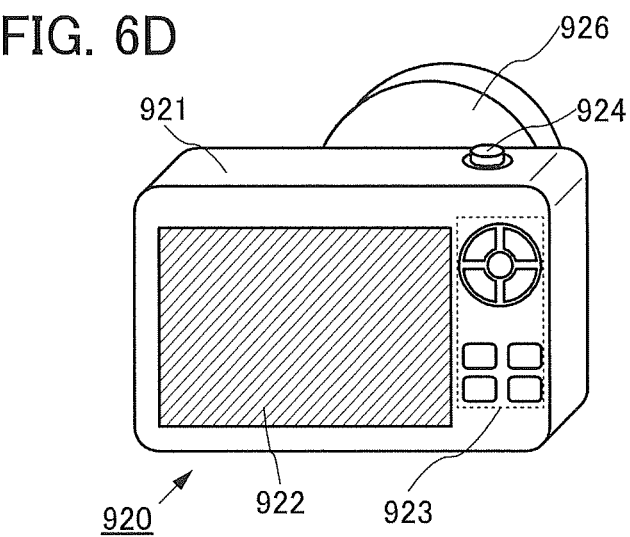

A camera 920 illustrated in FIG. 6D includes a housing 921, a display portion 922, operation buttons 923, a shutter button 924, and the like. Furthermore, an attachable lens 926 is attached to the camera 920.

The light-emitting device manufactured using one embodiment of the present invention can be used for the display portion 922. Thus, the camera can be manufactured with high yield.

Although the lens 926 of the camera 920 here is detachable from the housing 921 for replacement, the lens 926 may be incorporated into the housing 921.

A still image or a moving image can be taken with the camera 920 at the press of the shutter button 924. In addition, images can also be taken by the touch of the display portion 922 which has a function of a touch panel.

Note that a stroboscope, a viewfinder, or the like can be additionally attached to the camera 920. Alternatively, these may be incorporated into the housing 921.

FIGS. 7A to 7E illustrate electronic devices. These electronic devices each include a housing 9000, a display portion 9001, a speaker 9003, an operation key 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone 9008, and the like.

The light-emitting device manufactured using one embodiment of the present invention can be favorably used for the display portion 9001. Thus, the electronic devices can be manufactured with high yield.

The electronic devices illustrated in FIGS. 7A to 7E can have a variety of functions, for example, a function of displaying a variety of information (a still image, a moving image, a text image, and the like) on the display portion, a touch panel function, a function of displaying a calendar, the date, the time, and the like, a function of controlling processing with a variety of software (programs), a wireless communication function, a function of being connected to a variety of computer networks with a wireless communication function, a function of transmitting and receiving a variety of data with a wireless communication function, a function of reading a program or data stored in a storage medium and displaying the program or data on the display portion, and the like. Note that the functions of the electronic devices illustrated in FIGS. 7A to 7E are not limited to the above, and the electronic devices may have other functions.

Figure 7A:
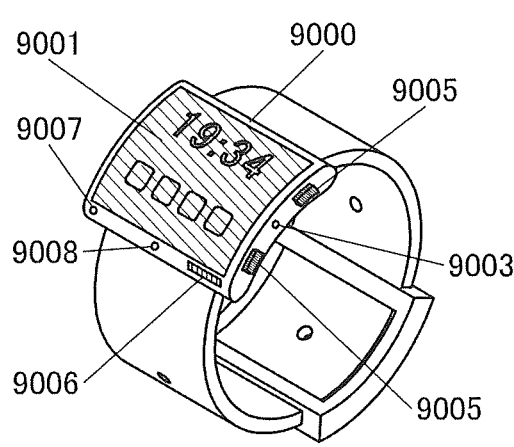
FIGS. 7A to 7E are schematic views illustrating electronic devices of embodiments of the present invention.
Figure 7B:
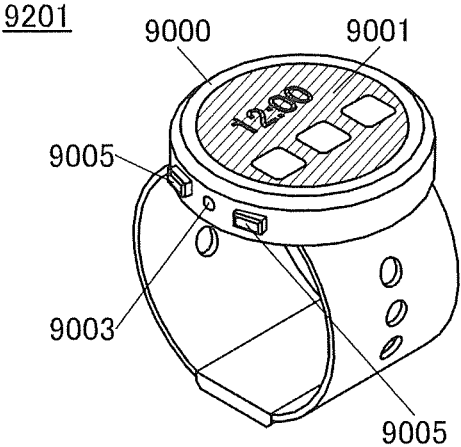

FIG. 7A is a perspective view of a watch-type portable information terminal 9200. FIG. 7B is a perspective view of a watch-type portable information terminal 9201.

The portable information terminal 9200 illustrated in FIG. 7A is capable of executing a variety of applications such as mobile phone calls, e-mailing, viewing and editing texts, music reproduction, Internet communication, and computer games. The display surface of the display portion 9001 is bent, and an image can be displayed on the bent display surface. The portable information terminal 9200 can employ near field communication conformable to a communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is also possible. Note that the charging operation may be performed by wireless power feeding without using the connection terminal 9006.

Unlike in the portable information terminal illustrated in FIG. 7A, the display surface of the display portion 9001 is not curved in the portable information terminal 9201 illustrated in FIG. 7B. Furthermore, the external state of the display portion of the portable information terminal 9201 is a non-rectangular shape (a circular shape in FIG. 7B).

Figure 7C:
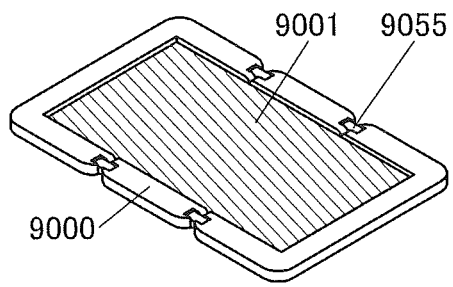
Figure 7D:
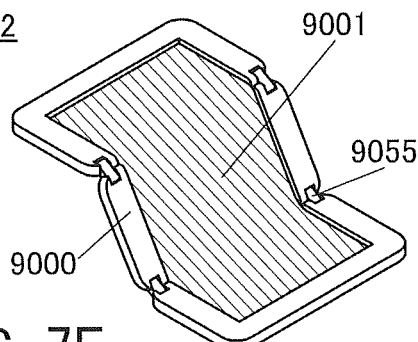
Figure 7E:
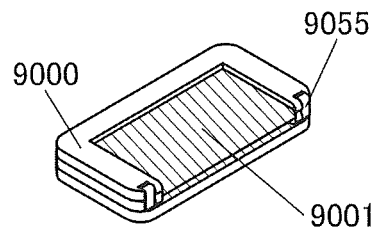

FIGS. 7C to 7E are perspective views of a foldable portable information terminal 9202. FIG. 7C is a perspective view illustrating the portable information terminal 9202 that is opened. FIG. 7D is a perspective view illustrating the portable information terminal 9202 that is being opened or being folded. FIG. 7E is a perspective view illustrating the portable information terminal 9202 that is folded.

The folded portable information terminal 9202 is highly portable, and the opened portable information terminal 9202 is highly browsable due to a seamless large display region. The display portion 9001 of the portable information terminal 9202 is supported by three housings 9000 joined together by hinges 9055. By folding the portable information terminal 9202 at a connection portion between two housings 9000 with the hinges 9055, the portable information terminal 9202 can be reversibly changed in shape from opened to folded. For example, the portable information terminal 9202 can be bent with a radius of curvature of greater than or equal to 1 mm and less than or equal to 150 mm.

Note that this embodiment can be combined with any of the other embodiments as appropriate.

Embodiment 7

In this embodiment, examples in which the light-emitting element of one embodiment of the present invention is used for various electronic devices and lighting devices will be described with reference to FIGS. 8A to 8C and FIG. 9.

An electronic device or a lighting device that has a light-emitting region with a curved surface can be obtained with use of the light-emitting element of one embodiment of the present invention which is fabricated over a substrate having flexibility.

Furthermore, a light-emitting device in which the light-emitting element of one embodiment of the present invention is used can also be used for lighting for motor vehicles, examples of which are lighting for a windshield, a ceiling, and the like.

Figure 8A:
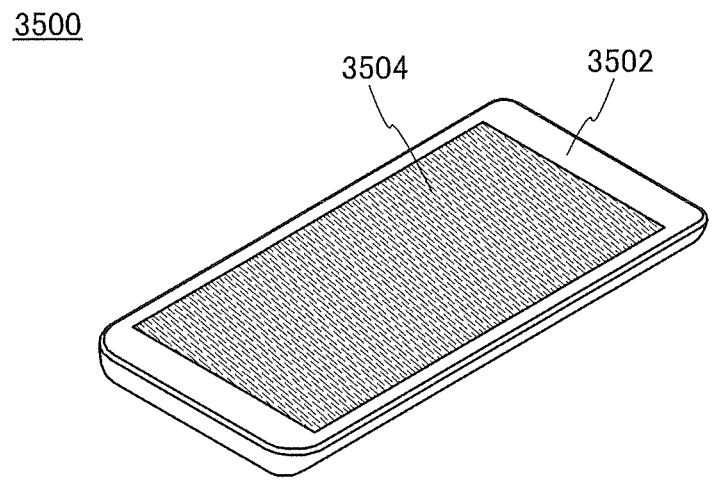
FIGS. 8A to 8C illustrate an electronic device and a lighting device of embodiments of the present invention.
Figure 8B:
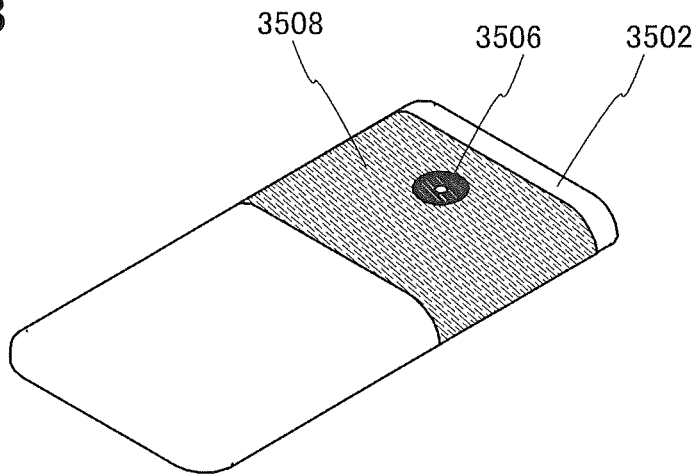

FIG. 8A is a perspective view illustrating one surface of a multifunction terminal 3500, and FIG. 8B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 8A and 8B can have a variety of functions as in the electronic devices illustrated in FIGS. 7A to 7C.

The housing 3502 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 8C:
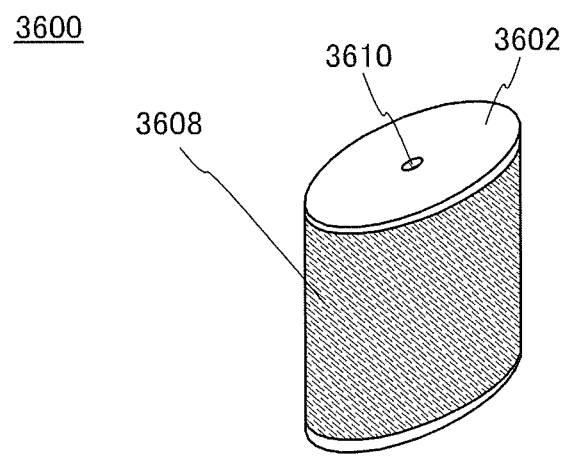

FIG. 8C is a perspective view of a security light 3600. The light 3600 includes lighting 3608 on the outside of the housing 3602, and a speaker 3610 and the like are incorporated in the housing 3602. The light-emitting element of one embodiment of the present invention can be used for the lighting 3608.

The light 3600 emits light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The light 3600 can emit light in various directions; therefore, it is possible to intimidate a thug or the like with light, or light and sound. Moreover, the light 3600 may include a camera such as a digital still camera to have a photography function.

Figure 9:
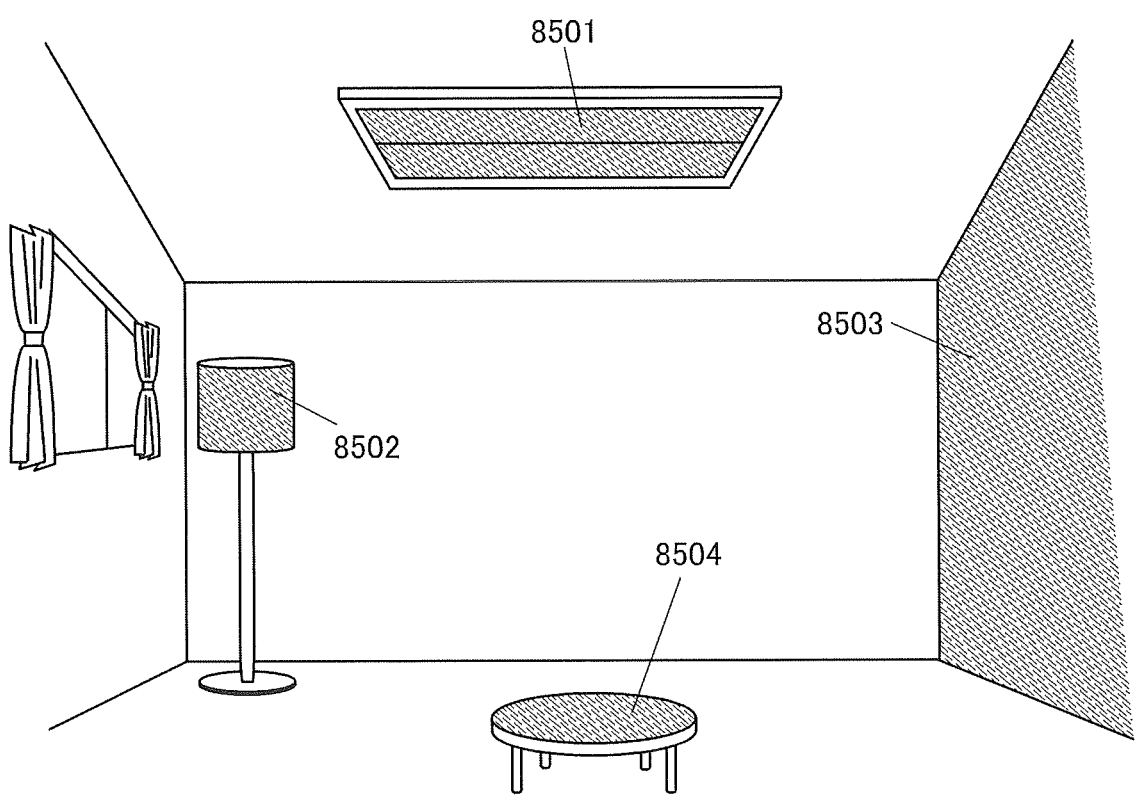
FIG. 9 illustrates lighting devices of embodiments of the present invention.

FIG. 9 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting element of one embodiment of the present invention. Note that the light-emitting device can be used for lighting devices and electronic devices in a variety of fields without being limited to the lighting devices and the electronic devices described in this embodiment.

The structure described above in this embodiment can be combined with any of the structures described in the other embodiments as appropriate.

Example 1

In this example, a method for synthesizing 3,8-bis[3-(dibenzothiophen-4-yl)phenyl]benzofuro[2,3-b]pyrazine (abbreviation: 3,8mDBtP2Bfpr) (Structural Formula (100)), which is one of compounds represented by General Formula (G0) of one embodiment of the present invention, and the characteristics of this compound are described.

Synthesis Example 1

Step 1: Synthesis of 6-chloro-3-(5-chloro-2-methoxyphenyl)pyrazin-2-amine

Into a three-neck flask equipped with a reflux pipe were put 1.00 g of 3-bromo-6-chloropyrazin-2-amine, 0.90 g of 5-chloro-2-methoxyphenylboronic acid, 0.93 g of potassium fluoride, and 17 mL of tetrahydrofuran, and the air in the flask was replaced with nitrogen. The mixture in the flask was degassed by being stirred under reduced pressure, and then 0.088 g of tris(dibenzylideneacetone)dipalladium(0) and 0.8 mL of tri-t-butyl phosphine were added thereto. The mixture was reacted by being stirred at 80° C. for 40 hours. After a predetermined time elapsed, the obtained mixture was suction-filtered and the filtrate was concentrated. The obtained residue was purified by silica gel column chromatography using dichloromethane as a developing solvent, and the obtained filtrate was concentrated, whereby 0.92 g of 6-chloro-3-(5-chloro-2-methoxyphenyl)pyrazin-2-amine, which was a target yellowish white powder, was obtained in a yield of 71%. A synthesis scheme of Step 1 is shown in (a-1).

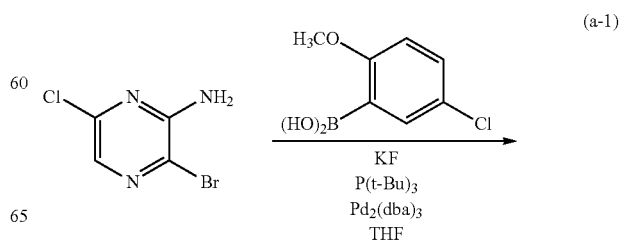

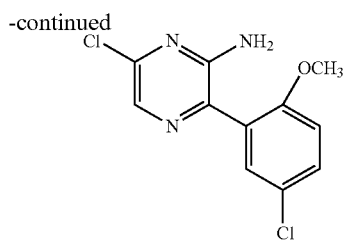

Step 2: Synthesis of 3,8-dichlorobenzofuro[2,3-b]pyrazine

Into a three-neck flask were put 1.37 g of 6-chloro-3-(5-chloro-2-methoxyphenyl)pyrazin-2-amine obtained through Step 1, 16 mL of dehydrated tetrahydrofuran, and 32 mL of a glacial acetic acid, and the air in the flask was replaced with nitrogen. After the flask was cooled down to −10° C., 1.9 mL of tert-butyl nitrite was dripped, and the mixture was stirred at −10° C. for 1 hour and at 0° C. for 20 hours. After a predetermined time elapsed, 100 mL of water was added to the obtained suspension and then suction filtration was performed. The obtained solid was dissolved in dichloromethane, filtration was performed through a filter aid in which Celite, alumina, and Celite were stacked in this order, and the filtrate was concentrated, whereby 0.87 g of 3,8-dichlorobenzofuro[2,3-b]pyrazine, which was a target white solid, was obtained in a yield of 70%. A synthesis scheme of Step 2 is shown in (a-2).

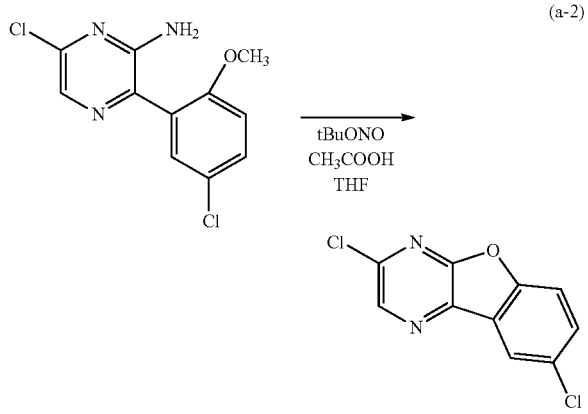

(a-2)

Step 3: Synthesis of 3,8-bis[3-(dibenzothiophen-4-yl)phenyl]benzofuro[2,3-b]pyrazine (Abbreviation: 3,8mDBtP2Bfpr)

Then, into a three-neck flask were put 0.87 g of 3,8-dichlorobenzofuro[2,3-b]pyrazine obtained through Step 2, 2.41 g of a 3-(4-dibenzothiophene)phenylboronic acid, 4.57 g of tripotassium phosphate, 29 mL of diglyme, and 2.0 mL of tert-butanol, and the air in the flask was replaced with nitrogen. The mixture in the flask was degassed by being stirred under reduced pressure, 0.016 g of palladium(II) acetate and 0.054 g of di(1-adamantyl)-n-butylphosphine (abbreviation: CataCXiumA) were added thereto, and the resulting mixture was stirred at 140° C. for 8 hours to be reacted. After a predetermined time elapsed, the obtained suspension was subjected to suction filtration and was washed with water and ethanol. The obtained solid was purified by silica gel column chromatography using toluene as a developing solvent, and then recrystallization from a mixed solvent of toluene and hexane was performed, whereby 1.25 g of 3,8mDBtP2Bfpr, which was a target yellowish white solid, was obtained in a yield of 52%. A synthesis scheme of Step 3 is shown in (a-3).

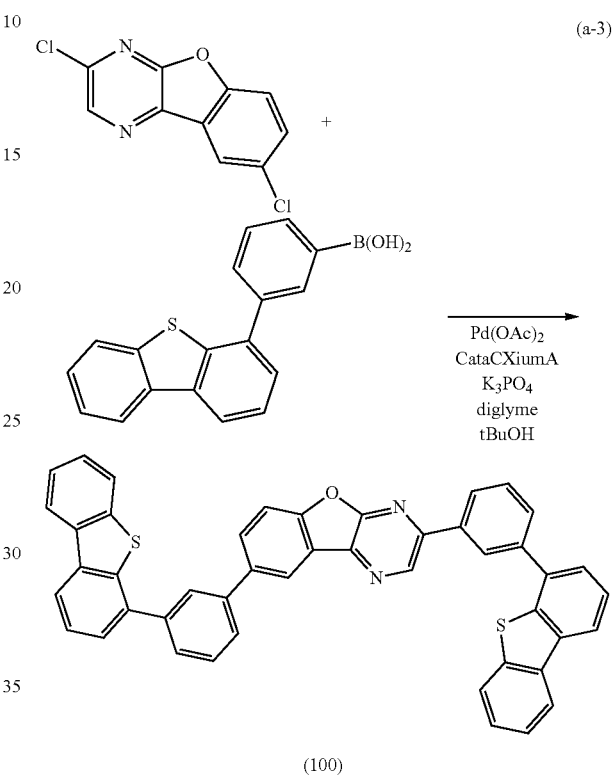

(a-3)

(100)

Then, 1.14 g of this yellowish white solid was purified by a train sublimation method. In the purification by sublimation, the yellowish white solid was heated at 350° C. under a pressure of 2.6 Pa with an argon gas at a flow rate of 5 mL/min. After the purification by sublimation, 0.99 g of a target yellowish white solid was obtained at a collection rate of 87%.

The obtained solid was subjected to nuclear magnetic resonance spectrometry ($^1$H NMR), and the results are shown below.

$^1$H-NMR. δ (CD$_2$Cl$_2$): 7.49-7.54 (m, 4H), 7.62-7.65 (m, 41H), 7.69 (t, 1H), 7.74 (t, 1H), 7.80-7.84 (m, 3H), 7.89-7.91 (m, 3H), 8.03 (dd, 1H), 8.14 (s, 1H), 8.23-8.28 (m, 5H), 8.56 (d, 1H), 8.59 (s, 1H), 9.26 (s, 1H).

Figure 10A:
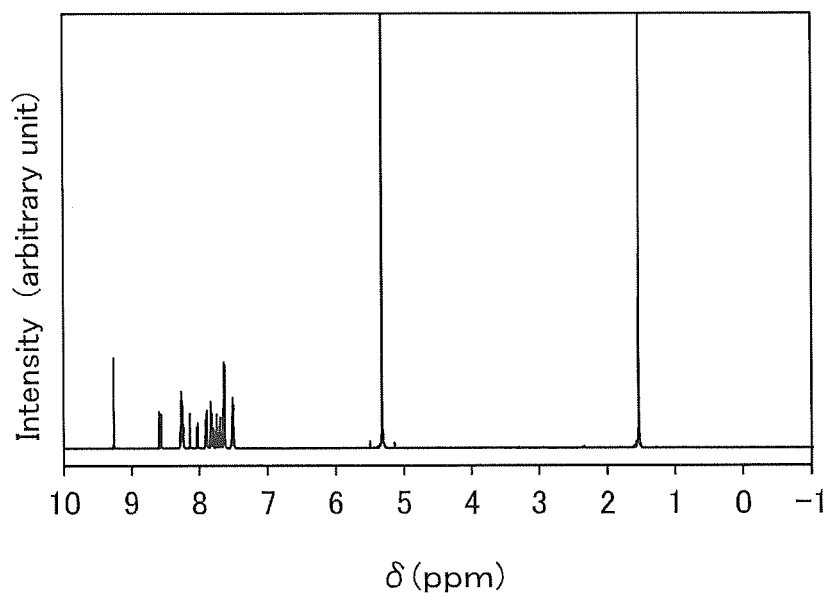
FIGS. 10A and 10B are NMR charts of a compound in Example.
Figure 10B:
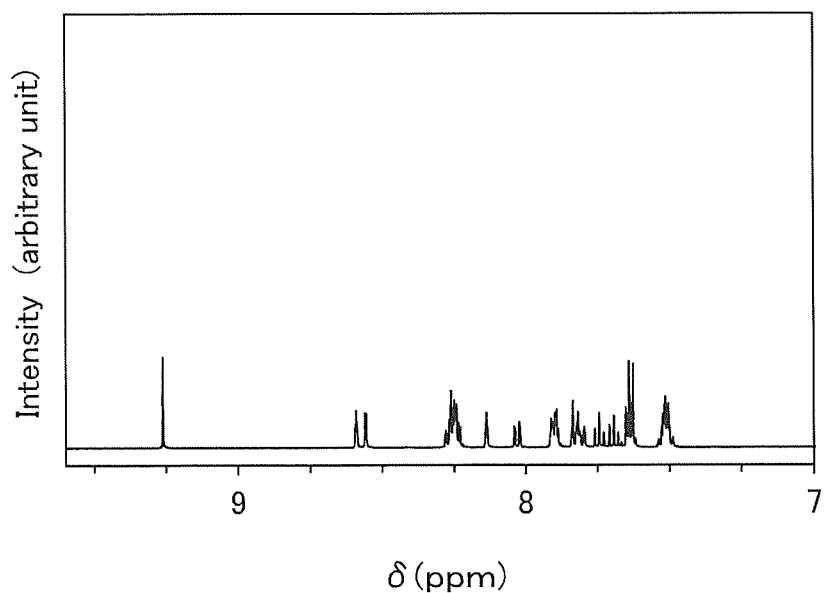

FIGS. 10A and 10B are $^1$H NMR charts of the obtained solid. Note that FIG. 10B is a chart showing an enlarged part in the range of 7.0 ppm to 9.6 ppm of FIG. 10A. The measurement results indicate that the target substance, 3,8mDBtP2Bfpr was obtained.

<Characteristics of 3,8mDBtP2Bfpr>

Figure 11:
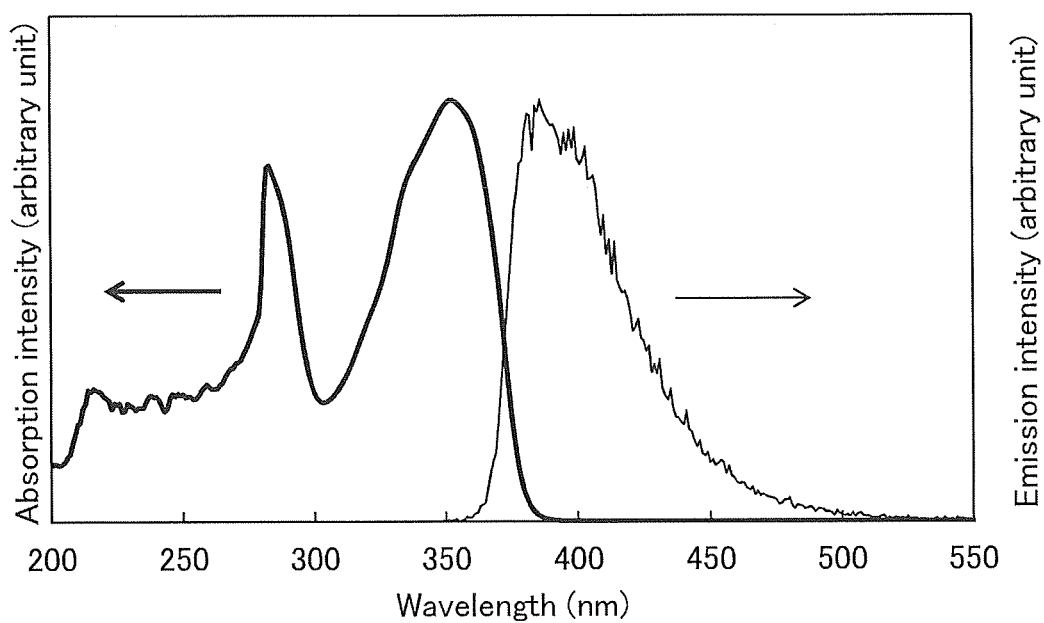
FIG. 11 shows absorption and emission spectra of a compound in Example.

Next, FIG. 11 shows an absorption spectrum and an emission spectrum of 3,8mDBtP2Bfpr in a toluene solution.

The absorption spectrum was measured with an ultraviolet-visible spectrophotometer (V-550, produced by JASCO Corporation). The absorption spectrum of 3,8mDBtP2Bfpr in the toluene solution was measured with a toluene solution of 3,8mDBtP2Bfpr put in a quartz cell. From this absorption spectrum, absorption spectra of the toluene solution, which was a solvent, and the quartz cell were subtracted, and the obtained absorption spectrum is shown in the graph. The emission spectrum was measured with a PL-EL measurement apparatus (produced by Hamamatsu Photonics K.K.). The emission spectrum of 3,8mDBtP2Bfpr in the toluene solution was measured with the toluene solution of 3,8mDBtP2Bfpr put in a quartz cell.

FIG. 11 shows that 3,8mDBtP2Bfpr in the toluene solution has absorption spectrum peaks around 283 nm and 352 nm, and an emission spectrum peak around 386 nm (excitation wavelength: 333 nm).

Figure 12:
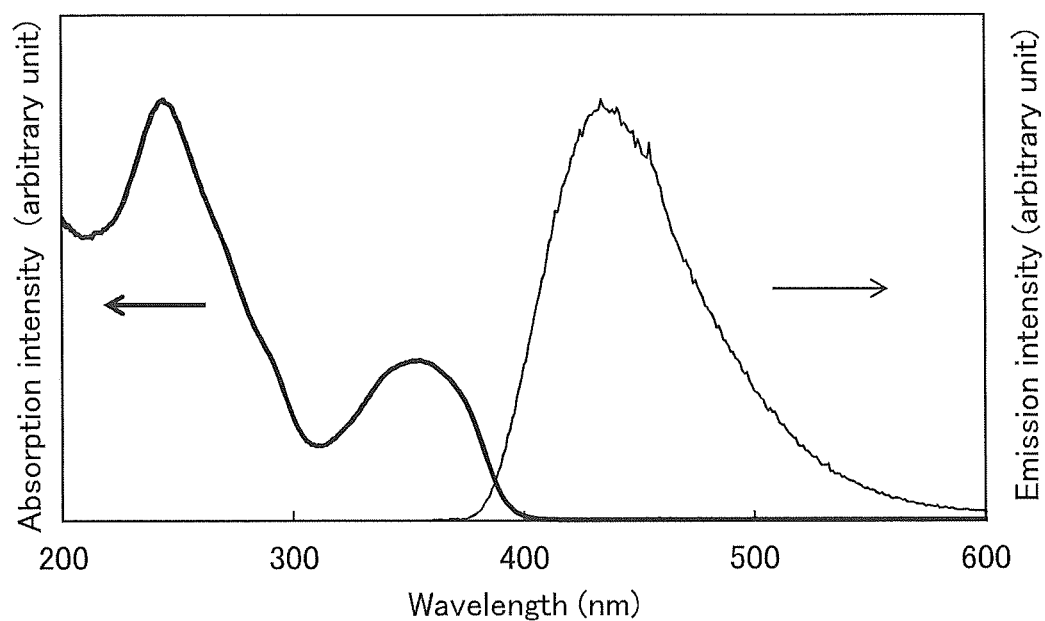
FIG. 12 shows absorption and emission spectra of a compound in Example.

Next, an absorption spectrum and an emission spectrum of a solid thin film of 3,8mDBtP2Bfpr were measured. The solid thin film was formed over a quartz substrate by a vacuum evaporation method. The absorption spectrum was measured with an ultraviolet-visible light spectrophotometer (U4100, produced by MABUCHI S&T INC.). The emission spectrum was measured with a fluorescence spectrophotometer (FS920 produced by Hamamatsu Photonics K.K.). FIG. 12 shows the measurement results of the absorption and emission spectra of the obtained solid thin film. In FIG. 12, the horizontal axis represents wavelength and the vertical axes represent absorption intensity and emission intensity.

FIG. 12 shows that the solid thin film of 3,8mDBtP2Bfpr has absorption spectrum peaks around 247 nm and 354 nm, and an emission spectrum peak around 437 nm (excitation wavelength: 355 nm).

Example 2

In this example, a method for synthesizing 2,8-bis[3-(dibenzothiophen-4-yl)phenyl]benzofuro[2,3-b]pyrazine (abbreviation: 2,8mDBtP2Bfpr) (Structural Formula (101)), which is one of compounds represented by General Formula (G0) of one embodiment of the present invention, and the characteristics of this compound are described.

Synthesis Example 2

Step 1: Synthesis of 5-chloro-3-(5-chloro-2-methoxyphenyl)pyrazin-2-amine

Into a three-neck flask equipped with a reflux pipe were put 2.48 g of 3-bromo-5-chloropyrazin-2-amine, 2.19 g of 5-chloro-2-methoxyphenylboronic acid, 2.26 g of potassium fluoride, and 43 mL of tetrahydrofuran, and the air in the flask was replaced with nitrogen. The mixture in the flask was degassed by being stirred under reduced pressure, and then 0.44 g of tris(dibenzylideneacetone)dipalladium(0) and 4.0 mL of tri-t-butyl phosphine were added thereto. The mixture was reacted by being stirred at 80° C. for 42 hours. After a predetermined time elapsed, the obtained mixture was suction-filtered and the filtrate was concentrated. The obtained residue was purified by silica gel column chromatography using a developing solvent (toluene:ethyl acetate=10:1), whereby 1.00 g of 2,8-bis[3-(dibenzothiophen-4-yl)phenyl]benzofuro[2,3-b]pyrazine, which was a target substance, was obtained in a yield of 31%. A synthesis scheme of Step 1 is shown in (b-1).

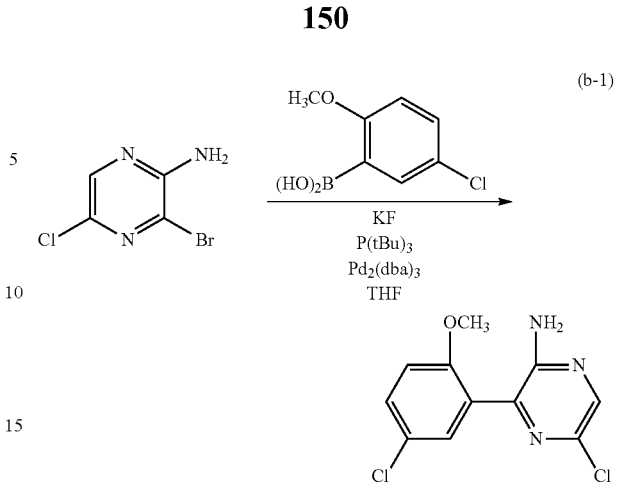

Step 2: Synthesis of 2,8-dichlorobenzofuro[2,3-b]pyrazine

Next, into a three-neck flask were put 1.00 g of 5-chloro-3-(5-chloro-2-methoxyphenyl)pyrazin-2-amine obtained through Step 1, 12 mL of dehydrated tetrahydrofuran, and 24 mL of a glacial acetic acid, and the air in the flask was replaced with nitrogen. After the flask was cooled down to −10° C., 1.3 mL of tert-butyl nitrite was dripped, and the mixture was stirred at −10° C. for 1 hour and at 0° C. for 20 hours. After a predetermined time elapsed, 100 mL of water was added to the obtained suspension and then suction filtration was performed. The obtained solid was purified by silica gel column chromatography using dichloromethane as a developing solvent, whereby 0.66 g of 2,8-dichlorobenzofuro[2,3-b]pyrazine, which was a target substance, was obtained in a yield of 75%. A synthesis scheme of Step 2 is shown in (b-2).

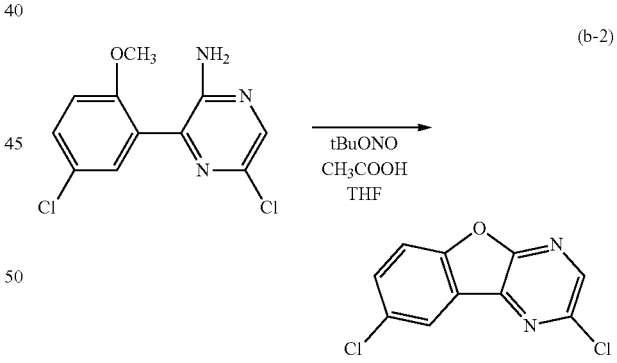

Step 3: Synthesis of 2,8-bis[3-(dibenzothiophen-4-yl)phenyl]benzofuro[2,3-b]pyrazine (Abbreviation: 2,8mDBtP2Bfpr)

Then, into a three-neck flask were put 0.66 g of 2,8-dichlorobenzofuro[2,3-b]pyrazine obtained through Step 2, 1.90 g of a 3-(4-dibenzothiophene)phenylboronic acid, 3.59 g of tripotassium phosphate, 23 mL of diglyme, and 1.6 mL of tert-butanol, and the air in the flask was replaced with nitrogen. The mixture in the flask was degassed by being stirred under reduced pressure, 0.026 g of palladium(II) acetate and 0.086 g of di(1-adamantyl)-n-butylphosphine (abbreviation: CataCXiumA) were added thereto, and the resulting mixture was stirred at 140° C. for 15 hours to be reacted. After a predetermined time elapsed, the obtained suspension was subjected to suction filtration and was washed with water and ethanol. The obtained solid was purified by silica gel column chromatography using toluene as a developing solvent, and then recrystallization from a mixed solvent of toluene and hexane was performed, whereby 0.61 g of 2,8mDBtP2Bfpr, which was a target white solid, was obtained in a yield of 32%. A synthesis scheme of Step 3 is shown in (b-3).

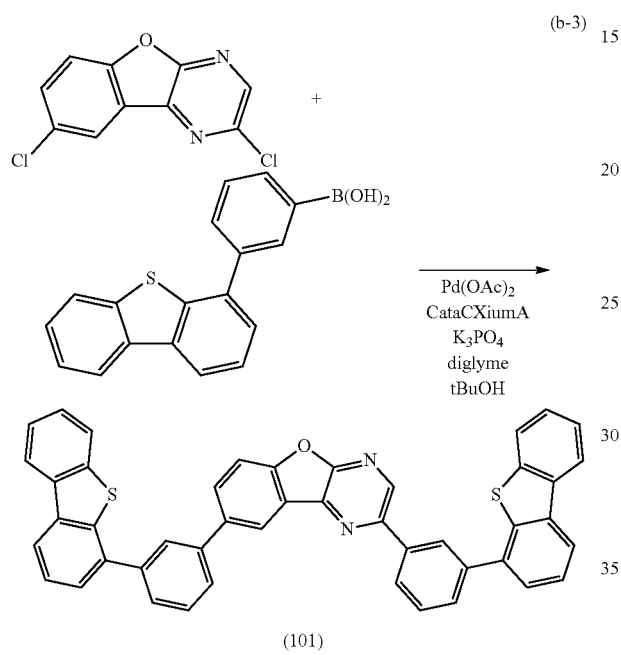

(101)

Then, 0.60 g of this yellowish white powder solid was purified twice by a train sublimation method. In the purification by sublimation, the yellowish white powder solid was heated at 355° C. under a pressure of 2.7 Pa with an argon gas at a flow rate of 5 mL/min. After the purification by sublimation, 0.44 g of a target yellowish white solid was obtained at a collection rate of 73%.

The obtained solid was subjected to nuclear magnetic resonance spectrometry ($^1$H NMR), and the results are shown below.

$^1$H-NMR. δ (CD$_2$Cl$_2$): 7.32 (s, 1H), 7.46-7.52 (m, 4H), 7.61-7.64 (m, 4H), 7.68 (t, 1H), 7.74 (t, 1H), 7.79-7.90 (m, 5H), 8.05 (dd, 1H), 8.13 (s, 1H), 8.22-8.26 (m, 5H), 8.56 (s, 1H), 8.62 (d, 1H), 8.95 (s, 1H).

Figure 13A:
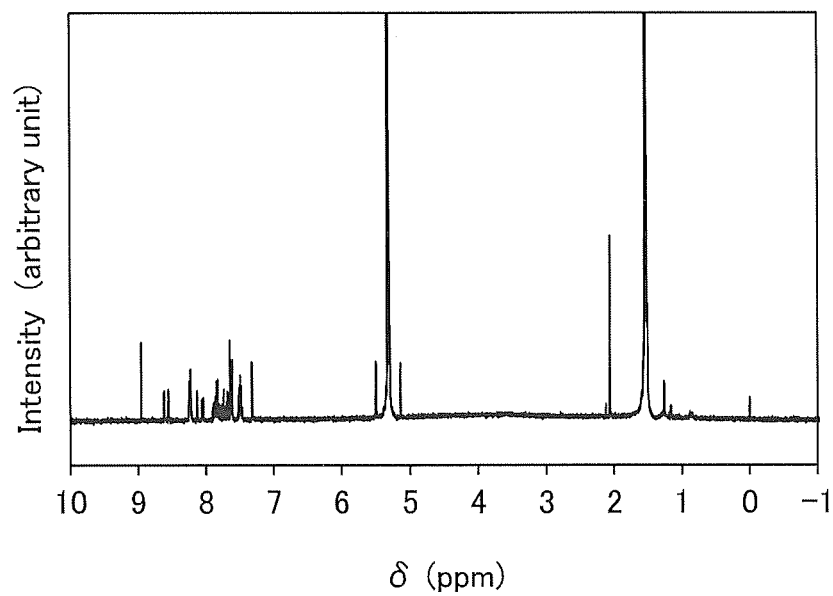
FIGS. 13A and 13B show NMR charts of a compound in Example.
Figure 13B:
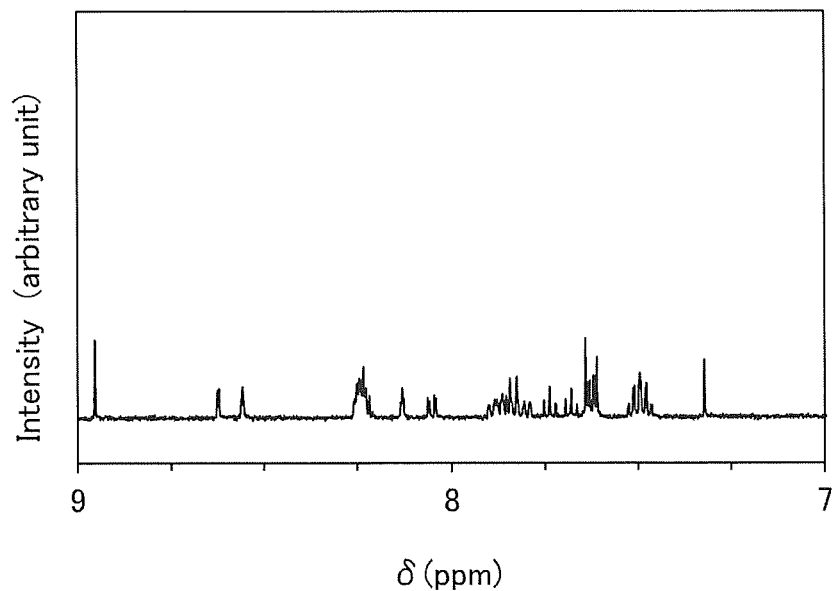

FIGS. 13A and 13B are $^1$H NMR charts of the obtained solid. Note that FIG. 13B is a chart showing an enlarged part in the range of 7.0 ppm to 9.0 ppm of FIG. 13A. The measurement results indicate that the target substance, 2,8mDBtP2Bfpr was obtained.

<Characteristics of 2,8mDBtP2Bfpr>

Figure 14:
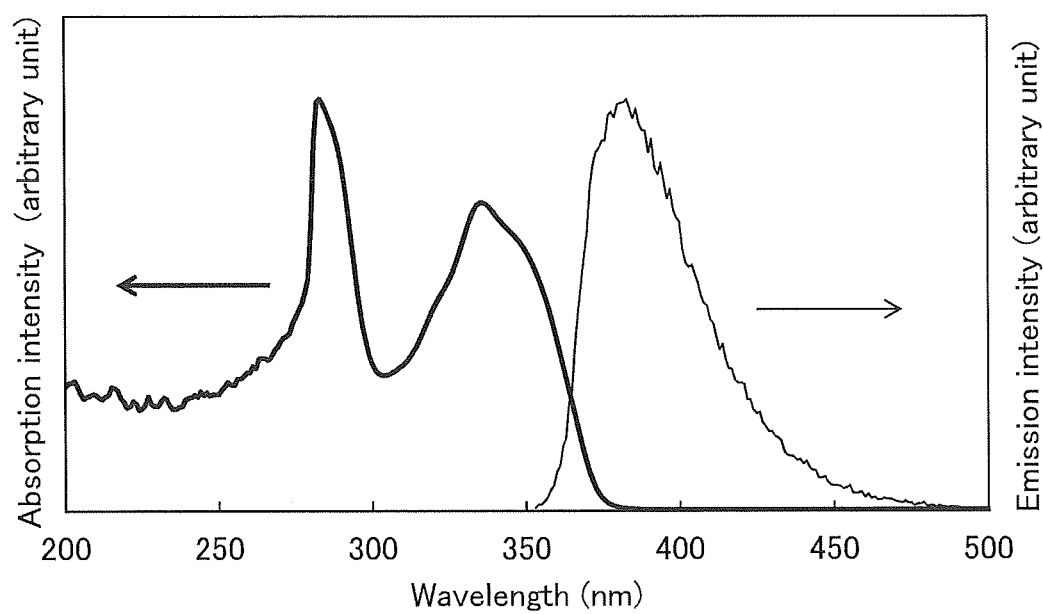
FIG. 14 shows absorption and emission spectra of a compound in Example.

Next, FIG. 14 shows an absorption spectrum and an emission spectrum of 2,8mDBtP2Bfpr in a toluene solution. Note that the method for measuring the absorption spectrum and the emission spectrum of 2,8mDBtP2Bfpr in the toluene solution was the same as that described in Example 1.

FIG. 14 shows that 2,8mDBtP2Bfpr in the toluene solution has absorption spectrum peaks around 283 nm and 336 nm, and an emission spectrum peak around 383 nm (excitation wavelength: 338 nm).

Example 3

In this example, a fabrication example of a light-emitting element including the organic compound of one embodiment of the present invention and characteristics of the light-emitting element are described. A cross-sectional view of the light-emitting element fabricated in this example is similar to that in FIG. 1A. Table 1 shows details of the element structure. In addition, structures and abbreviations of compounds used here are shown below. Note that Examples described above can be referred to for other compounds.

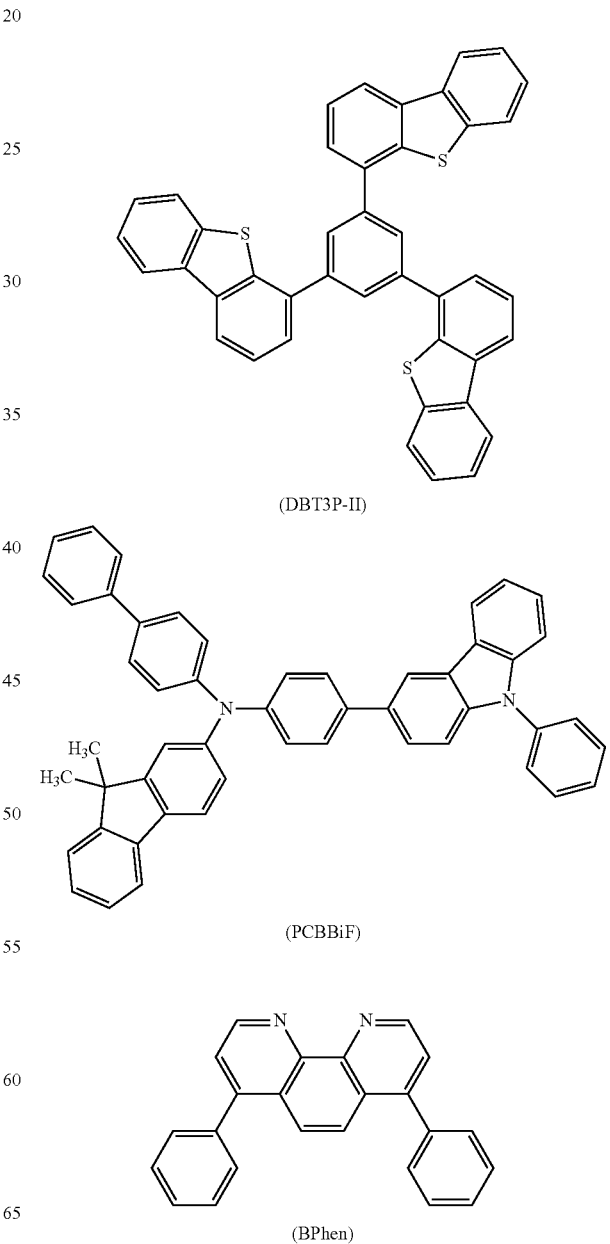

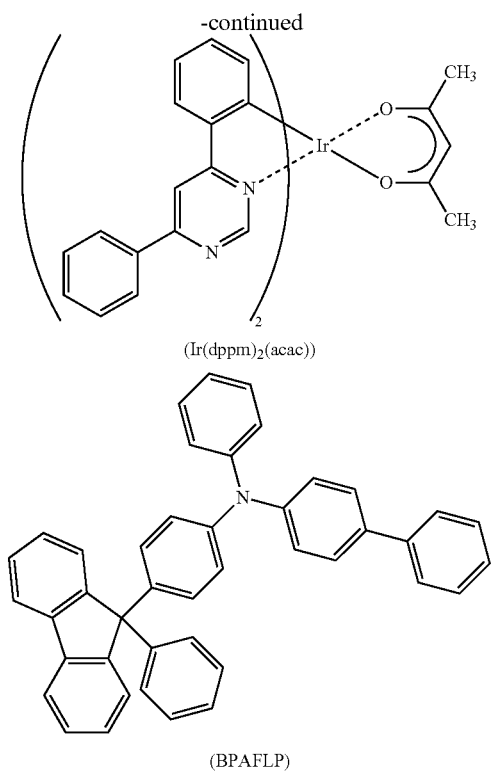

(Ir(dppm)₂(acac))

(BPAFLP)

3,8mDBtP2Bfpr, N-(1,1'-biphenyl-4-yl)-9,9-dimethyl-N-[4-(9-phenyl-9H-carbazol-3-yl)phenyl]-9H-fluor en-2-amine (abbreviation: PCBBiF), and bis[2-(6-phenyl-4-pyrimidinyl-κN³)phenyl-KC](2,4-pentanedionato-κ²O,O')iridium (III) (abbreviation: Ir(dppm)₂(acac)) were co-evaporated at a weight ratio of 3,8mDBtP2Bfpr: PCBBiF: Ir(dppm)₂(acac))=0.7:0.3:0.05 to a thickness of 20 nm. Then, a light-emitting layer 140(2) was formed by co-evaporation with a weight ratio of 3,8mDBtP2Bfpr: PCBBiF: Ir(dppm)₂(acac) =0.8:0.2:0.05 to a thickness of 20 nm. Note that in the light-emitting layers 140, Ir(dppm)₂(acac) corresponds to a guest material that emits phosphorescence.

As the electron-transport layer 118, 3,8mDBtP2Bfpr was deposited by evaporation over the light-emitting layer 140 to a thickness of 20 nm and bathophenanthroline (abbreviation: BPhen) was deposited thereover by evaporation to a thickness of 20 nm. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the light-emitting element 1 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/cm² and heat treatment at 80° C. for one hour were performed. Through the process, the light-emitting element 1 was obtained.

TABLE 1

| Layer | | Numeral | Thickness (nm) | Material | Weight ratio |
|---|---|---|---|---|---|
| Light-emitting element 1 | Electrode | 102 | 200 | Al | — |
| | Electron-injection layer | 119 | 1 | LiF | — |
| | Electron-transport layer | 118(2) | 20 | Bphen | — |
| | | 118(1) | 20 | 3,8mDBtP2Bfpr | — |
| | Light-emitting layer | 140(2) | 20 | 3,8mDBtP2Bfpr:PCBBiF:Ir(dppm)₂(acac) | 0.8:0.2:0.05 |
| | | 140(1) | 20 | 3,8mDBtP2Bfpr:PCBBiF:Ir(dppm)₂(acac) | 0.7:0.3:0.05 |
| | Hole-transport layer | 112 | 20 | BPAFLP | — |
| | Hole-injection layer | 111 | 60 | DBT3P-II:MoO₃ | 1:0.5 |
| | Electrode | 101 | 70 | ITSO | — |

«Fabrication of Light-Emitting Element 1»

As the electrode 101, an ITSO film was formed to a thickness of 70 nm over the substrate 200. The electrode area of the electrode 101 was set to 4 mm² (2 mm×2 mm).

As the hole-injection layer 111, 4,4',4''-(benzene-1,3,5-triyl)tri(dibenzothiophene) (abbreviation: DBT3P-II) and molybdenum oxide (MoO₃) were deposited over the electrode 101 by co-evaporation in a weight ratio of DBT3P-II: MoO₃=1:0.5 to a thickness of 60 nm.

As the hole-transport layer 112, 4-phenyl-4'-(9-phenylfluoren-9-yl)triphenylamine (abbreviation: BPAFLP) was deposited over the hole-injection layer 111 by evaporation to a thickness of 20 nm.

Next, a light-emitting layer 140(1) was formed over the hole-transport layer 112 in such a manner that <Characteristics of Light-Emitting Element>

Figure 15:
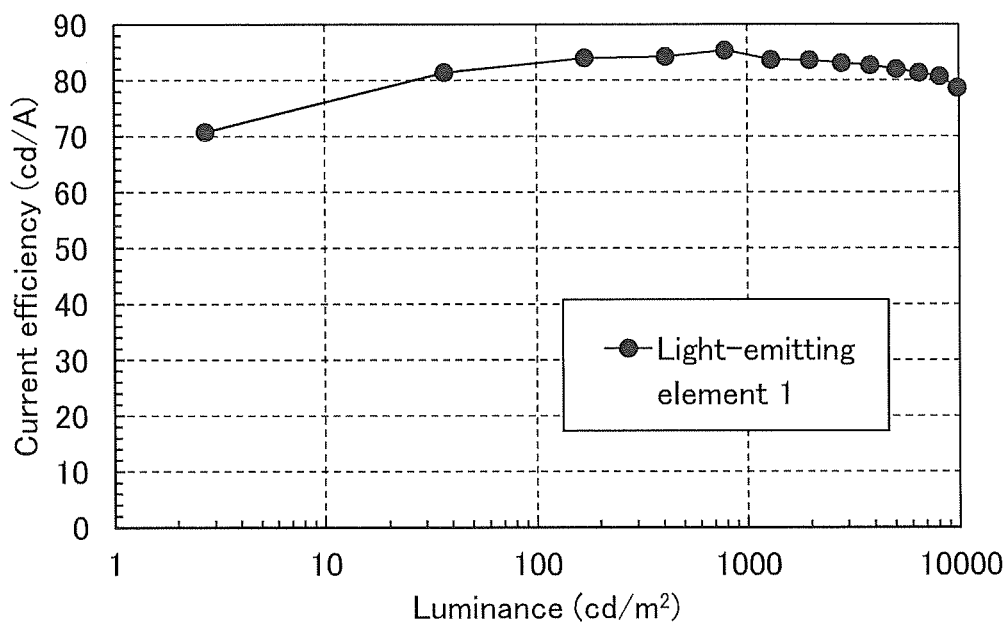
FIG. 15 shows current efficiency-luminance characteristics of a light-emitting element in Example.
Figure 16:
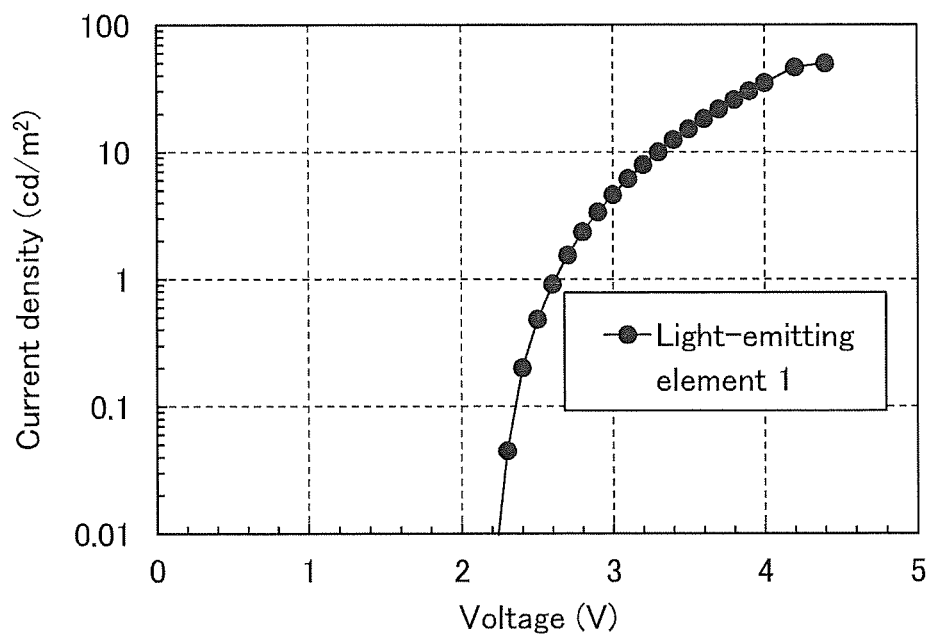
FIG. 16 shows current density-voltage characteristics of a light-emitting element in Example.
Figure 17:
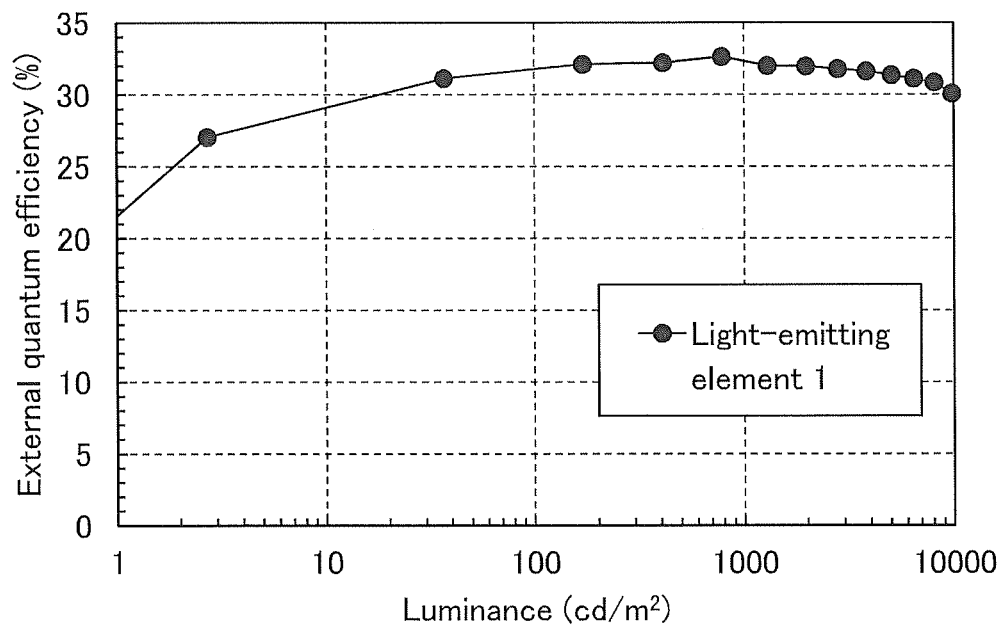
FIG. 17 shows external quantum efficiency-luminance characteristics of a light-emitting element in Example.
Figure 18:
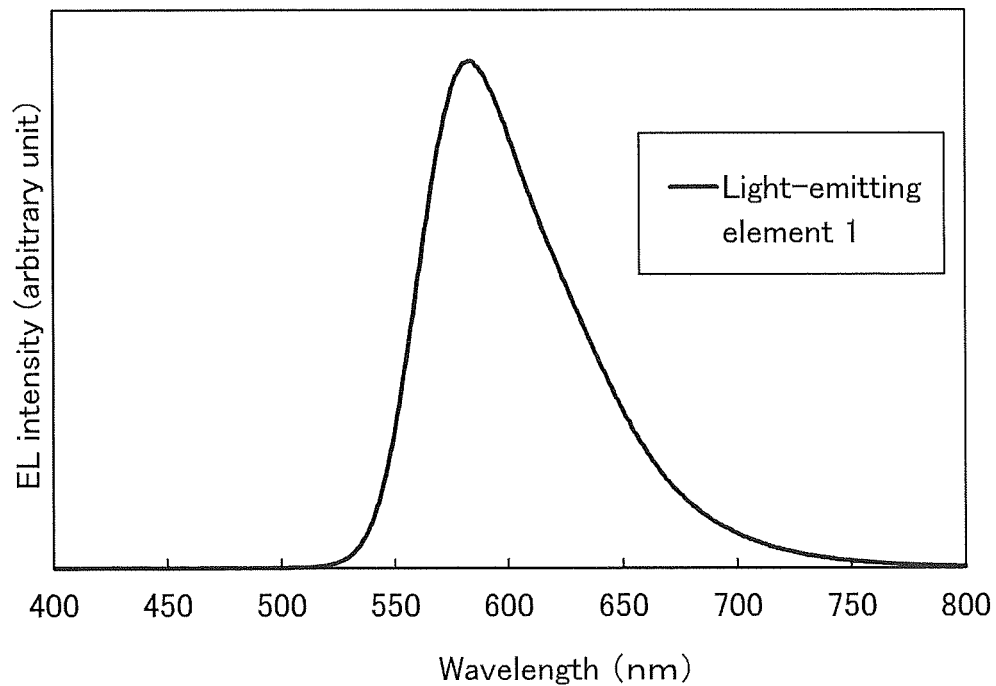
FIG. 18 shows an electroluminescence spectrum of a light-emitting element in Example.

FIG. 15 shows current efficiency-luminance characteristics of the fabricated light-emitting element 1. FIG. 16 shows current density-voltage characteristics. FIG. 17 shows external quantum efficiency-luminance characteristics. The measurement of the light-emitting element 1 was performed at room temperature (in an atmosphere kept at 23° C.). FIG. 18 shows the electroluminescence spectrum when a current at a current density of 2.5 mA/cm² is supplied to the light-emitting element 1. The measurement was carried out at room temperature.

Table 2 shows element characteristics of the light-emitting element 1 at around 1000 cd/m².

TABLE 2

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 1 | 2.6 | 0.92 | (0.55, 0.45) | 784 | 85 | 103 | 32.6 |

From FIG. 15, FIG. 17, and Table 2, it is found that the light-emitting element 1 has high current efficiency and high external quantum efficiency. In addition, a fall (roll-off) in the emission efficiency of the light-emitting element 1 is small even on the high luminance side, which is excellent.

Furthermore, as shown in Table 2, the light-emitting element 1 was driven at a low voltage of 2.6 V at around 1000 cd/m² and thus exhibited high power efficiency.

FIG. 18 shows that the light-emitting element 1 emits orange light with an electroluminescence spectrum peak of 584 nm and a full width at half maximum of 73 nm. The obtained electroluminescence spectrum reveals that the orange light is emitted from Ir(dppm)$_2$(acac) that is used as a guest material.

<Reliability of Light-Emitting Element>

Figure 19:
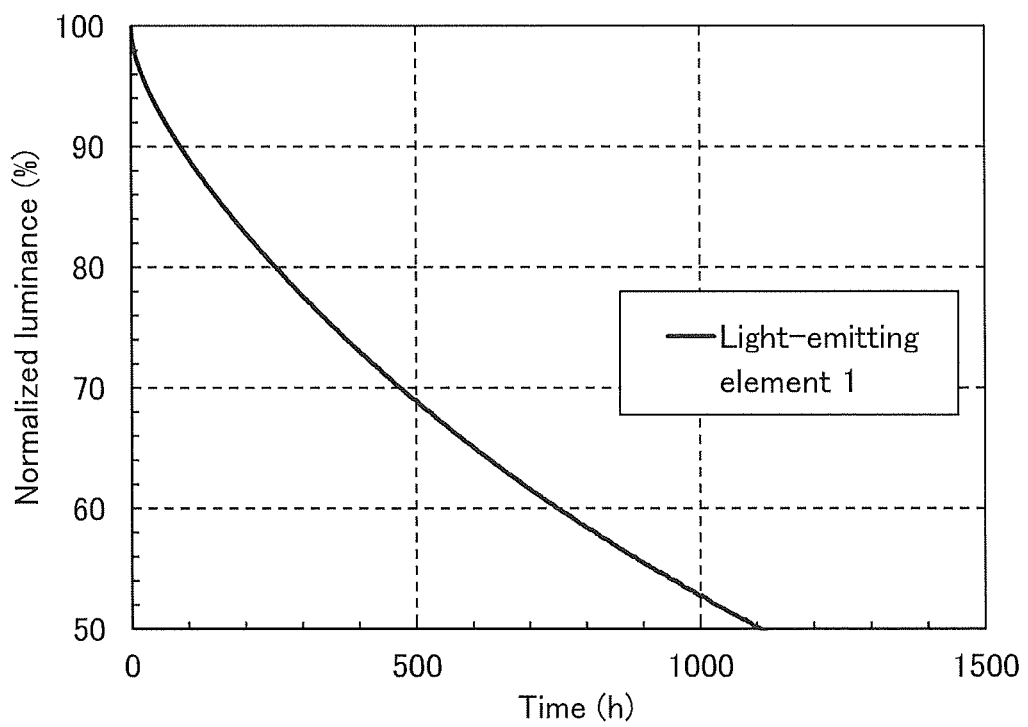
FIG. 19 shows a reliability test result of a light-emitting element in Example.

Next, a driving test at a constant current of 2 mA was performed on the light-emitting element 1. FIG. 19 shows the results. As seen from FIG. 19, the luminance half life of the light-emitting element 1 exceeds 1000 hours; thus, the light-emitting element 1 has significantly high reliability.

As described above, by using a compound of one embodiment of the present invention in a light-emitting layer, a light-emitting element with high emission efficiency can be fabricated. A light-emitting element which is driven at a low voltage and has reduced power consumption can be fabricated. Moreover, a highly reliable light-emitting element can be manufactured.

Example 4

In this example, a fabrication example of a light-emitting element including the organic compound of one embodiment of the present invention, which is different from that described in Example 3, and characteristics of the light-emitting element are described. A cross-sectional view of the light-emitting element fabricated in this example is similar to that in FIG. 1A. Table 3 shows details of the element structure. In addition, structures and abbreviations of compounds used here are shown below. Note that Examples described above can be referred to for other compounds.

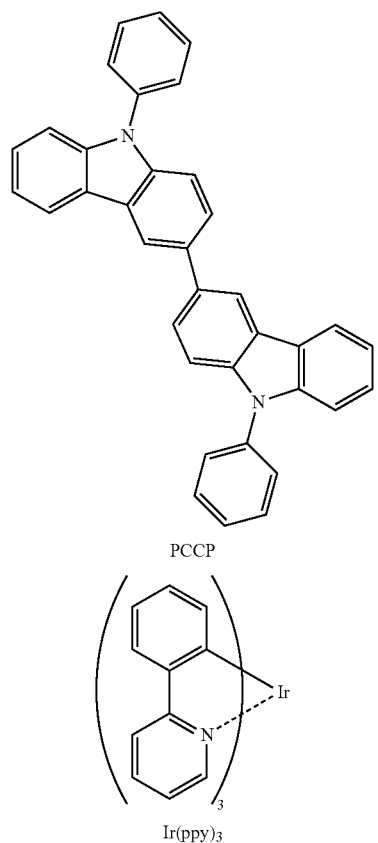

PCCP

Ir(ppy)$_3$

TABLE 3

| Layer | | Numeral | Thickness (nm) | Material | Weight ratio |
|---|---|---|---|---|---|
| Light-emitting element 2 | Electrode | 102 | 200 | Al | — |
| | Electron-injection layer | 119 | 1 | LiF | — |
| | Electron-transport layer | 118(2) | 10 | Bphen | — |
| | | 118(1) | 15 | 2,8mDBtP2Bfpr | — |
| | Light-emitting layer | 140(2) | 20 | 2,8mDBtP2Bfpr:PCCP:Ir(ppy)$_3$ | 0.8:0.2:0.1 |
| | | 140(1) | 20 | 2,8mDBtP2Bfpr:PCCP:Ir(ppy)$_3$ | 0.5:0.5:0.1 |
| | Hole-transport layer | 112 | 20 | PCCP | — |

TABLE 3-continued

| Layer | Numeral | Thickness (nm) | Material | Weight ratio |
|---|---|---|---|---|
| Hole-injection layer | 111 | 45 | DBT3P-II:MoO$_3$ | 1:0.5 |
| Electrode | 101 | 70 | ITSO | — |

«Fabrication of Light-Emitting Element 2»

As the electrode 101, an ITSO film was formed to a thickness of 70 nm over the substrate 200. The electrode area of the electrode 101 was set to 4 mm$^2$ (2 mm×2 mm).

As the hole-injection layer 111, DBT3P-II and molybdenum oxide were deposited over the electrode 101 by co-evaporation in a weight ratio of DBT3P-II: MoO$_3$=1:0.5 to a thickness of 45 nm.

As the hole-transport layer 112, PCCP was deposited over the hole-injection layer 111 by evaporation to a thickness of 20 nm.

Next, a light-emitting layer 140(1) was formed over the hole-transport layer 112 in such a manner that 2,8mDBtP2Bfpr, PCCP, and Ir(ppy)$_3$ were co-evaporated at a weight ratio of 2,8mDBtP2Bfpr: PCCP: Ir(ppy)$_3$)=0.5:0.5:0.1 to a thickness of 20 nm. Then, a light-emitting layer 140(2) was formed by co-evaporation with a weight ratio of 2,8mDBtP2Bfpr: PCCP: Ir(ppy)$_3$=0.8:0.2:0.1 to a thickness of 20 nm. Note that in the light-emitting layers 140, Ir(ppy)$_3$ corresponds to a guest material that emits phosphorescence.

As the electron-transport layer 118, 2,8mDBtP2Bfpr was deposited by evaporation over the light-emitting layer 140 to a thickness of 15 nm and BPhen was deposited thereover by evaporation to a thickness of 10 nm. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the light-emitting element 2 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/cm$^2$ and heat treatment at 80° C. for one hour were performed. Through the process, the light-emitting element 2 was obtained.

<Characteristics of Light-Emitting Element>

Figure 20:
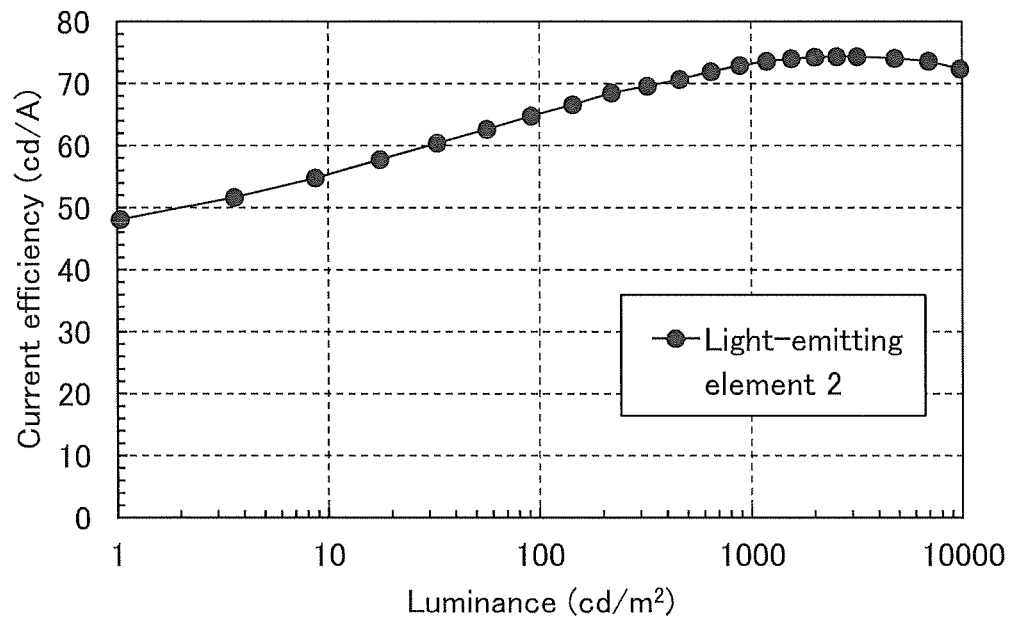
FIG. 20 shows current efficiency-luminance characteristics of a light-emitting element in Example.
Figure 21:
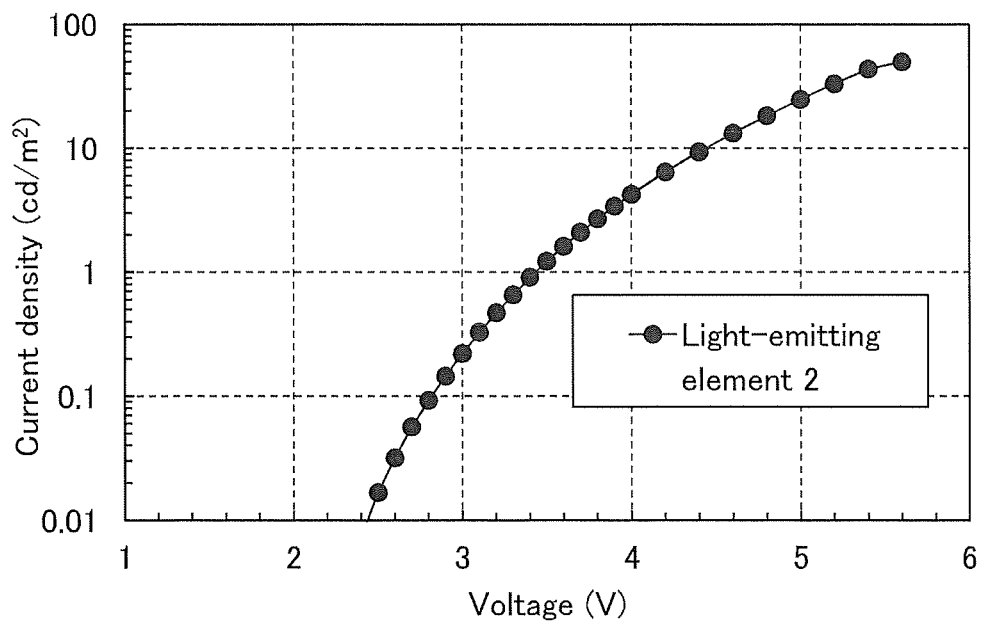
FIG. 21 shows current density-voltage characteristics of a light-emitting element in Example.
Figure 22:
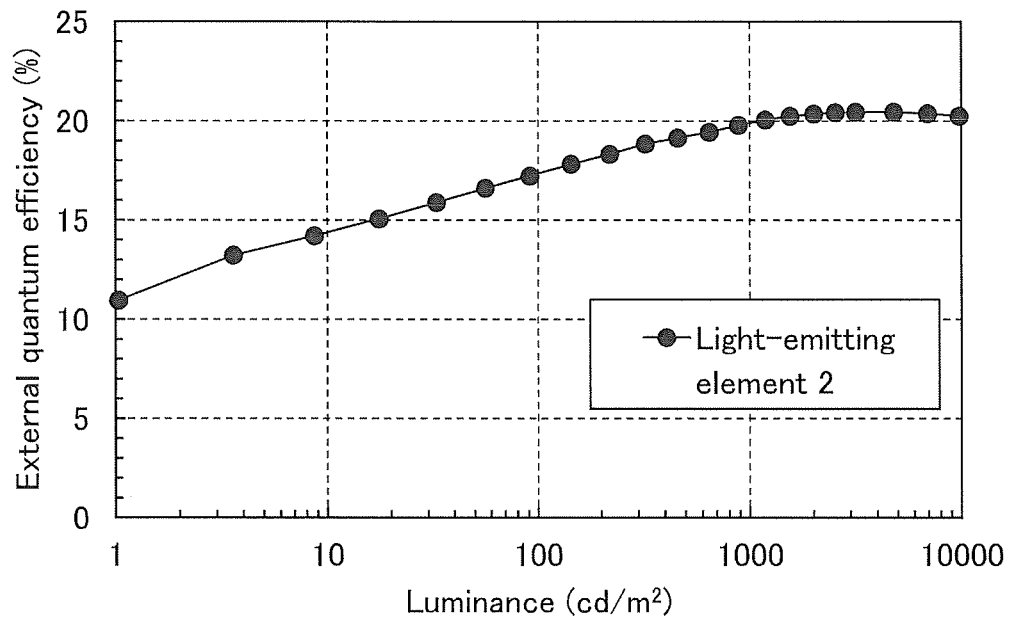
FIG. 22 shows external quantum efficiency-luminance characteristics of a light-emitting element in Example.
Figure 23:
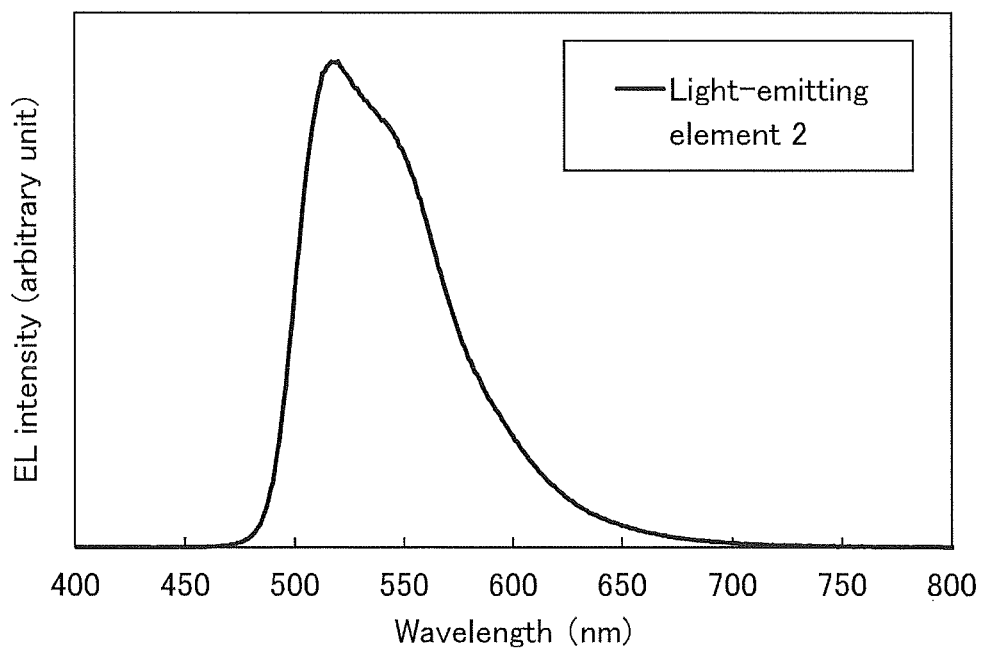
FIG. 23 shows an emission spectrum of a light-emitting element in Example.

FIG. 20 shows current efficiency-luminance characteristics of the fabricated light-emitting element 2. FIG. 22 shows current density-voltage characteristics. FIG. 21 shows external quantum efficiency-luminance characteristics. The measurement of the light-emitting element 2 was performed at room temperature (in an atmosphere kept at 23° C.). FIG. 23 shows the electroluminescence spectrum when a current at a current density of 2.5 mA/cm$^2$ is supplied to the light-emitting element 2. The measurement was carried out at room temperature.

Table 4 shows element characteristics of the light-emitting element 2 at around 1000 cd/m$^2$.

TABLE 4

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 2 | 3.5 | 1.23 | (0.32, 0.63) | 884 | 72 | 65 | 20 |

From FIG. 20, FIG. 22, and Table 4, it is found that the light-emitting element 1 has high current efficiency and high external quantum efficiency. In addition, a fall (roll-off) in the emission efficiency of the light-emitting element 1 is small even on the high luminance side, which is excellent.

Furthermore, as shown in FIG. 21 and Table 4, the light-emitting element 2 is driven at a low voltage and thus exhibits high power efficiency.

FIG. 23 shows that the light-emitting element 1 emits green light with an electroluminescence spectrum peak of 520 nm and a full width at half maximum of 72 nm. The obtained electroluminescence spectrum reveals that the green light is emitted from Ir(ppy)$_3$ that is used as a guest material.

<Reliability of Light-Emitting Element>

Figure 24:
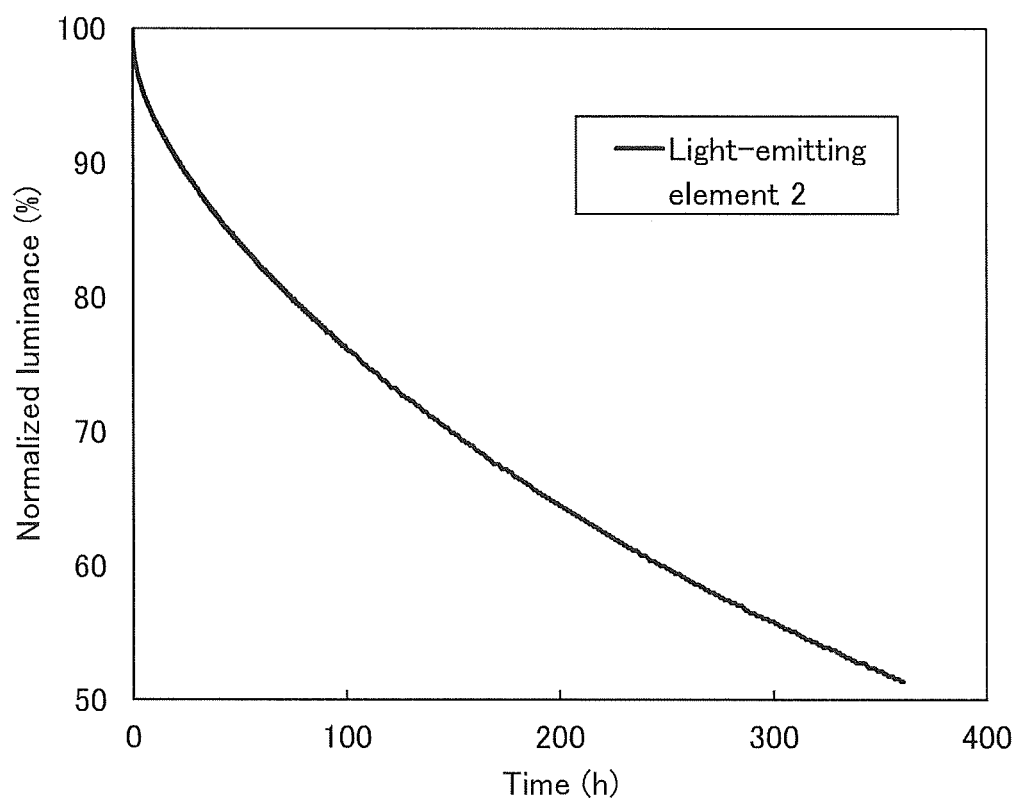
FIG. 24 shows a reliability test result of a light-emitting element in Example.

Next, a driving test at a constant current of 2 mA was performed on the light-emitting element 2. FIG. 24 shows the results. As seen from FIG. 24, the luminance half life of the light-emitting element 2 exceeds 350 hours; thus, the light-emitting element 2 has high reliability.

As described above, by using a compound of one embodiment of the present invention in a light-emitting layer, a light-emitting element with high emission efficiency can be fabricated. A light-emitting element which is driven at a low voltage and has reduced power consumption can be fabricated. Moreover, a highly reliable light-emitting element can be manufactured.

REFERENCE NUMERALS

100: EL layer, 101: electrode, 102: electrode, 106: light-emitting unit, 110: light-emitting unit, 111: hole-injection layer, 112: hole-transport layer, 113: electron-transport layer, 114: electron-injection layer, 115: charge-generation layer, 116: hole-injection layer, 117: hole-transport layer, 118: electron-transport layer, 119: electron-injection layer, 120: light-emitting layer, 130: light-emitting layer, 140: light-emitting layer, 141: host material, 141_1: organic compound, 141_2: organic compound, 142: guest material, 150: light-emitting element, 170: light-emitting layer, 200: substrate, 220: substrate, 250: light-emitting element, 601: source side driver circuit, 602: pixel portion, 603: gate side driver circuit, 604: sealing substrate, 605: sealant, 607: space, 608: wiring, 610: element substrate, 611: switching TFT, 612: current controlling TFT, 613: electrode, 614: insulator, 616: EL layer, 617: electrode, 618: light-emitting element, 623: n-channel TFT, 624: p-channel TFT, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation button, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition wall, 1028: EL layer, 1029: electrode, 1031: sealing substrate, 1032: sealant, 1033: base material, 1034B: coloring layer, 1034G: coloring layer, 1034R: coloring layer, 1035: black layer, 1036: overcoat layer, 1037: interlayer insulating film, 1040: pixel portion, 1041: driver circuit portion, 1042: peripheral portion, 3500: multifunction terminal, 3502: housing, 3504: display portion, 3506: camera, 3508: lighting, 3600: light, 3602: housing, 3608: lighting, 3610: speaker, 8501: lighting device, 8502: lighting device, 8503: lighting device, 8504: lighting device, 9000: housing, 9001: display portion, 9003: speaker, 9005: operation key, 9006: connection terminal, 9007: sensor, 9008: microphone, 9055: hinge, 9200: portable information terminal, 9201: portable information terminal, and 9202: portable information terminal.

This application is based on Japanese Patent Application Serial No. 2016-254916 filed with Japan Patent Office on Dec. 28, 2016, the entire contents of which are hereby incorporated by reference.

The invention claimed is:

1. An organic compound represented by General Formula (G4):

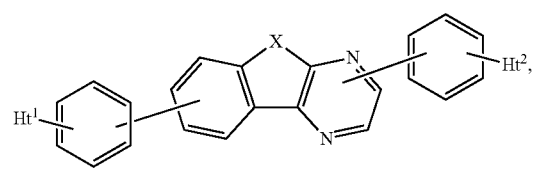

(G4)

wherein:

X represents oxygen or sulfur;

each of $Ht^1$ and $Ht^2$ independently represents a substituted or unsubstituted heteroaromatic ring including a dibenzofuran ring or a dibenzothiophene ring.

2. The organic compound according to claim 1, wherein the organic compound is represented by General Formula (G5):

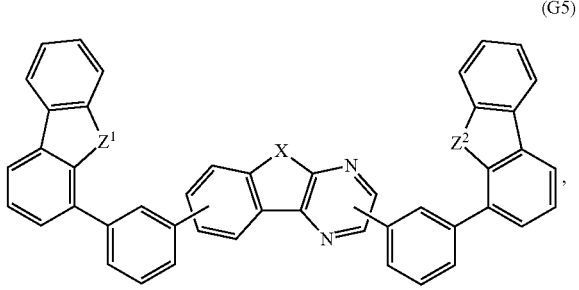

(G5)

wherein:

each of $Z^1$ and $Z^2$ independently represents oxygen or sulfur.

3. The organic compound according to claim 1, wherein the organic compound is represented by Structural Formula (100) or Structural Formula (101):

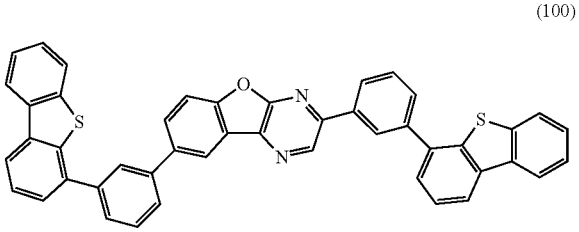

(100)

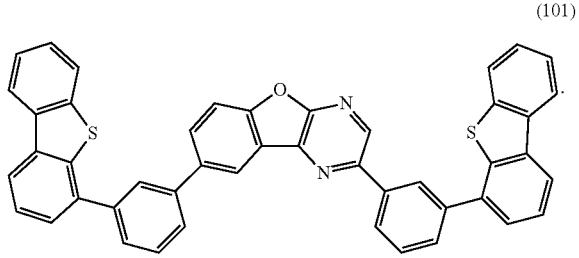

(101)

4. A light-emitting element comprising the organic compound according to claim 1.

5. A display device comprising:
the light-emitting element according to claim 4; and
at least one of a color filter and a transistor.

6. An electronic device comprising:
the display device according to claim 5; and
at least one of a housing and a touch sensor.

7. A lighting device comprising:
the light-emitting element according to claim 4; and
at least one of a housing and a touch sensor.

* * * * *